(12) United States Patent
Owens et al.

(10) Patent No.: US 11,648,418 B2
(45) Date of Patent: May 16, 2023

(54) SYSTEMS AND METHODS FOR BIOLOGICAL ADAPTIVE RADIOTHERAPY

(71) Applicant: RefleXion Medical, Inc., Hayward, CA (US)

(72) Inventors: Michael Kirk Owens, San Francisco, CA (US); Rostem Bassalow, Hayward, CA (US); Peter Demetri Olcott, Los Gatos, CA (US); Yevgen Voronenko, Sunnyvale, CA (US); David Quentin Larkin, Menlo Park, CA (US); Samuel Mazin, Menlo Park, CA (US)

(73) Assignee: Reflexion Medical, Inc., Hayward, CA (US)

( * ) Notice: Subject to any disclaimer, the term of this patent is extended or adjusted under 35 U.S.C. 154(b) by 1128 days.

(21) Appl. No.: 16/016,272

(22) Filed: Jun. 22, 2018

(65) Prior Publication Data
US 2018/0369611 A1   Dec. 27, 2018

Related U.S. Application Data

(60) Provisional application No. 62/523,691, filed on Jun. 22, 2017.

(51) Int. Cl.
*A61N 5/10* (2006.01)
(52) U.S. Cl.
CPC ......... *A61N 5/1031* (2013.01); *A61N 5/1039* (2013.01); *A61N 5/1049* (2013.01);
(Continued)

(58) Field of Classification Search
CPC .... A61N 2005/1034; A61N 2005/1052; A61N 2005/1055; A61N 2005/1058;
(Continued)

(56) References Cited

U.S. PATENT DOCUMENTS 3,794,840 A   2/1974  Scott
3,987,281 A   10/1976 Hodes
(Continued)

FOREIGN PATENT DOCUMENTS

CN   1681436 A   10/2005
CN   1824342 A   8/2006
(Continued)

OTHER PUBLICATIONS

Nina Tunçel. "Adaptive radiotherapy from past to future frontiers." International Journal of Radiology & Radiation Therapy 2021; 8(2): 81-84.*
(Continued)

*Primary Examiner* — Jonathan Cwern
(74) *Attorney, Agent, or Firm* — Cooley LLP

(57) ABSTRACT

Disclosed herein are systems and methods for adapting and/or updating radiotherapy treatment plans based on biological and/or physiological data and/or anatomical data extracted or calculated from imaging data acquired in real-time (e.g., during a treatment session). Functional imaging data acquired at the time of radiation treatment is used to modify a treatment plan and/or dose delivery instructions to provide a prescribed dose distribution to patient target regions. Also disclosed herein are methods for evaluating treatment plans based on imaging data acquired in real-time.

53 Claims, 21 Drawing Sheets

(52) U.S. Cl.
CPC ......... *A61N 5/1064* (2013.01); *A61N 5/1067* (2013.01); *A61N 5/1068* (2013.01); *A61N 5/1036* (2013.01); *A61N 5/1037* (2013.01); *A61N 5/1038* (2013.01); *A61N 5/1045* (2013.01); *A61N 2005/1034* (2013.01); *A61N 2005/1052* (2013.01); *A61N 2005/1055* (2013.01); *A61N 2005/1058* (2013.01)

(58) Field of Classification Search
CPC .. A61N 5/1031; A61N 5/1036; A61N 5/1037; A61N 5/1038; A61N 5/1039; A61N 5/1045; A61N 5/1049; A61N 5/1067
See application file for complete search history.

(56) References Cited

U.S. PATENT DOCUMENTS

| | | | |
|---|---|---|---|
| 5,297,037 A | 3/1994 | Ifuku | |
| 5,418,827 A | 5/1995 | Deasy et al. | |
| 5,418,828 A | 5/1995 | Carpenter | |
| 5,673,300 A | 9/1997 | Reckwerdt et al. | |
| 5,813,985 A | 9/1998 | Carroll | |
| 6,023,494 A | 2/2000 | Senzig et al. | |
| 6,038,283 A | 3/2000 | Carol et al. | |
| 6,393,096 B1 | 5/2002 | Carol et al. | |
| 6,411,675 B1 | 6/2002 | Llacer | |
| 6,438,202 B1 | 8/2002 | Olivera et al. | |
| 6,455,856 B1 | 9/2002 | Gagnon | |
| 6,459,762 B1 | 10/2002 | Wong et al. | |
| 6,504,899 B2 | 1/2003 | Pugachev et al. | |
| 6,661,870 B2 | 12/2003 | Kapatoes et al. | |
| 6,700,949 B2 | 3/2004 | Susami et al. | |
| 6,719,683 B2 | 4/2004 | Frohlich | |
| 6,735,277 B2 | 5/2004 | McNutt et al. | |
| 6,810,108 B2 | 10/2004 | Clark et al. | |
| 7,015,490 B2 | 3/2006 | Wang et al. | |
| 7,265,356 B2 | 9/2007 | Pelizzari et al. | |
| 7,266,175 B1 | 9/2007 | Romesberg | |
| 7,280,633 B2 | 10/2007 | Cheng et al. | |
| 7,302,038 B2 | 11/2007 | Mackie et al. | |
| 7,343,030 B2 | 3/2008 | Sawyer | |
| 7,379,531 B2 | 5/2008 | Esham et al. | |
| 7,391,026 B2 | 6/2008 | Trinkaus et al. | |
| 7,412,029 B2 | 8/2008 | Myles | |
| 7,412,280 B2 | 8/2008 | Hertel et al. | |
| 7,415,095 B2 | 8/2008 | Wofford et al. | |
| 7,446,328 B2 | 11/2008 | Rigney et al. | |
| 7,453,984 B2 | 11/2008 | Chen et al. | |
| 7,496,181 B2 | 2/2009 | Mazin et al. | |
| 7,508,967 B2 | 3/2009 | Harari et al. | |
| 7,513,861 B2 | 4/2009 | Klein et al. | |
| 7,574,251 B2 | 8/2009 | Lu et al. | |
| 7,611,452 B2 | 11/2009 | Allison et al. | |
| 7,636,420 B2 | 12/2009 | Spies et al. | |
| 7,639,853 B2 | 12/2009 | Olivera et al. | |
| 7,657,304 B2 | 2/2010 | Mansfield et al. | |
| 7,693,257 B2 | 4/2010 | Allison | |
| 7,715,606 B2 | 5/2010 | Jeung et al. | |
| 7,831,073 B2 | 11/2010 | Fu et al. | |
| 7,839,972 B2 | 11/2010 | Ruchala et al. | |
| 7,844,560 B2 | 11/2010 | Krishnan et al. | |
| 7,907,987 B2 | 3/2011 | Dempsey | |
| 7,983,380 B2 | 7/2011 | Guertin et al. | |
| 7,995,813 B2 | 8/2011 | Foshee et al. | |
| 8,017,915 B2 | 9/2011 | Mazin | |
| 8,019,042 B2 | 9/2011 | Shukla et al. | |
| 8,063,376 B2 | 11/2011 | Maniawski et al. | |
| 8,073,103 B2 | 12/2011 | Otto et al. | |
| 8,073,104 B2 | 12/2011 | Yan et al. | |
| 8,090,074 B2 | 1/2012 | Filiberti et al. | |
| 8,107,589 B2 | 1/2012 | Sakurai et al. | |
| 8,119,978 B2 | 2/2012 | Islam et al. | |
| 8,121,252 B2 | 2/2012 | Nord et al. | |
| 8,144,833 B2 | 3/2012 | Breedveld | |
| 8,144,962 B2 | 3/2012 | Busch et al. | |
| 8,149,991 B2 | 4/2012 | Moreau | |
| 8,180,020 B2 | 5/2012 | Kilby et al. | |
| 8,199,990 B2 | 6/2012 | Foshee et al. | |
| 8,232,535 B2 | 7/2012 | Olivera et al. | |
| 8,260,013 B2 | 9/2012 | Pekar et al. | |
| 8,269,195 B2 | 9/2012 | Rigney et al. | |
| 8,278,633 B2 | 10/2012 | Nord et al. | |
| 8,295,906 B2 | 10/2012 | Saunders et al. | |
| 8,331,532 B2 | 12/2012 | Nord et al. | |
| 8,406,844 B2 | 3/2013 | Ruchala et al. | |
| 8,437,449 B2 | 5/2013 | Riley et al. | |
| 8,442,287 B2 | 5/2013 | Fordyce, II et al. | |
| 8,461,538 B2 | 6/2013 | Mazin | |
| 8,467,497 B2 | 6/2013 | Lu et al. | |
| 8,483,803 B2 | 7/2013 | Partain et al. | |
| 8,509,383 B2 | 8/2013 | Lu et al. | |
| 8,579,784 B2 | 11/2013 | Krishnan et al. | |
| 8,588,367 B2 | 11/2013 | Busch et al. | |
| 8,605,857 B1 | 12/2013 | Renner | |
| 8,658,992 B2 | 2/2014 | Otto | |
| 8,681,938 B2 | 3/2014 | Myles | |
| 8,696,538 B2 | 4/2014 | Otto | |
| 8,699,664 B2 | 4/2014 | Otto et al. | |
| 8,744,045 B2 | 6/2014 | Nord et al. | |
| 8,748,825 B2 | 6/2014 | Mazin | |
| 8,767,917 B2 | 7/2014 | Ruchala et al. | |
| 8,812,240 B2 | 8/2014 | Yu et al. | |
| 8,816,307 B2 | 8/2014 | Kuusela et al. | |
| 8,836,697 B2 | 9/2014 | Nord et al. | |
| 8,971,489 B2 | 3/2015 | Ruan et al. | |
| 8,976,929 B2 | 3/2015 | Wu et al. | |
| 9,019,307 B1 | 4/2015 | Grimm | |
| 9,044,602 B2 | 6/2015 | Kilby et al. | |
| 9,192,786 B2 | 11/2015 | Yan et al. | |
| 9,205,281 B2 | 12/2015 | Mazin | |
| 9,254,396 B2 | 2/2016 | Mihaylov | |
| 9,437,340 B2 | 9/2016 | Echner et al. | |
| 9,498,167 B2 | 11/2016 | Mostafavi et al. | |
| 9,731,148 B2 | 8/2017 | Olivera et al. | |
| 9,764,162 B1 | 9/2017 | Willcut et al. | |
| 9,820,700 B2 | 11/2017 | Mazin | |
| 9,956,429 B2 | 5/2018 | Holmes et al. | |
| 9,974,494 B2 | 5/2018 | Mostafavi et al. | |
| 10,327,716 B2 | 6/2019 | Mazin | |
| 10,456,600 B2 | 10/2019 | Owens et al. | |
| 10,674,983 B2* | 6/2020 | Black | A61B 6/50 |
| 10,688,320 B2 | 6/2020 | Voronenko et al. | |
| 10,695,586 B2 | 6/2020 | Harper et al. | |
| 10,959,686 B2 | 3/2021 | Mazin | |
| 11,033,757 B2 | 6/2021 | Voronenko et al. | |
| 11,309,072 B2 | 4/2022 | Carmi | |
| 2002/0137991 A1 | 9/2002 | Scarantino et al. | |
| 2002/0191734 A1 | 12/2002 | Kojima et al. | |
| 2003/0036700 A1 | 2/2003 | Weinberg | |
| 2003/0128801 A1 | 7/2003 | Eisenberg et al. | |
| 2003/0212325 A1 | 11/2003 | Cotrutz et al. | |
| 2003/0219098 A1 | 11/2003 | McNutt et al. | |
| 2004/0024300 A1 | 2/2004 | Graf | |
| 2004/0030246 A1 | 2/2004 | Townsend et al. | |
| 2004/0057557 A1 | 3/2004 | Nafstadius | |
| 2004/0068182 A1 | 4/2004 | Misra | |
| 2004/0079899 A1 | 4/2004 | Ma | |
| 2004/0096033 A1 | 5/2004 | Seppi et al. | |
| 2004/0120452 A1 | 6/2004 | Shapiro et al. | |
| 2004/0122308 A1 | 6/2004 | Ding | |
| 2004/0264640 A1 | 12/2004 | Myles | |
| 2005/0089135 A1 | 4/2005 | Toth et al. | |
| 2005/0109939 A1 | 5/2005 | Engler et al. | |
| 2005/0111621 A1 | 5/2005 | Riker et al. | |
| 2005/0111757 A1 | 5/2005 | Brackett et al. | |
| 2005/0113961 A1 | 5/2005 | Sabol et al. | |
| 2005/0197564 A1 | 9/2005 | Dempsey | |
| 2005/0201516 A1 | 9/2005 | Ruchala et al. | |
| 2005/0207531 A1* | 9/2005 | Dempsey | A61N 5/1031 378/65 |
| 2006/0002511 A1 | 1/2006 | Miller et al. | |
| 2006/0058637 A1 | 3/2006 | Sommer | |
| 2006/0078086 A1 | 4/2006 | Riley et al. | |
| 2006/0113482 A1 | 6/2006 | Pelizzari et al. | |

(56) References Cited

U.S. PATENT DOCUMENTS

| | | |
|---|---|---|
| 2006/0159220 A1 | 7/2006 | Heuscher |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2006/0241332 A1 | 10/2006 | Klein et al. |
| 2006/0293583 A1 | 12/2006 | Saracen et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0133749 A1 | 6/2007 | Mazin et al. |
| 2007/0265528 A1 | 11/2007 | Xu et al. |
| 2007/0297565 A1 | 12/2007 | Wofford et al. |
| 2008/0002811 A1 | 1/2008 | Allison |
| 2008/0031406 A1 | 2/2008 | Yan et al. |
| 2008/0071131 A1 | 3/2008 | Rietzel |
| 2008/0128631 A1 | 6/2008 | Suhami |
| 2008/0156993 A1 | 7/2008 | Weinberg et al. |
| 2008/0205588 A1 | 8/2008 | Kim |
| 2008/0230705 A1* | 9/2008 | Rousso .............. A61B 5/417 250/363.04 |
| 2008/0273659 A1 | 11/2008 | Guertin et al. |
| 2009/0116616 A1 | 5/2009 | Lu et al. |
| 2009/0117044 A1* | 5/2009 | Hengerer ........ G01R 33/56366 424/9.1 |
| 2009/0169082 A1 | 7/2009 | Mizuta et al. |
| 2009/0264728 A1 | 10/2009 | Fischer et al. |
| 2009/0296886 A1 | 12/2009 | Maltz et al. |
| 2010/0054411 A1 | 3/2010 | Nord et al. |
| 2010/0086183 A1 | 4/2010 | Vik et al. |
| 2010/0150309 A1 | 6/2010 | Nord et al. |
| 2011/0049377 A1 | 3/2011 | Morf et al. |
| 2011/0122997 A1 | 5/2011 | Lu et al. |
| 2011/0163238 A1* | 7/2011 | Teshigawara ........ G01T 1/2985 250/363.03 |
| 2011/0184749 A1 | 7/2011 | Stevens |
| 2011/0291015 A1 | 12/2011 | Mazin |
| 2012/0053961 A1 | 3/2012 | Wang et al. |
| 2012/0230464 A1 | 9/2012 | Ling et al. |
| 2012/0250971 A1 | 10/2012 | Holmes et al. |
| 2012/0292534 A1 | 11/2012 | Geneser et al. |
| 2012/0323599 A1 | 12/2012 | Bal et al. |
| 2013/0083004 A1 | 4/2013 | Nord et al. |
| 2013/0188856 A1 | 7/2013 | Adler, Jr. et al. |
| 2013/0216026 A1 | 8/2013 | Nord et al. |
| 2014/0005464 A1* | 1/2014 | Bharat ................ A61N 5/1031 600/1 |
| 2014/0093049 A1 | 4/2014 | Riley et al. |
| 2014/0126700 A1 | 5/2014 | Gertner et al. |
| 2014/0252227 A1* | 9/2014 | Sasai ................ G21K 1/046 250/307 |
| 2014/0270053 A1 | 9/2014 | Larson |
| 2014/0275704 A1 | 9/2014 | Zhang et al. |
| 2014/0336438 A1 | 11/2014 | Bharat et al. |
| 2015/0043709 A1 | 2/2015 | Shapiro et al. |
| 2015/0094519 A1 | 4/2015 | Kuusela et al. |
| 2015/0161338 A1 | 6/2015 | Scherrer et al. |
| 2015/0224342 A1 | 8/2015 | Baltes et al. |
| 2015/0251017 A1 | 9/2015 | De Crevoisier et al. |
| 2015/0360056 A1 | 12/2015 | Xing et al. |
| 2015/0367143 A1 | 12/2015 | Muraki et al. |
| 2016/0023019 A1 | 1/2016 | Filiberti et al. |
| 2016/0038767 A1 | 2/2016 | Wiersma et al. |
| 2016/0074541 A1* | 3/2016 | Zalutsky ............ A61K 51/1093 530/391.3 |
| 2016/0129282 A1 | 5/2016 | Yin et al. |
| 2016/0140300 A1 | 5/2016 | Purdie et al. |
| 2016/0193480 A1 | 7/2016 | Ribbing et al. |
| 2016/0361566 A1 | 12/2016 | Larkin et al. |
| 2016/0361568 A1 | 12/2016 | Chappelow et al. |
| 2017/0014642 A1 | 1/2017 | An et al. |
| 2017/0023494 A1 | 1/2017 | Yu et al. |
| 2017/0028220 A1 | 2/2017 | Schulte et al. |
| 2017/0087385 A1 | 3/2017 | Miettinen et al. |
| 2017/0095678 A1 | 4/2017 | Oster et al. |
| 2018/0133518 A1 | 5/2018 | Harper et al. |
| 2018/0345042 A1 | 12/2018 | Voronenko et al. |
| 2019/0054320 A1 | 2/2019 | Owens et al. |
| 2019/0381338 A1 | 12/2019 | Voronenko et al. |
| 2020/0121953 A1 | 4/2020 | Fredriksson |
| 2021/0196212 A1 | 7/2021 | Mazin |
| 2021/0236854 A1 | 8/2021 | Voronenko et al. |
| 2022/0001209 A1 | 1/2022 | Owens et al. |
| 2022/0126117 A1 | 4/2022 | Voronenko et al. |

FOREIGN PATENT DOCUMENTS

| | | |
|---|---|---|
| CN | 1960780 A | 5/2007 |
| CN | 101496018 A | 7/2009 |
| CN | 102068763 A | 5/2011 |
| CN | 102641561 A | 8/2012 |
| CN | 103180014 A | 6/2013 |
| CN | 103845068 A | 6/2014 |
| CN | 104284697 A | 1/2015 |
| CN | 105658279 A | 6/2016 |
| CN | 106563211 A | 4/2017 |
| EP | 0 212 135 B1 | 9/1991 |
| EP | 1 454 653 B1 | 9/2007 |
| EP | 2 072 081 A1 | 6/2009 |
| EP | 1 501 604 B1 | 12/2009 |
| EP | 1 898 234 B1 | 4/2010 |
| EP | 2 904 974 A1 | 8/2015 |
| EP | 2 990 078 A1 | 3/2016 |
| EP | 2 874 702 B1 | 9/2016 |
| EP | 3 175 886 B1 | 6/2018 |
| JP | 2007-502166 A | 2/2007 |
| JP | 2007-507246 A | 3/2007 |
| JP | 2009-160308 A | 7/2009 |
| JP | 2009-538195 A | 11/2009 |
| JP | 2012-035072 A | 2/2012 |
| JP | 2012-506734 A | 3/2012 |
| JP | 2013-059576 A | 4/2013 |
| JP | 2014-023741 A | 2/2014 |
| JP | 2014-503315 A | 2/2014 |
| JP | 2016-055161 A | 4/2016 |
| JP | 2016-168077 A | 9/2016 |
| WO | WO-00/59576 A1 | 10/2000 |
| WO | WO-03/076003 A2 | 9/2003 |
| WO | WO-03/076003 A3 | 9/2003 |
| WO | WO-2004/017832 A2 | 3/2004 |
| WO | WO-2004/017832 A3 | 3/2004 |
| WO | WO-2004/105574 A2 | 12/2004 |
| WO | WO-2004/105574 A3 | 12/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/031629 A1 | 4/2005 |
| WO | WO-2005/110495 A1 | 11/2005 |
| WO | WO-2007/082126 A2 | 7/2007 |
| WO | WO-2007/082126 A3 | 7/2007 |
| WO | WO-2008/011725 A1 | 1/2008 |
| WO | WO-2008/024463 A2 | 2/2008 |
| WO | WO-2008/024463 A3 | 2/2008 |
| WO | WO-2009/114117 A2 | 9/2009 |
| WO | WO-2009/114117 A3 | 9/2009 |
| WO | WO-2013/024380 A1 | 2/2013 |
| WO | WO-2013054788 A1 * | 4/2013 ........... A61N 5/1031 |
| WO | WO-2013/093852 A1 | 6/2013 |
| WO | WO-2016/023786 A1 | 2/2016 |
| WO | WO-2016/064750 A1 | 4/2016 |
| WO | WO-2017/081768 A1 | 5/2017 |
| WO | WO-2018/183748 A1 | 10/2018 |
| WO | WO-2018/237328 A1 | 12/2018 |

OTHER PUBLICATIONS

Adaptive Radiation Therapy: ISBN:9781439816356. 2011. CRC Press. X Allen Li (Ed.): 426 pages (cover only); URL: https://www.google.com/books/edition/Adaptive_Radiation_Therapy/9hEPvAlgPfMC (accessed Aug. 31, 2021).*

(56) References Cited

OTHER PUBLICATIONS

Etienne Croteau et al. "PET Metabolic Biomarkers for Cancer." Biomark Cancer. 2016; 8(Suppl 2): 61-69.*
Daniel Thorek. "Positron lymphography: multimodal, high-resolution, dynamic mapping and resection of lymph nodes after intradermal injection of 18F-FDG." J Nucl Med. Sep. 2012;53(9):1438-45.*
Kim et al. "18F-FDG PET/CT of Advanced Gastric Carcinoma and Association of HER2 Expression with Standardized Uptake Value." Asia Oceania J Nucl Med Biol, 2014; 2(1): 12-18.*
Kong et al. "Effect of Midtreatment PET/CT-Adapted Radiation Therapy With Concurrent Chemotherapy in Patients With Locally Advanced Non-Small-Cell Lung Cancer." JAMA Oncol. Oct. 2017; 3(10): 1358-1365. Published online Oct. 12, 2017. Prepublished online Jun. 1, 2017.*
Chen, X. et al. (2012). "Smoothing proximal gradient method for general structured sparse regression," The Annals of Applied Statistics 6:719-752.
Extended European Search Report dated Feb. 3, 2021, for EP Application No. 18 810 297.4, filed on May 30, 2018, 4 pages.
Hunt, M.A. et al. (2003). "Treatment Planning Considerations using IMRT," pp. 103-121.
International Search Report dated Apr. 23, 2020, for PCT Application No. PCT/US2020/013927, filed on Jan. 16, 2020, 3 pages.
International Search Report dated Dec. 1, 2020, for PCT Application No. PCT/US2020/040774, filed on Jul. 2, 2020, 4 pages.
Non-Final Office Action dated Dec. 6, 2019, for U.S. Appl. No. 15/993,325, filed May 30, 2018, 8 pages.
Non-Final Office Action dated Dec. 22, 2020, for U.S. Appl. No. 16/554,258, filed Aug. 28, 2019, 11 pages.
Non-Final Office Action dated Feb. 11, 2021, for U.S. Appl. No. 16/582,308, filed Sep. 25, 2019, 9 pages.
Notice of Allowance dated Apr. 20, 2020, for U.S. Appl. No. 15/993,325, filed May 30, 2018, 7 pages.
Written Opinion of the International Searching Authority dated Apr. 23. 2020, for PCT Application No. PCT/US2020/013927, filed on Jan. 16, 2020, 4 pages.
Written Opinion of the International Searching Authority dated Dec. 1, 2020, for PCT Application No. PCT/US2020/040774, filed on Jul. 2, 2020, 8 pages.
Akpati, H.C. et al. (2008). "Unified dosimetry index (UDI): A figure of merit for ranking treatment plans," J Appl Clin Med Phys. 9:99-108.
Alrowaili, Z.A. et al. (2015). "2D mapping of the MV photon fluence and 3D dose reconstruction in real time for quality assurance during radiotherapy treatment," J. Instrumentation IOP Science 10:P09019, 17 total pages.
ArcCHECK® & 3DVH (2016). Sun Nuclear, located at https://www.sunnuclear.com/solutions/patientqa/arccheck3dvh, retrieved on Jul. 31, 2019, 12 total pages.
Chang, J.Y. et al. (2008). "Image-guided radiation therapy for non-small cell lung cancer," J. Thorac Oncol. 3:177-186 (Abstract Only).
Chen, Q. et al. (2016). "SU-D-201-03: During-Treatment Delivery Monitoring System for TomoTherapy," Med. Phys. 43:3334, 1 total page.
Chen, Q. (2016) "During treatment delivery monitoring system for tomotherapy," Presentation, University of Virginia Health System, 16 total pages.
Dieterich, S. et al. (2003). "Skin respiratory motion tracking for stereotactic radiosurgery using the CyberKnife," *Elsevier Int'l Congress Series* 1256:130-136.
ECN Magazine (2016), "Magic plate radiation detector helps improve cancer radiotherapy," located at https://www.ecnmag.com/news/2016/03/magic-plate-radiation-detector-helps-improve-cancer-radiotherapy, retrieved on Jul. 31, 2019, 5 total pages.
Erdi, Y.E. (2007). "The use of PET for radiotherapy," *Curr. Medical Imaging Reviews* 3(1):3-16.
Extended European Search Report dated Mar. 31, 2017, for European Application No. 09 719 473.2, filed on Mar. 9, 2009, 8 pages.

Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Fan, Q. et al. (2012). "Emission Guided Radiation Therapy for Lung and Prostate Cancers: A Feasibility Study on a Digital Patient," *Med. Phys.* 39(11):7140-7152.
Final Office Action dated Aug. 15, 2012, for U.S. Appl. No. 13/209,275, filed Aug. 12, 2011, 8 pages.
Fredriksson (2013). "Robust optimization of radiation therapy accounting for geometric uncertainty," KTH Engin. Sciences, pp. 8-14.
Gibbons, J.P. (2004). "Dose calculation and verification for tomotherapy," 2004 ACMP Meeting, Scottsdale, AZ., 71 total pages.
Grau, C. et al. (2013). "Biology-guided adaptive radiotherapy (BiGART)—More than a vision?" Acta Oncol. 52:1243-1247.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
Henke, L.E. et al. (2016). "Online Adaptive Magnetic Resonance—Guided (OAMR)-Stereotactic Body Radiation Therapy for Abdominal Malignancies: Prospective Dosimetric Results From a Phase 1 Trial," Abstract No. 1139, Int'l J. Radiation Oncol. vol. 96, No. 2S, ePoster Sessions, pp. S222-S223.
International Search Report dated May 4, 2009, for PCT Application No. PCT/US2009/01500, filed on Mar. 9, 2009, 3 pages.
International Search Report dated Nov. 16, 2018, for PCT Application No. PCT/US2018/039104, filed on Jun. 22, 2018, 4 pages.
International Search Report dated Oct. 3, 2018, for PCT Application No. PCT/US2018/035188, filed on May 30, 2018, 4 pages.
International Search Report dated Oct. 3, 2018, for PCT Application No. PCT/US2018/043954, filed on Jul. 26, 2018, 3 pages.
Kak, A. et al. (1988). "Aliasing artifacts and noise in CT images," Principles of computerized tomographic imaging, pp. 177-201.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," *Physics in Med. Biol.* 46:943-966.
Keall, P.J. et al. (2001), "Motion adaptive x-ray therapy: a feasibility study," *Physics in Med. Biol.* 46:1-10.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (1993). "Tomotherapy: A new concept for the delivery of dynamic conformal radiotherapy," Med. Phys. 20:1709-1719.
Mazin, S.R. et al. (2010). "Emission-guided radiation therapy: Biologic targeting and adaptive treatment," Am. College of Radiology, pp. 989-990.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 8 pages.
Non-Final Office Action dated Sep. 19, 2013, for U.S. Appl. No. 13/895,255, filed May 15, 2013, 8 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated Oct. 5, 2017, for U.S. Appl. No. 14/951,194, filed Nov. 24, 2015, 11 pages.
Notice of Allowance dated Apr. 4, 2019, for U.S. Appl. No. 15/807,383, filed Nov. 8, 2017, 11 pages.

(56) References Cited

OTHER PUBLICATIONS

Notice of Allowance dated Jul. 25, 2019, for U.S. Appl. No. 16/046,746, filed Jul. 26, 2018, 8 pages.
Notice of Allowance dated Aug. 15, 2019, for U.S. Appl. No. 16/046,746, filed Jul. 26, 2018, 7 pages.
Oiivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," Am. Assoc. Phys. Med. 42:7153-7168.
Pyakuryal, A. et al. (2010). "A computational tool for the efficient analysis of dose-volume histograms for radiation therapy treatment plans," J Appl. Clin. Med. Phys. 11:137-157.
Rahmim, A. et al. (2009). "Four-dimensional (4d) image reconstruction strategies in dynamic pet: beyond conventional independent frame reconstruction," Medical physics 36:3654-3670.
Reader, A.J. et al. (2007). "Advances in pet image reconstruction," PET clinics 2:173-190.
Riederer, S.J. et al. (1978). "The noise power spectrum in computed x-ray tomography," Physics in medicine and biology 23:446.
ScandiDos (2019). Delta$^{4,}$ located at https://delta4family.com/products, retrieved on Jul. 31, 2019, 5 total pages.
Seppenwoolde, Y. et al. (2002). "Precise and real-time measurement of 3d tumor motion in lung due to breathing and heartbeat, measured during radiotherapy," International Journal of Radiation Oncology Biology Physics 53:822-834.
Written Opinion of the International Searching Authority dated May 4, 2009, for PCT Application No. PCT/US2009/01500, filed on Mar. 9, 2009, 5 pages.
Written Opinion of the International Searching Authority dated Nov. 16, 2018, for PCT Application No. PCT/US2018/039104, filed on Jun. 22, 2018, 6 pages.
Written Opinion of the International Searching Authority dated Oct. 3, 2018, for PCT Application No. PCT/US2018/035188, filed on May 30, 2018, 28 pages.
Written Opinion of the International Searching Authority dated Oct. 3, 2018, for PCT Application No. PCT/US2018/043954, filed on Jul. 26, 2018, 5 pages.
Varian Medical Systems (2019). MOBIUS3D, Varian oncology software products, located at https://www.varian.com/oncology./products/software/mobius3d, retrieved on Jul. 31, 2019, 3 total pages.
Yan, D. et al. (1997). "Adaptive radiation therapy," *Physics Med. Biol.* 42:123-132.
Yan, D. et al. (2016). "Selection of FDG Position Emission Tomography—Based Bioparametric Matrixes for Tumor Dose Response Mapping and Adaptive Dose Painting by Number," Abstract No. 102, Int'l J. Radiation Oncol. vol. 96, No. 2S, p. S46.
Bao, Q. et al. (2010). "Estimation of the minimum detectable activity of preclinical PET imaging systems with an analytical method," Med. Phys. 37:6070-6083.
Extended European Search Report dated Mar. 15, 2021, for EP Application No. 18 837 615.6, filed on Jul. 26, 2018, 8 pages.
Extended European Search Report dated Jun. 14, 2021, for EP Application No. 18 821 003.3, filed on Jun. 22, 2018, 5 pages.
Final Office Action dated Jul. 14, 2021, for U.S. Appl. No. 16/582,308, filed on Sep. 25, 2019, 8 pages.
Hoeben, B.A.W. et al. (2013). "Molecular PET imaging for biology-guided adaptive radiotherapy of head and neck cancer," Acta Oncologia 52:1257-1271.
Thorwarth, D. et al. (2010). "Physical radiotherapy treatment planning based on functional PET/CT data," Radiotherapy Oncology, pp. 317-324.
Non-Final Office Action dated Jun. 8, 2022, for U.S. Appl. No. 16/582,308, filed Sep. 25, 2019, 9 pages.
Non-Final Office Action dated Jul. 5, 2022, for U.S. Appl. No. 17/203,532, filed Mar. 16, 2021, 13 pages.
Non-Final Office Action dated Aug. 30, 2022, for U.S. Appl. No. 17/235,812, filed Apr. 20, 2021, 8 pages.
Zhang, H. et al. (2002). Progress in the Physics of Tumor Radiation Therapy, Beijing Medical University, China Union Medical University Joint Press, p. 164 (with English translation).
Zhao, H. et al. (2015). Practical Imaging Diagnosis, University Press, Aug. 2015, p. 167 (with English translation).

\* cited by examiner

| ROI | Volume (% or cc) | Volume Max (Gy) | Max Point Dose (Gy) |
|---|---|---|---|
| PTV | > 95% | 50 | 107 % of prescription |
| Spinal Cord | < 0.25 cc | 22.5 | 30 Gy |
| Lung | < 1000 cc | 12.5 | - |
| Skin | < 10 cc | 30 | 32 Gy |
| Great Vessels | < 10 cc | 47 | 105 % of prescription |

FIG. 3A

| PQI | Mathematical Formula | Use or meaning |
|---|---|---|
| Dvv, where vv is percent of a ROI volume or absolute ROI volume in cc (cm3).<br>Example 1: D95% = 45 Gy<br>Example 2: D10cc = 20Gy | Dose level for a ROI that corresponds to the 'vv' Volume level on the ROI DVH.<br>Example 1: 95% of the ROI volume will get at least 45 Gy.<br>Example 2: 10 cc of ROI will get at least 20 Gy.. | vv (%) or (cc) of ROI volume will have at least dose D (Gy). |
| $V_D$, where dose D is absolute dose (Gy) or percent of the prescription dose (%).<br>Example 1: V50%<br>Example 2: V20Gy | % or cc of ROI volume that receives at least dose D.<br>Example 1: volume receiving 50 % of the prescription dose.<br>Example 2: %Volume of ROI receiving 20 Gy. | V (% or cc) that will receive at least dose D, where dose D is in either Gy or % of the prescription dose |
| Conformity Index (CI) | V100/TV | Measures the PTV volume that is covered by the prescription isodose. |
| Homogeneity Index (HI1) | Dxx/Dyy, where xx is a small number, and yy = 100-xx. For example D5/D95 or D2/D98. | Measures the "hot" spot range in the target volume. |
| Homogeneity Index (HI2) | (D2-D98)/Dp, where D100 is the prescription isodose. | Measures the % range of dose variation in the target relative to the prescription dose. |

FIG. 3B

| | | |
|---|---|---|
| Dose gradient index (DGI1) | V50/V100 | Measures the dose gradient near the target. Smaller values indicate higher dose gradient |
| Dose gradient index (DGI2) | R50 - R100 (cm) | Distance in cm between the 50% isodose and 100% isodose |
| Dmax (Gy) | Maximum dose | Maximum dose for an OAR or PTV. |
| Dmin (Gy) | Minimum dose | Minimum dose for a PTV. |
| Combined | A sum or quadrature form of a combination of PQIs, for example: $$PQI_{combined} = \sqrt{\sum_i w_i \cdot P_i^2}$$ | Overall combined quality score of the treatment plan |

FIG. 3B (Cont.)

| Prescription parameter | Original Plan Prescription | PQI MAPO |
|---|---|---|
| PTV coverage = V90%Rx | > 99% | > 95% |
| PTV conformity index | < 1.2 | < 1.5 |
| PTV heterogeneity index | > 0.70 | > 0.55 |
| Lung V20 | < 10 % | < 15 % |
| Lung D50 | < 13 Gy | < 13.5 Gy |

| Clinical parameter change | PQI | PQI on day of simulation | PQI on day of first treatment |
|---|---|---|---|
| Distance between the center pf the PTV and spinal cord reduced by 3 mm | Spinal cord max dose | 29 Gy | 31 Gy |
| PTV volume increased by 5% | PTV D95 | 50 Gy | 46 Gy |
| PTV volume increased by 5% | PTV CI | 1.2 | 1.7 |
| PTV shape change by 10% | PTV HI1 | 1.3 | 1.6 |
| OAR volume increased by 5% | OAR Dmax | 30 Gy | 37 Gy |

SYSTEMS AND METHODS FOR BIOLOGICAL ADAPTIVE RADIOTHERAPY

CROSS-REFERENCE TO RELATED APPLICATIONS

This application claims priority to U.S. Provisional Patent Application No. 62/523,691, filed Jun. 22, 2017, the disclosure of which is hereby incorporated by reference in its entirety.

TECHNICAL FIELD

Disclosed herein are systems and methods for adapting and/or updating radiotherapy treatment plans and/or radiation delivery during a treatment session based on biological and/or physiological data and/or anatomical data extracted or calculated from imaging data acquired in real-time (e.g., at the time of treatment). Also disclosed herein are methods for evaluating treatment plans based on imaging data acquired in real-time.

BACKGROUND

Radiotherapy treatment planning usually takes place in advance of a treatment session (e.g., weeks, days, hours). As such, a variety of parameters may have changed in the time period between the treatment planning session and the treatment session, and these changes may affect the dose that is delivered to the patient (i.e., insufficient radiation to target regions, elevated irradiation of non-target regions, etc.). Typically, patient imaging scans just before a treatment session provide information about any structural or geometric changes to the patient and/or target region. For example, anatomical images from a CT or MRI scan performed on the day of treatment and just prior to the treatment session may be used to shift the radiation fluence in accordance with a positional shift of the patient and/or tumor(s), enlarge or shrink the size of irradiation regions to correspond with size changes in the patient and/or tumor(s), and/or adjust the contour of irradiation regions to correspond with changes in the shape of the patient and/or tumor(s). Modifying treatment plans and/or radiation delivery based on recently-acquired data may facilitate more efficient and targeted radiation therapy.

Accordingly, it may be desirable to develop additional methods for updating radiotherapy treatment plans to reflect changes in the patient and/or target region(s).

SUMMARY

Described herein are methods for adapting and/or updating radiotherapy treatment plans based on biological and/or physiological data extracted or calculated from imaging data acquired during a treatment session. In some variations, biological activity and/or physiological data of a patient may comprise a tracer uptake value (e.g., standard uptake value or SUV), PET tracer kinetics, tissue metabolism data (e.g., spectroscopic imaging data, magnetic resonance spectroscopic imaging data), osteogenic activity data, oxygenation data, genetic expression data (e.g., human growth father receptor type 2 (HER2) expression), free fatty acid uptake data, blood flow data, vascularity data, morphological shifts in tumor geometry (e.g., speculation), and/or lymphatic activity data, etc. Based upon these biological activity and/or physiological data, updating or adapting a treatment plan may comprise updating or modifying a dosimetric objective of one or more target regions or other regions of interest (ROI), geometry of one or more target regions or other regions of interest (ROI), number of total treatment sessions, duration of treatment sessions, and/or fractionation pattern over multiple treatment sessions, etc. Biological activity and/or physiological data may be acquired using any imaging modality, for example, functional imaging modalities such as PET imaging, MRI imaging, single-photon emission computed tomography or SPECT imaging, magnetic particle imaging or MPI. Optionally, structural imaging modalities such as X-ray imaging, CT imaging, ultrasound imaging may also be used to update or adapt treatment plans. Alternatively or additionally, treatment plans may be updated or adapted based on dose delivery data from previous treatment sessions or fractions.

Also disclosed herein are methods for evaluating a treatment plan based on real-time acquired imaging data. These methods may be used for determining whether to proceed with a prescribed treatment plan based on patient and/or system parameters at the time of the treatment session. In some variations, decisions on whether to proceed with a treatment plan may depend on various clinical parameters such as geometrical changes (e.g., volume and/or shape changes) of one or more patient target regions, geometrical changes in one or more radiation-sensitive regions (e.g., organs-at-risk or OARs), changes in the relative distances between the targets and the OARs, changes in patient external contour such as dimension or shape, standard uptake values (SUVs), changes in textural features of patient target regions (e.g. cluster shade, cluster prominence, cellular homogeneity), and whether such factors are within a prescribed range at the time of (or just prior to) treatment. The prescribed range may be determined based on data acquired during a diagnostic imaging session, treatment planning session, and/or at the start of a treatment session (e.g., during a patient prescan), and/or may be a known or widely accepted range of normal activity. Decisions on whether to proceed with a treatment plan may also depend on changes in treatment plan quality (e.g., which may be quantified by treatment plan index (PQI) values) and/or dose-volume histogram (DVH) curves. In some variations, PQI values and/or dose-volume histograms may be calculated based on biological activity and/or physiological data and/or anatomical data acquired at the time of (and/or just prior to) treatment.

Biological activity data may include physiological data. Examples of biological activity data of a region of interest may include oxygenation and/or hypoxia levels, blood perfusion level, expression of certain genes (e.g. by measuring cellular protein-binding), immune response activity, cell death and/or necrosis, fractal dimension shifts (e.g. changes in microvascular permeability), tumor growth vectors, or standard uptake value(s) of tracer(s) correlated with specific biological functions (e.g. metabolic activity or bone remodeling). Anatomical data may include structural information such as the shape, size, location (e.g., absolute location and/or relative location to other anatomical regions, and/or markers or fiducials, and/or imaging system and/or radiation treatment system coordinates) of a region of interest and/or patient.

One variation of a method for adapting a radiotherapy treatment plan may comprise measuring biological activity data of a patient region using one or more PET detectors during a radiation treatment session, comparing the measured biological activity data with an initial biological activity range to calculate a change in the biological activity data and updating a radiotherapy treatment plan based on the calculated changes in the biological activity data. The initial biological activity range may be measured during the radiation treatment session prior to measuring the biological activity data, and/or may be measured during a previous radiation treatment session. Updating the radiotherapy treatment plan may comprise changing a dosimetric objective of one or more patient target regions, and/or changing the geometry of one or more patient target regions and/or dose-shaping structures. Updating the radiotherapy treatment plan may comprise changing a fractionation pattern over multiple treatment sessions. The radiotherapy treatment plan may comprise an initial number of treatment sessions and updating the treatment plan may comprise changing the number of treatment sessions from the initial number of treatment sessions. The radiotherapy treatment plan may comprise an initial treatment session duration and updating the treatment plan may comprise changing the treatment session duration from the initial treatment session duration. Measuring biological activity data may comprise measuring a standard update value (SUV) of a PET tracer of the patient region.

One or more PET tracers may be used in any of the methods described herein. Examples of PET tracers may include, but not limited to, 18F-FDG, 18F-NaF, 18FHX4, 18FFAZA, 18FFMISO, radiolabeled 5F7 anti-HER2 nanobody labeled with 18F, 11C-Palmitate and 14-(R,S)-18F-fluoro-6-thiaheptadecanoic acid, 15O-Water, 13N-Ammonia, 82Rb-Rubidium, 18F-flurorothymidine, 68Ga-Gallium, 68Ge-Germanium, F18-Fluciclovine, Ga68-DOTATATE, C11-Choline, Ga68-PSMA, F18-PyL(PSMA), PD-L1, 13N-nitrogen, 11C-methionine, 18F-fluoroerythronitroimidazole, 3'-Aza-2'-[18F]fluorofolic acid, N-succinimidyl 3-((4-(4-(18)F-fluorobutyl)-1H-1,2,3-triazol-1-yl)methyl)-5-(guanidinomethyl)benzoate radiolabeled 5F7 antibody, 1-(2'-deoxy-2'-[18F]fluoroarabinofuranosyl) cytosine (18F-FAC), and F18-Fluciclovine.

Biological activity data may comprise tissue metabolism data, and/or osteogenic activity, and/or oxygenation levels, and/or human growth factor receptor type 2 (HER2) genetic expression, and/or free fatty acid uptake, and/or physiological activity data. Physiological activity data may comprise blood flow data, and/or vascularity of the patient region, and/or morphological shifts in spiculation of a tumor region in the patient region, and/or lymphatic activity data. Measuring biological activity data may comprise quantitatively measuring PET tracer kinetics in the patient target region. A radiotherapy treatment plan may comprise a target dose distribution and updating the treatment plan may comprise changing the target dose distribution. In some variations, the updated treatment plan may be used for a future radiation treatment session. Measuring biological activity data of a patient target region may further comprise acquiring a functional image of the patient target region using magnetic resonance imaging, laser scanning fluorescence imaging, ultrasound imaging, magnetic particle imaging, or single-photon emission computed tomography. Measuring biological activity data of a patient region may comprise providing a PET tracer to the patient and measuring positron emission data from a patient target region. In some variations, the PET tracer may be a hypoxia PET tracer, such as [18F]HX4, [18F]FAZA, and [18F]FMISO and measuring positron emission data may comprise measuring hypoxia PET tracer uptake values across the patient target region. Updating the radiotherapy treatment plan may comprise increasing a radiation dose of the radiotherapy treatment plan to patient target regions with hypoxia PET tracer uptake values that exceed a threshold.

In some variations, the PET tracer may comprise a HER2 PET tracer such as 5F7 Anti-HER2 nanobody labeled with 18F (18F-RL-I-5F7) and 18F-SFB, and measuring positron emission data may comprise measuring HER2 PET tracer uptake values across the patient target region. Updating the radiotherapy treatment plan may comprise increasing a radiation dose of the radiotherapy treatment plan to patient target regions with HER2 PET tracer uptake values that exceed an upper threshold. The method may optionally comprise measuring HER2 PET tracer uptake values of patient regions outside of the target region and identifying patient regions outside of the target region having HER2 PET tracer uptake values that exceed the upper threshold. Updating the radiotherapy treatment plan may comprise changing the dose distribution to include the identified patient regions for radiation dose delivery. Alternatively or additionally, the PET tracer may comprise a HER2 PET tracer such as 5F7 Anti-HER2 nanobody labeled with 18F (18F-RL-I-5F7) and 18F-SFB, and measuring positron emission data may comprise measuring HER2 PET tracer uptake values across the patient target region. Updating the radiotherapy treatment plan may comprise decreasing a radiation dose of the radiotherapy treatment plan to patient target regions with HER2 PET tracer uptake values that exceed an upper threshold.

A method for adapting a radiotherapy treatment plan may additionally or alternatively comprise calculating a plan quality index (PQI) value of the radiotherapy treatment plan based on the measured biological activity data, comparing the calculated PQI value with a pre-determined range of PQI values, and updating the radiotherapy treatment plan if the calculated PQI value is not within the pre-determined range of PQI values. The radiotherapy treatment plan may not be updated if the calculated PQI value is within the pre-determined range of PQI values. In some variations, the method may comprise displaying a notification if the calculated PQI value is not within the pre-determined range of PQI values. The pre-determined range of PQI values may be a range of clinician-approved PQI values.

In some variations, the radiotherapy treatment plan is updated if the measured biological activity data is not within the initial biological activity range. The method may comprise displaying a notification if the measured biological activity data is not within the initial biological activity range. The initial biological activity range may be a clinician-approved biological activity range, and/or the initial biological activity range may be calculated based on a range of clinician-approved PQI values for the radiotherapy treatment plan. In some variations, the initial biological activity range may be calculated based on clinician-approved bounded DVH for the radiotherapy treatment plan. Updating the radiotherapy treatment plan may comprise adjusting a range of acceptable plan quality index (PQI) values and/or biological activity values to formulate an updated treatment plan having a range of acceptable PQI values and/or a range of acceptable biological activity values that includes the measured biological activity data. The pre-determined bounded DVH may be calculated based on one or more of the following: dose delivered to the patient target region in one or more previous treatment session, clinician-approved dose delivery uncertainty, maximum dose level and/or minimum dose level.

Some variations of a method for adapting a radiotherapy treatment plan may alternatively or additionally comprise calculating a dose volume histogram (DVH) for a patient target region based on the radiotherapy treatment plan and the measured biological activity data, comparing the calculated DVH with a pre-determined bounded DVH, and updating the radiotherapy treatment plan if the calculated DVH is not within the pre-determined bounded DVH.

Also disclosed herein are methods for generating biological activity ranges acceptable for treatment. One variation of a method may comprise determining a range of acceptable plan quality index (PQI) values for a treatment plan and calculating a range of biological activity values that corresponds with the range of PQI values. A method for radiation treatment may comprise determining a range of acceptable PQI values for a treatment plan, measuring biological activity data of a patient region using one or more PET detectors during a radiation treatment session, comparing the measured biological activity data with the calculated range of biological activity values to determine whether the measured biological activity data is within the calculated range, and applying radiation to the patient region if the measured biological activity data is within the calculated range of biological activity values. If the measured biological activity data is not within the calculated range of biological activity, the radiotherapy treatment plan may be updated based on the measured biological activity data.

Disclosed herein are methods for generating a plan quality index (PQI) range acceptable for treatment. One variation of a method may comprise determining a range of acceptable biological activity values for a treatment plan and calculating a range of PQI values that corresponds with the range of acceptable biological activity values. The calculated range of biological activity values may be transmitted to a radiation therapy system and/or may be displayed to a clinician.

Described herein are methods for radiotherapy treatment. One variation of a method for radiotherapy may comprise measuring biological activity data of a patient region using one or more PET detectors, comparing the measured biological activity data of the patient region with a pre-determined biological activity range, updating a treatment plan if the measured biological activity data is not within the pre-determined biological activity range, and applying radiation to the patient region based on the updated treatment plan. The pre-determined biological activity range may be a clinician-approved biological activity range. Measuring biological activity data of the patient region may comprise measuring hypoxic PET tracer uptake values across the patient region, and applying radiation comprises applying radiation such that a radiation dose to regions with higher hypoxic PET tracer uptake values is greater than a radiation dose to regions with lower hypoxic PET tracer uptake values.

Also described herein are methods for calculating bounded dose-volume histograms (DVH) for evaluating a treatment plan. One example of a method may comprise generating a plurality of images $X'_{1, 2, 3, \ldots, j}$ based on an acquired patient image X, where a patient target volume (PTV) is located at j different positions within a radiation-firing zone (RFZ) of a patient, calculating a dose $D_j$ for each of the images $X'_{1, 2, 3, \ldots, j}$ by multiplying a dose calculation matrix A with a radiation-firing matrix P and $X'_j$ ($D_j = A \cdot P \cdot X'_j$), plotting a dose-volume histogram (DVH) curve for each dose $D_j$ to generate a family of j DVH curves, where the DVH curve for each dose $D_j$ may represent a volume fraction for each dose value, and generating a minimum boundary curve (min-DVH curve) and a maximum boundary curve (max-DVH curve) of the family of DVH curves. The min-DVH curve may comprise a first series of points that represent a minimum volume fraction for each dose value of the family of DVH curves, and the max-DVH curve may comprise a second series of points that represent a maximum volume fraction for each dose value. Generating a plurality of images $X'_j$ may comprise simulating j three-dimensional rigid shifts of the PTV within the RFZ for each of the images $X'_j$. Alternatively or additionally, generating a plurality of images $X'_j$ may comprise changing intensity values of the PTV in each image $X'_j$ to simulate a range of standard uptake values (SUVs). In some variations, changing intensity values of the PTV may comprise increasing the intensity values of the PTV to be +25% over a nominal intensity value and/or decreasing the intensity values of the PTV to be −25% under a nominal intensity value. The acquired image X may be a PET image or may be a CT image. Generating a min-DVH curve may comprise fitting the first series of points to a first curve, and generating a max-DVH curve may comprise fitting the second series of points to a second curve. The dose calculation matrix A and the radiation-firing matrix P may be derived based on the acquired patient image X prior to a treatment session. In one variation, the patient image X may be a first patient image, and the method may further comprise acquiring a second patient image Y, calculating a dose $D_Y$ by multiplying the dose calculation matrix A with the radiation-firing matrix P and Y ($D_Y = A \cdot P \cdot Y$), and plotting a DVH curve corresponding to second patient image Y. The method may further comprise generating a notification if the DVH curve of the second patient image Y is not bounded between the min-DVH curve and the max-DVH curve. The notification may be a visual notification and/or an audio notification. The DVH curve corresponding to the second patient image Y may represent a volume fraction over the PTV for each dose value and/or the DVH curve corresponding to the second patient image Y may represent a volume fraction over an organ-at-risk (OAR) for each dose value. Methods may also comprise displaying the min-DVH curve and the max-DVH curve on a display or monitor/screen. In some variations, the display may be a display of a radiation therapy system. Plotting a DVH curve for each dose $D_j$ may comprise plotting a volume fraction over the PTV for each dose value to generate a family of j DVH curves for the PTV. Alternatively or additionally, some methods may comprise plotting a DVH curve for each dose $D_j$ by plotting a volume fraction over an organ-at-risk (OAR) for each dose value to generate a family of j DVH curves for the OAR, and the min-DVH curve may be an OAR min-DVH curve and the max-DVH curve may be an OAR max-DVH curve. The DVH curve corresponding to the second image Y may be an OAR DVH curve, and the method may further comprise generating a notification if the DVH curve of the OAR in the second patient image Y exceeds the max-DVH curve of the OAR.

Also described herein are methods for evaluating a radiotherapy treatment plan. One variation of a method may comprise acquiring imaging data x of a patient, calculating a radiation dose $D_x$ and plotting a dose-volume histogram (DVH) based on the acquired imaging data and a radiation-firing matrix P ($D_x = A \cdot P \cdot x$), and generating a notification that is displayed on a monitor if the DVH is not within a range define by a minimum-DVH curve and a maximum-DVH curve. Optionally, some methods may comprise generating a notification that is displayed on the monitor if the radiation dose distribution $D_x$ is not within a dose distribution range defined by a minimum dose threshold and a maximum dose threshold. The imaging data may be PET imaging data and/or CT imaging data. Some variations may comprise calculating a plan quality index (PQI) based on the acquired imaging data x, and generating a notification that is displayed on a monitor if the PQI is not within a PQI range defined by a minimum PQI threshold and a maximum PQI threshold.

BRIEF DESCRIPTION OF THE DRAWINGS

FIG. 3A depicts a table of examples of prescribed radiation doses to various regions of interest.

FIG. 3B depicts a table of examples of plan quality indices (PQI).

DETAILED DESCRIPTION

Disclosed herein are systems and methods for adapting and/or updating radiotherapy treatment plans based on biological and/or physiological data and/or anatomical data extracted or calculated from imaging data acquired in real-time (e.g., during a treatment session). Functional imaging data acquired at the time of radiation treatment is used to modify a treatment plan and/or dose delivery instructions to provide a prescribed dose distribution to patient target regions. Also disclosed herein are methods for evaluating treatment plans based on imaging data acquired in real-time.

Systems

Figure 1A:
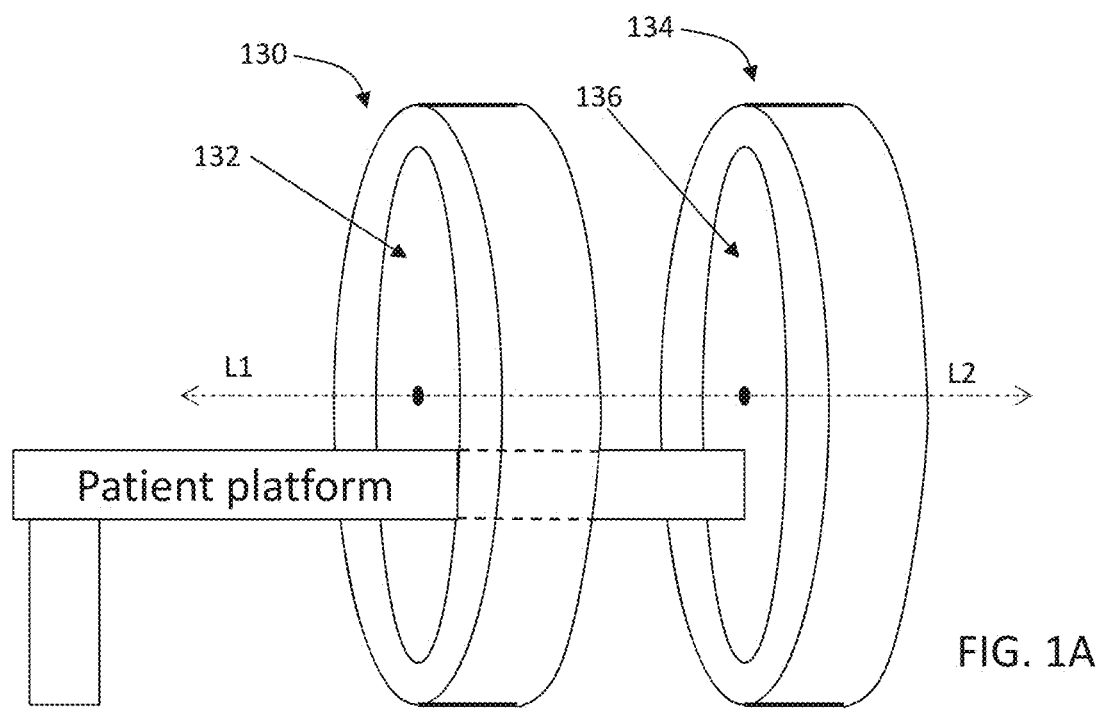
FIG. 1A depicts one variation of a system for adaptive radiotherapy.
Figure 1B:
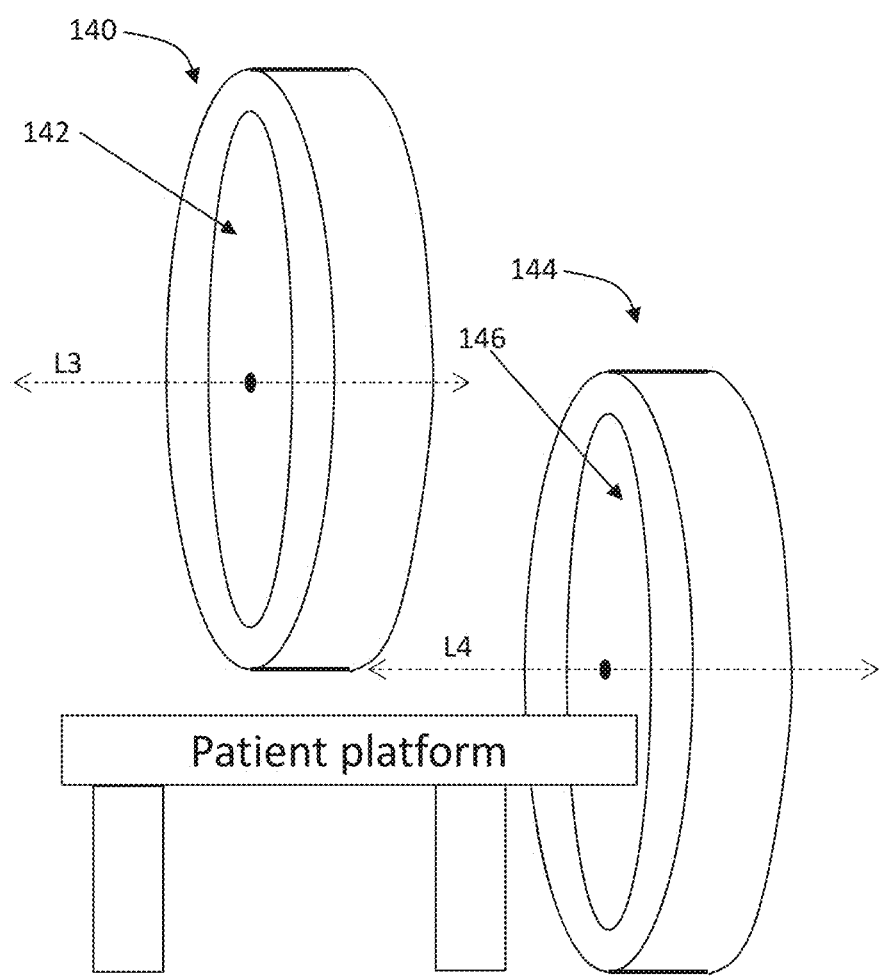
FIG. 1B depicts another variation of a system for adaptive radiotherapy.
Figure 1C:
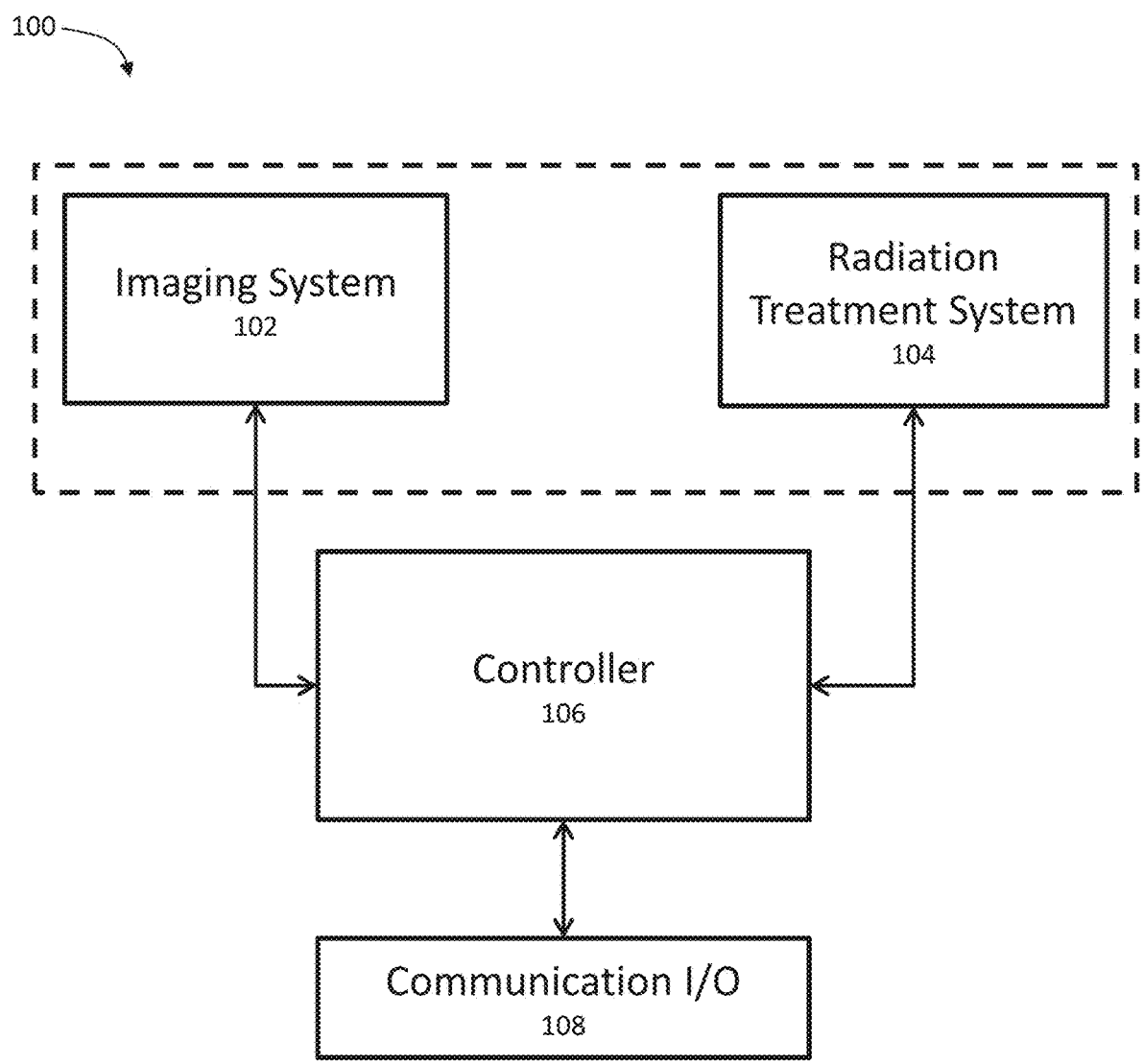
FIGS. 1C-1D depict examples of systems for adaptive radiotherapy.
Figure 1D:
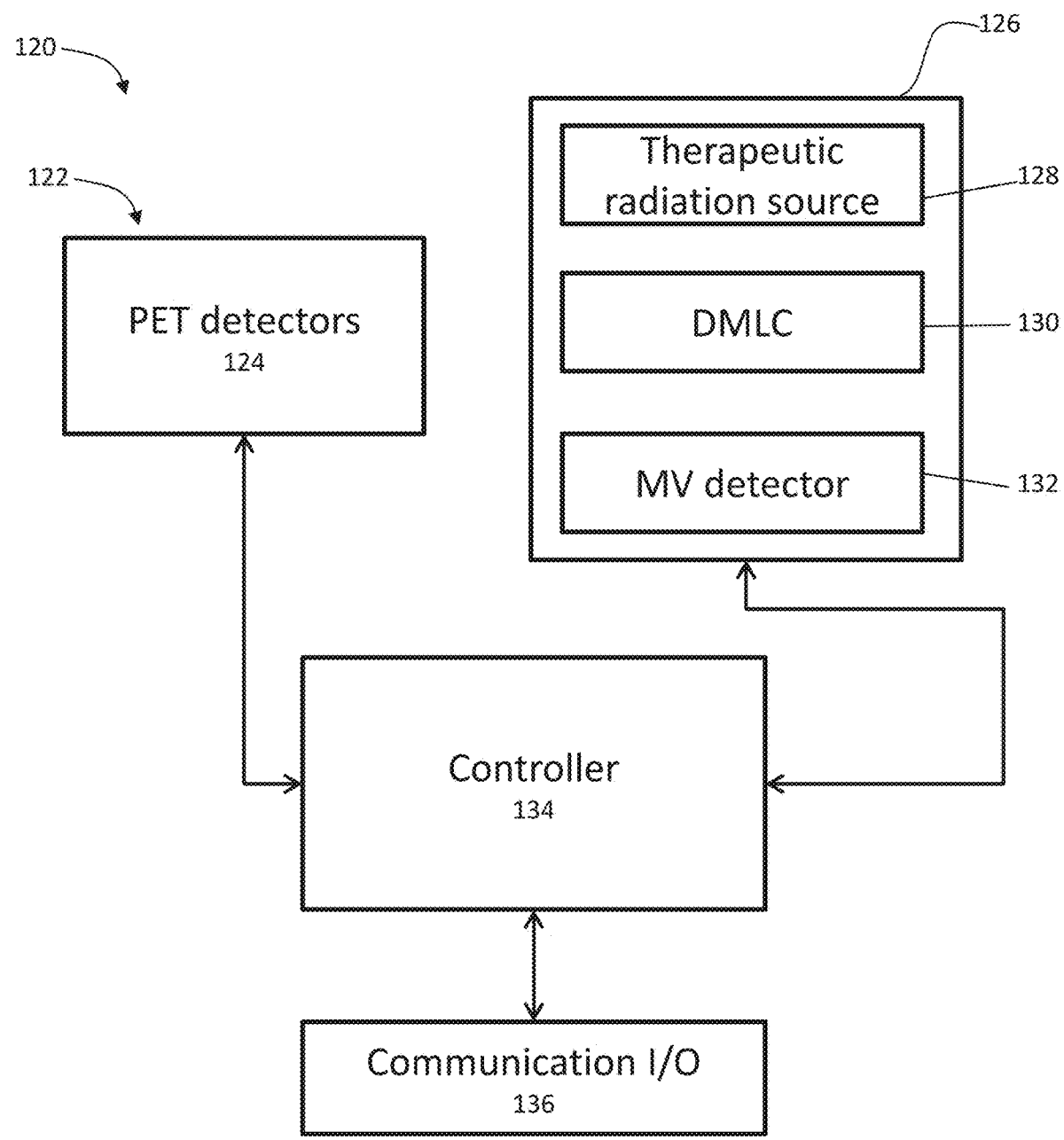

FIG. 1A schematically depicts one variation of a system that may be used for adaptive radiation therapy. System 100 may comprise an imaging system 102, a radiation treatment system 104, a controller 106 in communication with the imaging system and the radiation treatment system, and a communication interface 108. The imaging system 102 and the radiation treatment system 104 may be arranged such that a patient may be readily positioned in the radiation treatment system immediately after patient image data has been acquired by the imaging system. For example, the imaging system 102 and the radiation treatment system 104 may be located in the same facility or building, and/or the same room or bunker, and/or may be mounted on the same chassis or gantry. In some variations, the imaging system and the radiation treatment system may be arranged such that the patient region of the imaging system is aligned with the patient region of the treatment system. FIG. 1A depicts one example of an imaging system 130 with a patient region 132 and a treatment system 134 with a patient region 136 where the longitudinal axes L1, L2 of the patient regions of the patient regions 132, 136 respectively are aligned or collinear. Alternatively, the imaging system and the radiation treatment system may be arranged such that the patient regions of each of the imaging system and the radiation treatment system are not aligned, but are adjacent to each other. FIG. 1B depicts one example of an imaging system 140 with a patient region 142 and a treatment system 144 with a patient region 146 where the longitudinal axes L3, L4 of the patient regions 142, 146 respectively are not collinear, and may instead be parallel to each other, or at an angle to each other. Imaging data acquired by the imaging system 102 at the time of treatment (e.g., just before the activation of the radiation treatment system and/or during the application of therapeutic radiation to the patient) may be transmitted to the controller 106, where a controller processor may be configured to extract biological activity data (and/or physiological and/or anatomical data) of the patient from the acquired imaging data. The controller may also be configured to calculate the predicted quality and/or efficacy of a treatment plan in light of the recently-acquired biological activity data. Depending on the magnitude and/or characteristics of any changes in biological activity levels and/or physiological data, the controller may then evaluate whether radiation treatment of the patient should proceed or continue based on the pre-determined treatment plan(s), and/or whether the treatment plan(s) should be updated and/or adapted. Alternatively or additionally, these calculated quantities may also be presented to a clinician via communication interface 108 for evaluation and/or treatment plan approval. The radiation treatment system 104 may be configured to adapt therapeutic radiation beams to the patient based on the imaging data acquired at the time of treatment, as well as the evaluation and/or approval of a clinician.

The imaging system 102 may be configured to acquire imaging data using any one or more imaging modalities, including functional and/or anatomical imaging modalities, as long as the imaging system is capable of acquiring data during a treatment session (i.e., in real-time). The imaging system 102 may comprise one or more PET detectors, and/or X-ray detectors (e.g., kV or MV detectors), and/or MRI sensors, ultrasound detectors, etc. Imaging data from the imaging system 102 may provide biological activity and/or physiological and/or anatomical data relating to the patient's body and/or the one or more regions of interest (ROI) or target regions. Some imaging systems may acquire data relating to the uptake of various types of tracers in the patient's body. For example, a patient may be injected with a tracer (e.g., PET tracer, X-ray contrast agent, and the like), and the imaging system may acquire data regarding the accumulation of the tracer (qualitatively and/or quantitatively). The tracer accumulation location, size and shape of the tracer accumulation volumes, as well as tracer kinetics may provide an indication of various biological activity levels and/or physiological phenomena in the patient. For example, cellular metabolism levels and the presence (or absence) of oxygen in a tissue region may be calculated from the amount and/or rate of tracer uptake, as indicated by the intensity of the imaging data. Changes in the expression of genes that have been tagged with the tracers may also be calculated by measuring changes in image intensity. The size and shape of tumor regions may be determined at least in part by the size and shape of regions of tracer uptake that exceed a pre-determined threshold. While some imaging systems may be configured to acquire imaging data at any time point, regardless of the activation state of the radiation treatment system (e.g., regardless of whether the therapeutic radiation source is activated), other imaging systems may be configured to acquire imaging data when the therapeutic radiation source of the radiation treatment system is not activated (e.g., not firing a radiation beam). For example, an imaging system comprising one or more X-ray detectors may acquire imaging data between therapeutic radiation beam pulses, and/or when the therapeutic radiation source is not activated (due to the effects of X-ray scatter from a high-energy radiation source). An imaging system comprising one or more PET detectors may acquire PET data between therapeutic radiation beam pulses, and/or at the start of a treatment session before the first therapeutic radiation pulse and/or at the end of the treatment session after the last therapeutic radiation pulse. In contrast, an imaging system that comprises one or more MRI sensors may acquire imaging data regardless of whether the therapeutic radiation source is activated and/or applying a radiation beam pulse.

The radiation treatment system 104 may be configured to direct radiation to the patient according to a treatment plan, which may be updated or adapted based on imaging data (e.g., biological activity data and/or anatomical data calculated from this imaging data) acquired by the imaging system. The radiation treatment system may comprise a therapeutic radiation source (e.g., an MV X-ray radiation source such as a linac, a radioactive isotope source such as a Cobalt-60 source, or a particle beam source such as a cyclotron), one or more beam-shaping structures that may be configured to direct or limit the therapeutic radiation beam, and a motion system configured to rapidly move the therapeutic radiation source and the beam-shaping structures to various firing positions around the patient area. In one variation, a radiation treatment system may comprise a MV X-ray radiation source and a dynamic multi-leaf collimator disposed in the beam path of the radiation source, both mounted on a motion system comprising a movable gantry. The gantry may be a rotatable gantry, such as a circular gantry or a L-arm or C-arm gantry, and/or an articulated robotic arm movable and/or rotatable about the patient area. The gantry may optionally be a continuously rotating gantry. The motion system may be configured to move the radiation source and beam-shaping structures from one firing position to another firing position in less than about 10 seconds, for example, less than about 5 seconds, less than about 3 seconds, less than about 2 seconds, less than about 1 second, less than about 0.5 second, less than about 0.25 second, etc. The dynamic multi-leaf collimator may comprise a plurality of leaves, each leaf attached to a leaf actuation mechanism that moves the leaf to a location designated by the controller. The dynamic multi-leaf collimator may be a binary multi-leaf collimator or a 2-D multi-leaf collimator. Other beam-shaping devices or collimators may also be used, for example, radial collimators that generate circular fields. The leaf actuation mechanism may be configured to rapidly move the leaf from one position to another position before the radiation source fires the next beam pulse. For example, in a binary multi-leaf collimator, the leaf actuation mechanism may be configured to transition a leaf from a closed position to an open position (and vice versa) in less than about 5 seconds, e.g., less than about 3 seconds, less than about 2 seconds, less than about 1 second, less than about 0.5 second, less than about 0.75 second, less than about 0.5 second, less than about 0.3 second, less than about 0.25 second, less than about 0.2 second, less than about 0.1 second, etc. The combination of a rapid-movement motion system and rapid-transitioning dynamic multi-leaf collimator may help reduce the latency between the acquisition of imaging data and the application of a radiation beam pulse based on biological activity data extracted from the imaging data. The position of the leaves at a particular firing location (e.g., location around a patient area where the therapeutic radiation source may be positioned when firing radiation beams) may be determined based on a treatment plan. A treatment plan may be calculated in a treatment planning session and may be updated just prior or during a treatment session based on the biological activity data and/or physiological data and/or anatomical data extracted from imaging data acquired on the day of treatment (e.g., in real-time). In some variations, the processor of the controller may generate a set of multi-leaf collimator commands that drive the movement and location of each leaf at each firing location so that the radiation beam has an irradiation shape that adheres to the treatment plan. This computation may also be referred to as segmentation of the treatment plan (and/or generating a fluence map of the treatment plan) to generate a sinogram or radiation-firing matrix. A sinogram may represent a set of multi-leaf collimator commands that maps the position of each leaf of the multi-leaf collimator at each firing position or angle. Some sinograms may map a multi-leaf collimator leaf pattern (e.g., the cumulative beam shape as a result of aggregating individual leaf positions) to each firing position or angle. As the treatment plan is updated or adapted based on biological activity data and/or physiological data and/or anatomical data acquired by the imaging system, the leaf instructions may change or adapt to account for any changes in biological activity levels and/or physiological phenomena. In some variations, the dynamic multi-leaf collimator may be configured to change the positions of one or more leaves while the therapeutic radiation source is moved to the next firing position. Concurrent leaf movement and radiation source movement may help to reduce the latency between the detection of biological activity data and the application of radiation, which may help the radiation treatment system to irradiate tumor regions before they move substantially.

Furthermore, the configuration of the multi-leaf collimator (e.g., the positions of the leaves at various firing locations) may be updated as the treatment plan is updated based on imaging data acquired on the day of treatment (e.g., at the time of treatment, during treatment).

The controller 106 may be in communication with the imaging system 102 and the radiation treatment system 104 such that acquired imaging data may be processed (e.g., to extract or calculate biological activity data and/or physiological data and/or anatomical data) and the delivery of therapeutic radiation beams may be adjusted based on the acquired imaging data. The controller 106 may comprise one or more processors (e.g., a central processing unit) and one or more memories. A controller memory may store data relating to one or more treatment plans, treatment plan parameters (e.g., plan quality indices, dose-volume histograms, etc.), previously-collected imaging data (e.g., from a diagnostic imaging session), real-time imaging data (e.g., acquired on the day of a treatment session, at the time of treatment), extracted biological activity and/or anatomical data, radiation treatment system commands and instructions, dynamic models and algorithms used for treatment plan adaptation, user-implemented programs, and the like. The controller 106 may receive imaging data and imaging component feedback (e.g., status of image detectors or sensors, calibration data, etc.) from the imaging system 102, and may also transmit imaging commands (e.g., activation of any X-ray source, and/or activation of the image detectors or sensors, adjustments to detector gain and/or sensitivity levels, positioning of the imaging system relative to the patient and/or radiation treatment system, etc.) to the imaging system. The controller 106 may receive data from the various components of the radiation treatment system and may transmit commands to the radiation treatment system. For example, the radiation treatment system may comprise a motion system (e.g., gantry), a therapeutic radiation source (e.g., linac) and beam-shaping device (e.g., dynamic MLC) mounted on the motion system, and a radiation detector (e.g., MV detector) mounted on the motion system. The controller 106 may receive positional and/or speed data from the motion system, positional and/or radiation beam generation data from the radiation source, leaf-configuration data from the beam-shaping device, and/or more generally, operating status, calibration data, error indicators, and the like. The controller 106 may transmit MLC commands, gantry rotation/motion commands, linac pulse instructions, etc., where these commands and instructions may be generated based on a combination of treatment plans, previously-acquired images, real-time acquired imaging data, biological activity and/or physiological data of the patient, and/or the state of the radiation treatment system.

The controller 106 may be in communication with a display via communication interface 108, which may project a graphical user interface (GUI) that provides information to the user regarding treatment plans, imaging data, biological activity and/or physiological data, potential updates to the treatment plan based on imaging data, patient identification, patient status, system status, treatment session progress, dose delivery status, etc. The GUI may also provide a menu of commands for user selection, as well as a programming interface so that the user may enter a predetermined set of machine instructions and parameters. For example, the display may present one or more visual indicators that represent real-time patient biological activity and/or physiological data, the effect of this data on the efficacy of the current treatment plan (e.g., plan quality index or PQI, dose volume histogram or DVH, if radiation were to be delivered according to the current treatment plan with the current level of biological and/or physiological activity), and allow the clinician to decide whether to proceed with the current treatment plan, modify the treatment plan, or suspend the treatment session. In some variations, the GUI on the display may include bounded DVH curves, PQI values, and/or any treatment plan evaluation metric which have been calculated during treatment planning (e.g., based on biological and/or physiological data derived from planning images, such as planning CT and/or PET images). These DVH curves, PQI values, and/or any treatment plan evaluation metric previously approved by a clinician. DVH curves, PQI values, and/or any treatment plan evaluation metrics may be generated using real-time acquired patient biological activity and/or physiological data at the time of treatment, and displayed simultaneously with the same metrics that were calculated during treatment planning. For example, one or more DVH curves (e.g., for PTV and/or OAR) calculated based on biological and/or physiological data extracted from imaging data acquired at the time of treatment may be overlaid, or super-imposed over, the bounded DVH curves generated by the treatment planning system. The display may also present additional and/or alternative treatment plans based on the biological activity and/or physiological data of the patient, in accordance with one or more of the methods described herein. In some variations, the GUI on the display may include visual notifications as to whether treatment plan metrics calculated based on real-time imaging data are within pre-approved ranges (e.g., PASS), and/or outside pre-approved ranges (e.g., FAIL). Optionally, some variations may comprise additional tiers of notifications, for example, indicating various degrees to adherence to the treatment plan. For example, some variations may comprise a notification indicating that the variance of the calculated treatment plan metric(s) is/are within an acceptable tolerance (e.g., PASS WITHIN TOLERANCE) and/or a notification indicating that the variance of the calculated treatment metric(s) is/are outside of an acceptable tolerance (e.g., PASS WITH EXCEPTIONS). Optionally, when treatment plan metrics calculated based on the real-time imaging data are outside pre-approved ranges, treatment plan adaptation recommends may be provided in the GUI. The information presented on the display may help the clinician to determine the best course of action, given the state of the patient at the time of treatment. Alternatively or additionally, notifications may comprise one or more auditory signals or sounds generated by a speaker, where each type or tier of notification may have a different sound.

FIG. 1B depicts one variation of a system for adaptive radiotherapy. System 120 may comprise an imaging system 122 comprising one or more PET detectors 124, a radiation treatment system 126 comprising a therapeutic radiation source 128 (e.g., a MV X-ray source such as a linac), a dynamic MLC or DMLC 130, and an MV detector 132. The system 120 may also comprise a controller 134 in communication with the imaging system and the radiation treatment system 126 and a communication interface 136. The radiation emission assembly may be mounted on a movable gantry, such a rotatable gantry. In some variations, the rotatable gantry may be a continuously-rotatable circular gantry. Optionally, the imaging system 122 may also be mounted on the movable gantry. PET data (e.g., one or more individual positron annihilation emission paths) acquired by the one or more PET detectors 124 may be transmitted to the controller 134, which may be stored in controller memory and/or processed according to any of the methods described herein. The controller 134 may calculate and/or extract biological activity and/or physiological data from the PET data, which may optionally be presented to the clinician. The radiation treatment system 126 may move the therapeutic radiation source 128, change the DMLC leaf configuration, and acquire data from the MV detector in accordance with commands from the controller 134. In some variations, the gantry may be configured to rotate at about 40 RPM or more, e.g., about 60 RPM, about 70 RPM. The DMLC 130 may comprise leaf actuation mechanisms that change leaf positions within the time interval where the gantry is moving the radiation emission assembly from one firing position to another. For example, the DMLC 130 may comprise a leaf actuation mechanism that is configured to move a leaf from a fully closed position to a fully open position in less than about 10 ms. In some variations, a circular gantry that rotates with a frequency f having n firing positions may have a DMLC transition time that is less than 0.7*(f/n) seconds. For example, a circular gantry that rotates with a frequency f of about 1 Hz, having n=100 firing positions, may have a DMLC transition time of about 7 ms. A DMLC may comprise a leaf actuation mechanism comprising a pneumatic cylinder and one or more springs, which may provide sufficient motive force to change leaf position in the time interval between firing positions. Additional details and examples of multi-leaf collimator leaf actuation mechanisms, as well as radiation treatments systems are provided in U.S. patent application Ser. No. 15/179,823, filed Jun. 10, 2016 and U.S. Patent Application No. 62/422,404, filed Nov. 15, 2016, which are hereby incorporated by reference in their entirety.

Methods

Adaptive Radiotherapy

A method for adapting radiation therapy based on biological activity and/or physiological data may comprise acquiring imaging data in real-time (e.g., at the time of and/or during treatment), extracting biological activity and/or physiological data from the imaging data, determining whether a previously-generated treatment plan may be delivered based on the extracted biological activity and/or physiological data, and updating or adapting the treatment plan according to the biological activity and/or physiological data. Imaging data may not be limited to full-resolution, high contrast, and/or high signal-to-noise ratio (SNR) images, but may include images that may have lower resolution, lower contrast, and/or lower SNR. In some variations, imaging data may include a partial PET image, a partial MRI image, and/or a partial CT image etc. For example, a partial PET image may comprise one or more positron annihilation emission paths (e.g., a line of response defined by a pair of coincident photons emitted by a positron annihilation event), a partial MRI image may comprise one or more individual lines of k-space (e.g., that are sub-samplings in k-space) in the Fourier domain, and a partial CT image may comprise one or more 2-D projection X-ray images. Determining whether a previously-generated treatment plan continues to be clinically appropriate in light of the biological activity and/or physiological data may include comparing those data values with previously-approved data values (which comparison may be performed by a pre-programmed controller or processor) and/or calculating the efficacy of the current treatment plan based on current data values. In some variations, the system may display the extracted biological activity and/or physiological activity, treatment plan quality parameters, and/or related thresholds to a clinician.

In some variations, biological and/or physiological data extracted from imaging data acquired at the time of treatment (such as data calculated from a PET prescan acquired before the therapeutic radiation source is activated) may be used to determine whether the treatment session can proceed with the current treatment plan (i.e., "GO" or "NO GO"). If it is determined that the current treatment plan is no longer appropriate for delivery, then the system may adapt and/or update the plan according to the biological and/or physiological data. In one example, a DVH curve and/or one or more PQI(s) may be calculated based on the current treatment plan and the current (e.g., real-time acquired) biological and/or physiological data. That is, the system may calculate the radiation dose delivered (e.g., DVH curve and/or one or more PQI metrics) if treatment were to proceed with the current treatment plan, in light of the acquired biological and/or physiological data. The calculated DVH curve and/or one or more PQI values may be compared with the DVH curve and/or PQI values calculated based on the treatment plan and the treatment planning image (e.g., planning CT and/or PET image). The radiation therapy system may be configured to provide multiple levels or tiers of notifications to a clinician or technician that indicate the level of similarity between the calculated DVH and/or PQI value(s) and the treatment plan DVH and/or PQI value(s). For example, a clinician and/or radiation therapy system may specify that in order for radiation to be delivered according to a prescribed treatment plan, the target region coverage must be at least 95% coverage with a 1% tolerance during the prescription of radiation (meaning 94% coverage is acceptable but needs review and requires clinician evaluation and approval). Biological and/or physiological data from a PET prescan acquired at the start of a treatment session (i.e., before therapeutic radiation source beam on) may be used to calculate target region coverage based on the prescribed treatment plan. Depending on the calculated target region coverage, the radiation therapy system may provide a notification (e.g., a visual notification via a GUI presented on a display, and/or auditory signals) of whether to proceed with delivering radiation according to the prescribed treatment plan (i.e., "GO"), or if the session should be terminated until the treatment plan is updated or (re-)calculated based on the up-to-date biological and/or physiological data (i.e., "NO GO"). Some variations may generate notifications that indicate one or more of the statuses summarized in Table 1 below.

TABLE 1

Examples of Status Notifications

| Status | Calculated target region coverage | Interpretation |
| --- | --- | --- |
| PASS/GO | 97% ± 1% (i.e., range of expected coverage between 96% and 98%) | Both the nominal delivery and the variance are within the bounds of 95% or more coverage. No treatment plan adaptation is required. |

TABLE 1-continued

Examples of Status Notifications

| Status | Calculated target region coverage | Interpretation |
|---|---|---|
| PASS WITHIN TOLERANCE | 95% ± 1% (i.e., range of expected coverage between 94% and 96%) | Both the nominal delivery and the variance are within the bounds of 95% or more coverage. No treatment plan adaptation is required. Optional clinician review and approval. |
| PASS WITH EXCEPTIONS | 95% ± 3% (i.e., range of expected coverage between 92% and 98%) | The nominal delivery are within the bounds of 95% coverage, but a portion of the variance is out of bounds (e.g., 92%-94%). Treatment plan adaption optional. Optional clinician review to determine whether to proceed with radiation delivery or adapt the treatment plan. Changes to biological activity may cause the target region coverage to be out of bounds. |
| FAIL/NO GO | 58% ± 5% (i.e., range of expected coverage between 53% and 63%) | Neither the nominal delivery or the variance are within the bounds of 95% or more coverage. Cannot proceed with delivering radiation according to current treatment plan. Treatment plan adaptation recommended or required by a clinician. |

DVHs and/or PQI(s) deemed to be acceptable for treatment plan delivery may vary by clinician and/or clinic. In one variation, a DVH and/or PQI(s) is considered a PASS/GO if 95% of all DVH points above 10% of Prescription Dose on the nominal DVHs of OARs and the BgROI are within the Minimum and Maximum DVH points on the two bounds of the Bounded DVH (within a ±1° % tolerance). The testing threshold, percent passing, and comparison tolerances may be configuration variables that may be adjusted during commissioning of the system. Other criteria for proceeding to a GO status may optionally include a check to ensure that the mean activity in the target region (e.g., a PET-avid region such as a tumor) is above a minimum level configured in the system. For instance, a check that the mean SUV in the target region is above a minimum level as specified by the system and/or clinician and/or treatment plan.

In some variations, if it is determined that a treatment plan is no longer deliverable because the delivered radiation would not be within pre-approved ranges or boundaries, the radiation therapy system may provide recommendations or guidance to the clinician and/or technician as to the type of treatment plan adaptation. Some variations may comprise a biological adaptive trigger that includes one or more treatment plan quality and/or delivery criteria or metrics and a corresponding type (or types) of adaptation if the calculated dose delivered by a treatment plan (e.g., calculated based on real-time imaging data, biological and/or physiological data) does not meet those quality and/or delivery criteria. For example, a clinician or clinic may set a first treatment objective of a target region coverage level of at least 95%, with a 1% tolerance during radiation delivery (e.g., meaning 94% coverage may be acceptable for delivery, and may optionally be subject to clinician review and approval), and a second treatment objective of a maximum mean dose (MMD) value to a near-field OAR of less than 1500 cGy maximum mean dose, with a 200 cGy tolerance over the entire structure (e.g., meaning 1500 cGy to 1700 cGy maximum mean dose may be acceptable for delivery, and may optionally be subject to clinician review and approval). If a treatment plan falls short of either of these objectives or delivery metrics on the day of treatment (i.e., based on imaging data from a prescan), the system may indicate that delivery is a "FAIL/NO GO" with an optional indication of the type of adaptation recommended for the treatment plan, e.g., "FAIL WITH RECOMMENDATION".

For example, if the target coverage is below the 94% tolerance point but above 90%, and the MMD valued to a near-field OAR is within objectives, the system may generate a notification indicating "FAIL WITH RECOMMENDATION". The recommendation may be to adapt the treatment plan to provide a dose escalation to increase coverage as long as the near-field OAR does not violate its MMD constraint. For example, if the target coverage is 93% with a MMD value to OAR of 1300 cGy, the system may generate a notification indicating "FAIL WITH RECOMMENDATION". The recommendation may be to adapt the treatment plan to provide a uniform dose escalation to the target region to achieve an updated target coverage of 95% and 1450 cGy.

In another example, if the MMD value to a near-field OAR is above the 1700 cGy tolerance level and the target coverage is above the 95% objective, the system may generate a notification indicating "FAIL WITH RECOMMENDATION". The recommendation may be to adapt the treatment plan to provide a dose reduction to decrease the MMD coverage as long as the target coverage remains above the 95% objective. For example, if the target coverage is 99% with a MMD value to OAR of 1950 cGy, the system may generate a notification indicating "FAIL WITH RECOMMENDATION". The recommendation may be to adapt the treatment plan to provide a uniform dose reduction to the target structure to achieve an updated target coverage of 95% and 1450 cGy. Alternatively or additionally, other objectives and/or radiation delivery metrics may trigger updates or adaptations to a treatment plan. For example, a treatment plan may be updated in response to changes in dose shaping, structure modification, changing firing angles for a given position, or similar adjustments to the intended delivery.

Figure 2A:
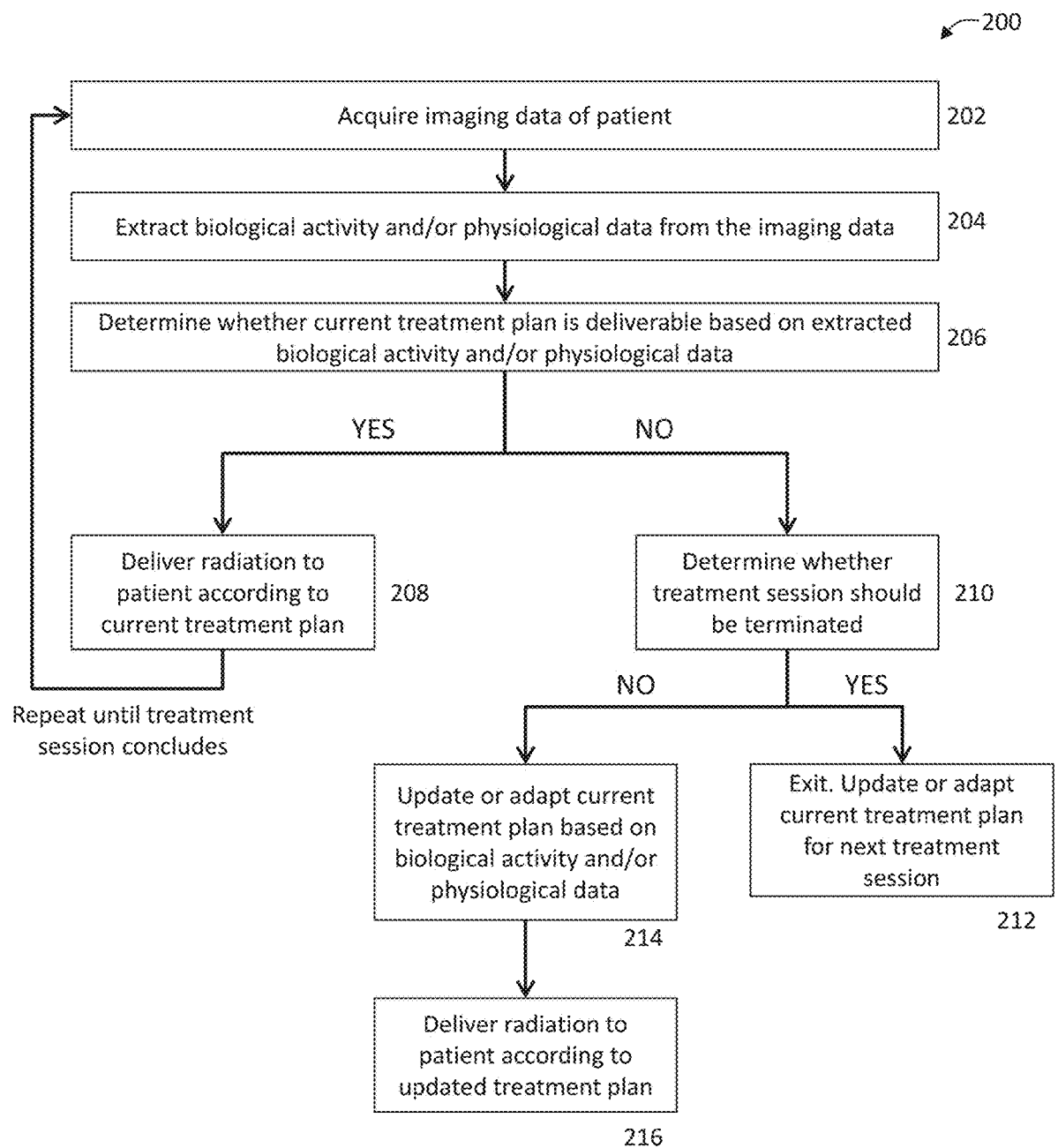
FIG. 2A depicts a flowchart representing one variation of a method for adaptive radiotherapy.

FIG. 2A depicts a flowchart representation of a method for adapting radiation therapy based on biological activity and/or physiological data. This example is described in the context of using PET tracers, but it should be understood that any types of tracer and/or imaging modalities may be used. Method 200 may comprise acquiring 202 imaging data of the patient at the start of the treatment session and/or during the treatment session, and extracting 204 biological activity and/or physiological data from the acquired imaging data. Imaging data may include, for example, positron annihilation emission paths emitted from a PET tracer injected into the patient prior to the treatment session. Biological activity and/or physiological data may include a tracer uptake value (e.g., standard uptake value or SUV), PET tracer kinetics, tissue metabolism data, osteogenic activity data, oxygenation data, genetic expression data (e.g., human growth father receptor type 2 (HER2) expression), free fatty acid uptake data, blood flow data, vascularity data, morphological shifts in tumor geometry (e.g., spiculation), and/or lymphatic activity data, etc. The SUV of a particular 2D or 3D region in an image may be calculated from imaging data by multiplying the intensity of the pixels or voxels in that region calibrated to represent a known tissue tracer activity (typically, in mCi/g) divided by the injected dose (typically, in mCi) per patient body weight (typically, in kg) at a specific time since the original injection (the time of the scan acquisition).

$$SUV(t) = c_{img}(t)/(ID/BW)$$

where $c_{img}(t)$ is the calibrated tissue tracer activity as a function of time that has elapsed since the original injection, where ID is the injected dose at the time of the original injection and BW is the body weight of the patient at the time of the original injection.

A variety of alternate derived values may be calculated additionally for of a volume of interest such as mean SUV of a 3D volume, minimums, maximums, standard deviations, multi-region SUV ratios, and/or SUV correlated to lean body mass ($SUV_{LMB}$) or body surface area ($SUV_{BSA}$) instead of whole body mass (sometimes referred to as $SUV_{BW}$). PET tracer kinetics may be calculated by monitoring the changes in pixel intensities over time as well as calculating derived activity values over time. That is, biological activity and/or physiological values derived from PET tracer kinetics and SUV measurements (e.g., mean uptake values, changes in SUV, etc.) may optionally be calculated as a function of time. Different types of PET tracers may target different types of cellular markers (e.g., proteins, genes, etc.), and measuring PET tracer kinetics may provide an indication of the changes in the tracer-tagged cellular markers. For example, changes in tissue metabolism, and/or aerobic and anaerobic glycolysis, and/or glucose consumption or metabolism of a region of interest may be measured by injecting with 18-F Fluorodeoxyglucose (FDG), measuring the tracer activity level (e.g. changes in SUV) in a given defined target region over the course of a lengthy treatment window (for example, 30 minutes) and calculating slope value K representing the net uptake rate of entry into the tumor with the following formula:

$$K = K_1 * (k_3/(k_2+k_3))$$

where $K_1$ is the rate of the PET tracer entering into the tumor tissue from the blood where $k_3/(k_2+k_3)$ is the fraction of the tracer in the tumor that is no longer moving in or out of the defined target region where $k_3$ is the no longer moving tracer activity and $k_2$ is the tracer activity continuing to move. In some variations, measuring the metabolism of a tumor region by measuring FDG PET data may comprise using a gradient of $SUV_{max}$ to delineate between the tumor tissue and non-tumor tissue, for example, using a gradient of about 30-50% $SUV_{max}$. A threshold may be set at a value along the gradient, which may identify or delineate a region of elevated SUV levels. Alternatively or additionally, the ratio of tumor or lesion glycolysis (LG) to normal tissue glycolysis (NTG) may be used for adapting the treatment plan. LG may be calculated by multiplying the metabolic tumor volume (MTV) by the mean of the SUV ($SUV_{mean}$) of the MTV, and NTG may be calculated by multiplying the OAR volume by $SUV_{mean}$ of the OAR volume.

Other types of tracers may be used to measure different biological mechanisms and/or physiological and/or biological activity levels. For example, a 13N-nitrogen tracer may be used in the patient to monitor regional pulmonary function (RPF) and/or the aeration of blood that contains the tracer. This may provide an indication of whether blood aeration is within a normal or expected range, as well as whether blood is flowing through ventilated regions of the lungs. Measuring 13N-nitrogen tracer kinetics may also provide information about blood flow to non-ventilated regions of the lungs (i.e., blood that has been diverted or shunted away from ventilated lung regions). The net flow rate of aerated blood may be calculated by calculating the tracer kinetics of a target region. For example, calculating net tracer kinetics (e.g., net tracer flow rate) may comprise using a multi-compartment model to calculate the difference between flow rates of aerated tracer (e.g., tracer present in aerated blood that has dispersed or diffused) and shunt tracer or non-aerated tracer (e.g., tracer present in non-aerated blood or non-ventilated tissue such as alveoli that has been perfused with fluid). The net tracer flow rate may be compared with expected tracer flow rate data (e.g., collected in a previous diagnostic or treatment session) to help determine whether treatment plan adaption may be appropriate. For example, if the net tracer flow rate of a region is less than the expected tracer flow rate (e.g., as calculated during a previous treatment session), the treatment plan may be modified to permit a higher dose to be delivered to that region. A lower net tracer flow rate may indicate improved or robust pulmonary function and/or blood flow, and therefore, that target region may be able to tolerate increased levels of radiation. A higher net tracer flow rate may indicate lessened or ineffective pulmonary function and/or blood flow, and therefore, that target region may be sensitive or less tolerant of radiation (e.g., may be more susceptible to lung collapse and more likely to cause increases in pulmonary perfusion).

In another example, changes in the rates of DNA synthesis and/or tumor-cell proliferation between treatment sessions may be measured by using a 18F-fluorothymidine tracer. A 11C-methoionine tracer may also be used to measure changes in the rates of protein synthesis and/or tumor-cell proliferation between treatment sessions. The difference in SUV of a tumor region (e.g., $SUV_{diff}$) may be measured by subtracting the SUV of voxels in a region of interest in the current treatment session from the SUV of voxels in a previous treatment session. Changes in tumor region hypoxia may be measured using a 18F-fluoromisonidazole (e.g., FMISO, FETNIM) and/or a 18F-fluoroazomycinarabinoside tracer (e.g., FETNIM). A gradient of $SUV_{max}$ method may be used to delineate between the tumor tissue and non-tumor tissue, for example, using a gradient of about 30-50% $SUV_{max}$. A threshold may be set at a value along the gradient, which may identify or delineate region(s) of elevated SUV levels, and therefore, region(s) of increased hypoxia. Changes in folate receptor density between treatment sessions may be measured using a 3'-Aza-2'-[18F] fluorofolic acid tracer. The difference in SUV of an ovarian tumor region (e.g., $SUV_{diff}$) may be measured by subtracting the SUV of voxels in a region of interest in the current treatment session from the SUV of voxels in a previous treatment session. Levels of in HER2 genetic expression (HER2GE) may be measured using a N-succinimidyl 3-((4-(4-(18)F-fluorobutyl)-1H-1,2,3-triazol-1-yl)methyl)-5-(guanidinomethyl)benzoate radiolabeled 5F7 antibody. HER2 expression levels, which may be represented by the average SUV ($SUV_{mean\_total}$) of the volume-of-interest (VOI), may be calculated by multiplying the volume of the VOI by the mean of the SUV ($SUV_{mean}$) of the tumor volume. Alternatively or additionally, changes in HER2 expression levels between treatment sessions may be represented by the difference in SUV of the VOI (e.g., $SUV_{diff}$), which may be calculated by subtracting the SUV of voxels in the VOI in the current treatment session from the SUV of voxels in a previous treatment session or scan.

Optionally, biological activity and/or physiological data may be calculated based on spectroscopic imaging data. For example, spectroscopic imaging may be used to calculate the spatial distribution of metabolite concentrations in one or more patient regions (e.g., any regions of interest including OARs, PTVs, etc.). In some variations, magnetic resonance (MR) spectroscopic image data may be acquired at each treatment session and compared with MR spectroscopic image data from previous treatment session(s) and/or a diagnostic imaging session. The treatment plan and/or radiation delivery may be modified such that tumor regions that have increased levels of metabolites may be irradiated with higher levels of radiation. Conversely, if metabolite levels in the tumor regions have decreased, the treatment plan and/or radiation delivery may be modified such the dose delivered to these tumor regions is reduced.

Some variations may also comprise calculating and/or extracting anatomical data, for example, size and location of any target regions, bone structures, irradiation-avoidance regions, patient weight, etc.

Method 200 may further comprise determining 206 whether a current treatment plan is deliverable based on the extracted biological activity and/or physiological data. Treatment plans are generally developed based on previously-acquired patient data (e.g., anatomical, biological activity and/or physiological data), and if any patient parameters have changed from the initial data acquisition session and the treatment session, the treatment plan may need to be updated or re-calculated in order to attain clinical treatment goals. Determining whether a treatment plan may be considered deliverable at the time of treatment may comprise evaluating the treatment plan based on the newly acquired imaging data and/or extracted biological and/or physiological data, calculating the expected delivered dose to the one or more target regions in the patient, and determining whether the expected delivered dose is within pre-determined dose ranges and/or is in accordance with a desired dose distribution. For example, a treatment plan may be considered deliverable if the expected delivered dose to an irradiation-target region exceeds a lower threshold (e.g., minimum boundary) and the expected delivered dose to an irradiation-avoidance region does not exceed an upper threshold (e.g., maximum boundary). In some variations, the controller may make the determination whether to proceed with a radiotherapy treatment plan based on data values that have been previously-approved by a clinician. For example, one or more of DVH curves and/or PQI(s) may be calculated during treatment planning, and ranges of these (e.g., bounded DVH curves, ranges of PQI values) may be reviewed and approved by a clinician. Alternatively or additionally, the determination of whether to proceed with a radiation treatment may be made by a clinician, with information about biological, physiological activity levels, treatment plan efficiency, dose distribution, etc. provided by the controller. As described above, in some variations, a GUI rendered on a display (e.g., a monitor) may provide a visual and/or audible notification of whether the current treatment plan is deliverable (i.e., whether the current treatment plan would deliver radiation within ranges that have been previously-approved). For example, the GUI may provide one or more of the following notifications: PASS/GO, and/or FAIL/NO GO, and/or PASS WITHIN TOLERANCE, and/or PASS WITH EXCEPTIONS, and/or, FAIL WITH RECOMMENDATION. Some systems may be configured to provide two tiers of notifications (e.g., PASS/GO, and FAIL/NO GO), three tiers of notifications (e.g., PASS/GO, PASS WITHIN TOLERANCE or PASS WITH EXCEPTIONS, and FAIL/NO GO), four tiers of notifications (e.g., PASS/GO, PASS WITHIN TOLERANCE, PASS WITH EXCEPTIONS, and FAIL/NO GO), or with the five tiers of notifications described above. A clinician and/or clinic may select the number of types or tiers of notifications desired, and may decide to proceed or cease treatment in accordance with, or contrary to, the generated notifications.

If it is determined that the treatment session may proceed 208 with the current treatment plan, the controller may generate a set of system instructions/commands and transmit them to the radiation emission assembly for radiation delivery to the patient. In some variations, this may include generating a fluence map based on the treatment plan, and segmenting the fluence map into DMLC leaf patterns or a sinogram. Steps 202-206 may be repeated until the treatment session concludes (as specified by the treatment plan and/or clinician command and/or patient command). If it is determined that the treatment session should not proceed with the current treatment plan, method 200 may comprise determining 210 whether the treatment session should be terminated. For example, the acquired biological activity and/or physiological data may indicate that the patient is unable to sustain any radiation exposure, and/or that the regions of interest have dramatically changed from the treatment planning session, and/or that the patient did not comply with pre-treatment protocols (e.g. ate sugary food immediately prior to the treatment session making the patient's PET image invalid when using 18-F FDG), and/or that the planned radiation exposure may no longer provide adequate treatment (e.g. tumor became hypoxic and resistant to radiation treatment) and adapting the plan is not viable, and/or PET tracer uptake or SUV would not be able to guarantee an acceptable quality of dose delivery (e.g., poor uptake, non-specific uptake, high levels of background noise, etc.). Terminating 212 the treatment session may optionally comprise updating or re-calculating the treatment plan to adapt for the changes in the biological activity and/or physiological data. The updated or adapted treatment plan may then be used for a future treatment session.

If it is determined 210 that the treatment session should not be terminated, method 200 may optionally comprise updating or re-calculating the treatment plan (i.e., re-planning, adapting the treatment plan) to account for any changes in the expected dose distribution due to differences in the biological activity and/or physiological data acquired at the time of delivery as compared to the biological activity and/or physiological data acquired during treatment planning. The updated treatment plan may satisfy most (if not all) of the clinical goals set by the clinician while accounting for the current state of the patient and/or target regions as indicated by the acquired biological activity and/or physiological data. For example, the updated treatment plan may incorporate the acquired biological activity and/or physiological data and calculate updated radiation delivery parameters (e.g., RFM, fluence map, radiation emission assembly instructions, etc.) such that the delivered dose to the one or more target regions is within the desired dose range.

A treatment plan may be updated in one or more aspects, depending on the type and/or magnitude of the changes in physiological and/or biological activity data. Treatment plans may be updated to increase the delivered dose to a target region if the data indicates that the target region is more radiation-resistant, and/or the irradiation area may be increased or decreased depending on changes in motion of the target region or size of the target region. Alternatively or additionally, a treatment plan may be adjusted to decrease irradiation of OARs. Adaptations to a treatment plan due to changes in metabolic tumor volume (MTV) may include adjusting target contours to fit the new size and shape of the MTV. Adaptations due to changes in metabolic rate may include reducing the dose to areas of reduced metabolic rate and increase dose to areas of increased metabolic rate. Areas of lowered metabolic rates may correspond with non-tumor tissue while areas of elevated metabolic rates may correspond with tumor tissue. Changes in metabolic activity levels and/or concentration of metabolites may be calculated based on changes in SUV and/or spectroscopic data (e.g., MR spectroscopy). Plan adaptations due to an increase in the LG to NTG ratio (relative to surrounding OARs) may include increasing dose gradients (e.g., steeper dose gradients) in those regions. A plan adaptation may include increasing dose to a region if an increase to the LG level of that region is detected. Plan adaptations due to detected changes in RPF, such as a lower net flow rate, may include reducing the irradiation of OARs near the target region (e.g., increasing OAR dose sparing), which may optionally include reducing the delivered dose to the target region. Adaptations to a treatment plan due to increases in DNA synthesis and/or protein synthesis rates may include increasing dose to voxels with positive $SUV_{diff}$ values and decreasing dose to voxels with negative $SUV_{diff}$ values. Adaptations to a treatment plan due to changes in hypoxia levels in a target region may include increasing dose (e.g., increasing minimum dose levels) if hypoxia levels increase. Adaptations to a treatment plan due to changes in folate receptor density may include increasing dose to voxels with positive values on $SUV_{diff}$ volumes, and decreasing dose to voxels with negative values on $SUV_{diff}$ volumes. Adaptations to a treatment plan due to changes in HER2 expression may include extending the dose gradient between the tumor volume of interest and normal tissue if the $SUV_{mean\_total}$ has increased (e.g., indicating an increase in HER2 genetic expression). In cases where radiotherapy is prescribed in conjunction with HER2-targeting immunotherapy, a treatment plan may be adjusted by decreasing dose to voxels with positive values on $SUV_{diff}$ volume and increasing dose to voxels with negative values on $SUV_{diff}$ volume.

Table 2 below summarizes examples of the types of physiological and/or biological activity data that may be calculated based on imaging data, methods of deriving this activity data from imaging data, and examples of corresponding treatment plan adaptations.

TABLE 2

Examples of Physiological and/or Biological Data and Treatment Plan Adaptations

| Tracer | Biological Data Type | Biological Effect Measured | Calculation Method | Example Plan Adaptation |
|---|---|---|---|---|
| 18F-fluorodeoxyglucose | Metabolic Tumor Volume (MTV) | Aerobic and anaerobic glycolysis, glucose consumption or metabolism | Threshold region on SUV using a gradient of $SUV_{max}$ to delineate between tumor tissue and non-tumor tissue, typically using a gradient of 30-50% $SUV_{max}$ | Adjust target contours to fit newly determine metabolic volume |
| 18F-fluorodeoxyglucose | Metabolic Rate (MRFDG) | Aerobic and anaerobic glycolysis, glucose consumption or metabolism | Calculate tracer kinetics to determine 18F-FDG Flux Constant Ki | Reduce dose to areas of reduced metabolic rate which indicates inflammation, not tumor tissue, and increase dose to areas of increased metabolic rate which indicates tumor tissue. |
| 18F-fluorodeoxyglucose | Lesion Glycolysis (LG) to Normal Tissue Glycolysis (NTG) Ratio (LG:NTG) | Aerobic and anaerobic glycolysis, glucose consumption or metabolism | LG: Multiply MTV by $SUV_{mean}$ of MTV, NTG: Multiply OAR Volume by $SUV_{mean}$ of OAR Volume | Compare LG to NTG of surrounding OARs, and in areas where an increase in ratio is detected, allow for steeper dose gradients in those regions to be applied, providing higher average dose to the tumor region and lower dose to the normal tissue region. |

TABLE 2-continued

Examples of Physiological and/or Biological Data and Treatment Plan Adaptations

| Tracer | Biological Data Type | Biological Effect Measured | Calculation Method | Example Plan Adaptation |
|---|---|---|---|---|
| 13N-nitrogen | Regional Pulmonary Function (RPF) | Aeration of blood containing the tracer | Calculate tracer kinetics of a given region of interest using multicompartment model to determine tracer flow rates of aerated tracer vs shunt tracer and comparing the recorded flow rates to receive a net flow rate of aerated tracer, which can then be used to compare to expected values from previous scans. | If net flow rate is lower than previous scans, regional pulmonary function has worsened, so dose constraints and tolerances to OAR dose are adjusted to increase the amount of OAR dose sparing. This may result in or require lower dose to tumor target volumes as well. |
| 18F-fluorodeoxyglucose | Lesion Glycolysis (LG) | Aerobic and anaerobic glycolysis, glucose consumption or metabolism | Calculate $SUV_{mean}$ of MTV. Multiply MTV by $SUV_{mean}$ | Compare LG to LG of previous scans. If LG has increased, increase dose to MTV. |
| 18F-fluorothymidine | DNA Synthesis (DNASynth) | DNA synthesis, tumor-cell proliferation | Calculate $SUV_{diff}$ of region of interest (subtract SUV of voxels owned by region of interest from SUV of voxels owned by region of interest in previous scan) | Increase dose to voxels with positive values on $SUV_{diff}$ volume, decrease dose to voxels with negative values on $SUV_{diff}$ volume |
| 11C-methionine | Protein Synthesis (ProteinSynth) | Protein synthesis, tumor-cell proliferation | Calculate $SUV_{diff}$ of region of interest (subtract SUV of voxels owned by region of interest from SUV of voxels owned by region of interest in previous scan) | Increase dose to voxels with positive values on $SUV_{diff}$ volume, decrease dose to voxels with negative values on $SUV_{diff}$ volume |
| 18F-fluoromisonidazole | Hypoxia | Hypoxia | Threshold subregion of target on SUV using a gradient of $SUV_{max}$ to delineate between hypoxic tumor tissue and non-hypoxic tumor tissue. | Create new boost target region contours for the hypoxic region and increase the minimum dose to those regions. Adjust dosimetric objectives of surrounding tissue to accommodate the increased dose to hypoxic regions. |
| 18F-fluoroazomycin-arabinoside | Hypoxia | Hypoxia | Threshold subregion of target on SUV using a gradient of $SUV_{max}$ to delineate between hypoxic tumor tissue and non-hypoxic tumor tissue. | Create new boost target region contours for the hypoxic region and increase the minimum dose to those regions. Adjust dosimetric objectives of surrounding tissue to accommodate the increased dose to hypoxic regions. |

TABLE 2-continued

Examples of Physiological and/or Biological Data and Treatment Plan Adaptations

| Tracer | Biological Data Type | Biological Effect Measured | Calculation Method | Example Plan Adaptation |
|---|---|---|---|---|
| 18F-fluoroerythronitroimidazole | Hypoxia | Hypoxia | Threshold subregion of target on SUV using a gradient of $SUV_{max}$ to delineate between hypoxic tumor tissue and non-hypoxic tumor tissue. | Create new boost target region contours for the hypoxic region and increase the minimum dose to those regions. Adjust dosimetric objectives of surrounding tissue to accommodate the increased dose to hypoxic regions. |
| 3'-Aza-2'-[18F]fluorofolic Acid | Folate Receptor (FR) | Folate receptor density | Calculate $SUV_{diff}$ of region of interest (subtract SUV of voxels owned by region of interest from SUV of voxels owned by region of interest in previous scan) | Increase dose to voxels with positive values on $SUV_{diff}$ volume, decrease dose to voxels with negative values on $SUV_{diff}$ Volume |
| N-succinimidyl 3-((4-(4-(18)F-fluorobutyl)-1H-1,2,3-triazol-1-yl)methyl)-5-(guanidinomethyl)benzoate radiolabeled 5F7 antibody | HER2 Genetic Expression (HER2GE) | HER2 Concentration | Calculate $SUV_{mean}$ of tumor volume of interest; multiply tumor VOI by $SUV_{mean}$ to get $SUV_{mean\_total}$ | If $SUV_{mean\_total}$ has increased, HER2 genetic expression has increased, and the dose gradient between the tumor volume of interest and the normal tissue should be extended out of the tumor VOI by increasing the size of the target volume receiving radiation in order to compensate for increased HER2 expression |
| N-succinimidyl 4-[18F]fluorobenzoate protein-labeled 5F7 antibody | HER2 Genetic Expression (HER2GE) | HER2 Concentration | Calculate $SUV_{diff}$ of region of interest (subtract SUV of voxels owned by region of interest from SUV of voxels owned by region of interest in previous scan) | When treating concomitantly with HER2-targeting immunotherapy, decrease dose to voxels with positive values on $SUV_{diff}$ volume and increase dose to voxels with negative values on SUVdiff volume. |
| 1-(2'-deoxy-2'-[18F]fluoroarabinofuranosyl)cytosine (18F-FAC) | T Cell DNA synthesis (DNASynth) | DNA synthesis, tumor-cell proliferation | Calculate tracer kinetics of a given region of interest using multicompartment model based on SUV intensity to determine tracer flow rates of radiolabeled T Cells penetrating into the primary tumor compartment, which can be compared to the expected baseline penetration of the primary tumor compartment by the T Cells. | As the tracer deposits and is trapped in the central primary tumor compartment, this indicates T Cell penetration into the tumor. Once the tumor volume is penetrated to the desired concentration of T Cells, dose deescalation and/or fraction reduction may be performed, changing the remainder of the course of treatment (can be done either intra or inter-fraction). |
| 11C-Choline, 18F-Choline, or non-labeled Choline metabolites (tracer with spectroscopic imaging) | Cell membrane metabolism | Neurodegenerative tumor proliferation, demyelination | Calculate diff of the concentration of metabolites in a given region of interest (subtract concentration in voxels owned by region of interest from concentration in voxels owned by | Increase dose to voxels with positive values on concentration diff volume, decrease dose to voxels with negative values on concentration diff volume |

TABLE 2-continued

Examples of Physiological and/or Biological Data and Treatment Plan Adaptations

| Tracer | Biological Data Type | Biological Effect Measured | Calculation Method | Example Plan Adaptation |
|---|---|---|---|---|
| (S)-4-(3-[18F]Fluoropropyl)-L-glutamic acid (18F-FSPG) | xC-Cystine/Glutamate Exchange | xC-Transporter Activity | Calculate $SUV_{diff}$ of region of interest (subtract SUV of voxels owned by region of interest from SUV of voxels owned by region of interest in previous scan) | Increase dose to voxels with positive values on SUVdiff volume, decrease dose to voxels with negative values on SUVdiff volume |
| [(18)F]DCFPyL (18F-PSMA) or Ga68-PSMA | PSMA Antigen Binding | PSMA Antigen Concentration Levels | Calculate $SUV_{diff}$ of region of interest (subtract SUV of voxels owned by region of interest from SUV of voxels owned by region of interest in previous scan) | increase dose to voxels with positive values on SUVdiff volume, decrease dose to voxels with negative values on SUVdiff volume |
| Ga68-DOTATATE (NETSPOT) | Somatostatin | Growth hormone receptor overexpression | Calculate $SUV_{diff}$ of region of interest (subtract SUV of voxels owned by region of interest from SUV of voxels owned by region of interest in previous scan) | Increase dose to voxels with positive values on SUVdiff volume, decrease dose to voxels with negative values on SUVdiff volume |
| Radiolabeled PD-1, PD-L1, or PD-L2 Antibody (Zr-89 Radiolabeled Antibody) | Immune Checkpoint Marker Binding | Blockage of Programmed Cell Death Protein 1 (PD-1) Immune Response | Calculate $SUV_{diff}$ of region of interest (subtract SUV of voxels owned by region of interest from SUV of voxels owned by region of interest in previous scan) | Unlike the more common SUVdiff approach, we want to avoid treating areas with high SUVdiff, to avoid T-Cells and tumors susceptible to PD-1 immunotherapy. As a result, the approach for this agent is to increase dose to voxels with negative values on SUVdiff volume, decrease dose to voxels with positive values on SUVdiff volume |

After generating an updated treatment plan (which may optionally be reviewed and approved by a clinician), method 200 may comprise delivering 216 radiation to the patient in accordance with the updated treatment plan. In some variations, this may include generating a fluence map based on the updated treatment plan, and segmenting the fluence map into DMLC leaf patterns or a sinogram. The therapeutic radiation source may be activated in accordance with instructions from the controller based on the sinogram. Method 200 may be performed one or more times during a treatment session. For example, method 200 may be performed at the beginning of a treatment session to determine whether to proceed with the current treatment plan and/or whether to update or re-calculate the current treatment plan, and then not performed again until the next treatment session. This may be referred to as online adaptive radiotherapy. Alternatively, method 200 may be performed multiple times throughout a treatment session, for example, at the beginning of a treatment session, periodically throughout the treatment session (e.g., at every firing position, every other firing position, etc.), and/or at the end of the treatment session. This may continuously update the treatment plan according to real-time state of the patient throughout the treatment session. This may be referred to as real-time adaptive radiotherapy. Optionally, method 200 may be performed as commanded by a clinician (via the GUI, for example). The biological activity and/or physiological data acquired at the time of a treatment session may be used after the treatment session in order to update or re-calculate the treatment plan for the next treatment session. This may be referred to as offline adaptive radiotherapy.

Online Adaptive Radiotherapy

Figure 2B:
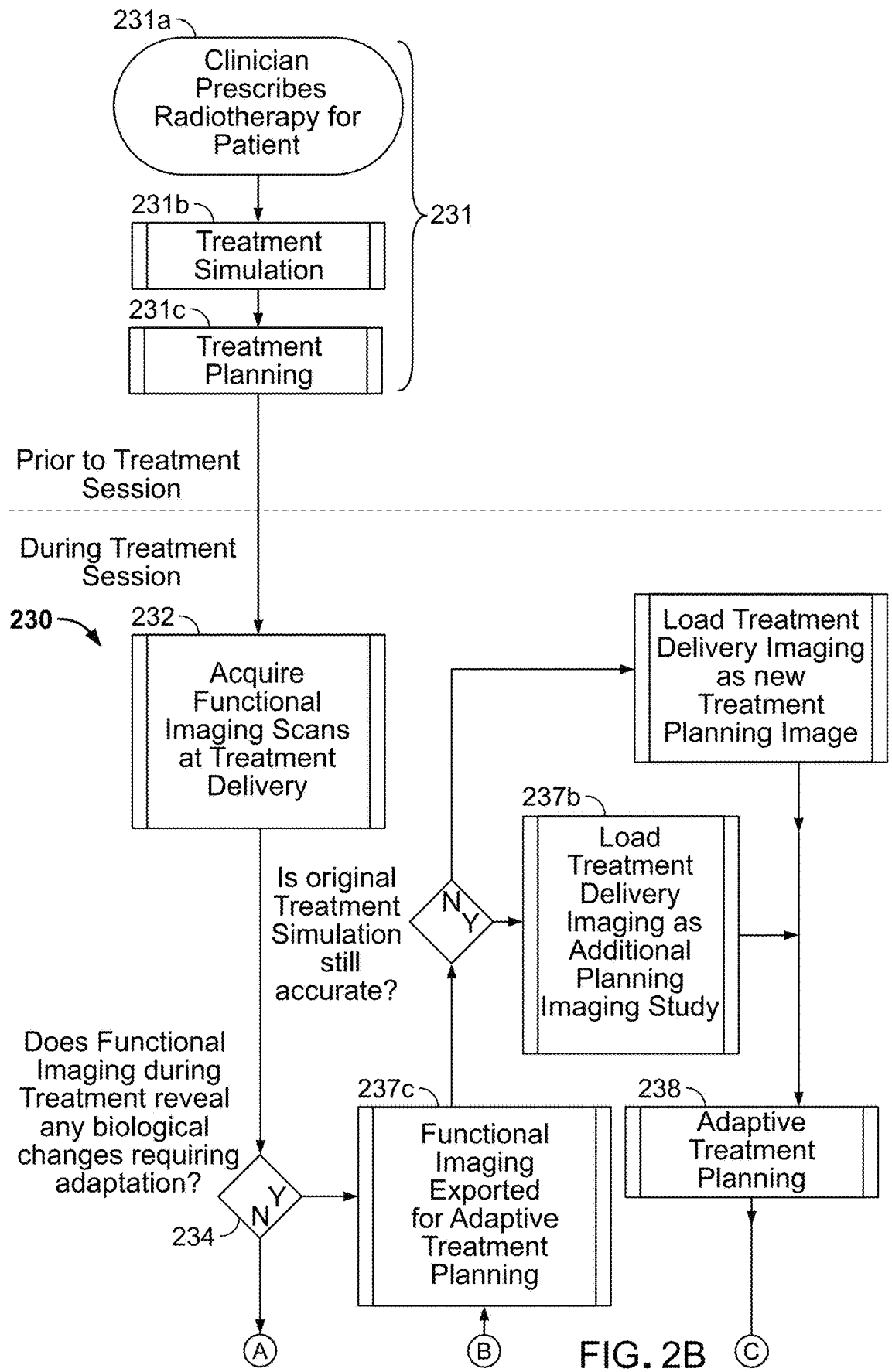
FIG. 2B depicts a flowchart representing one variation of a method for online adaptive radiotherapy.
Figure 2B:
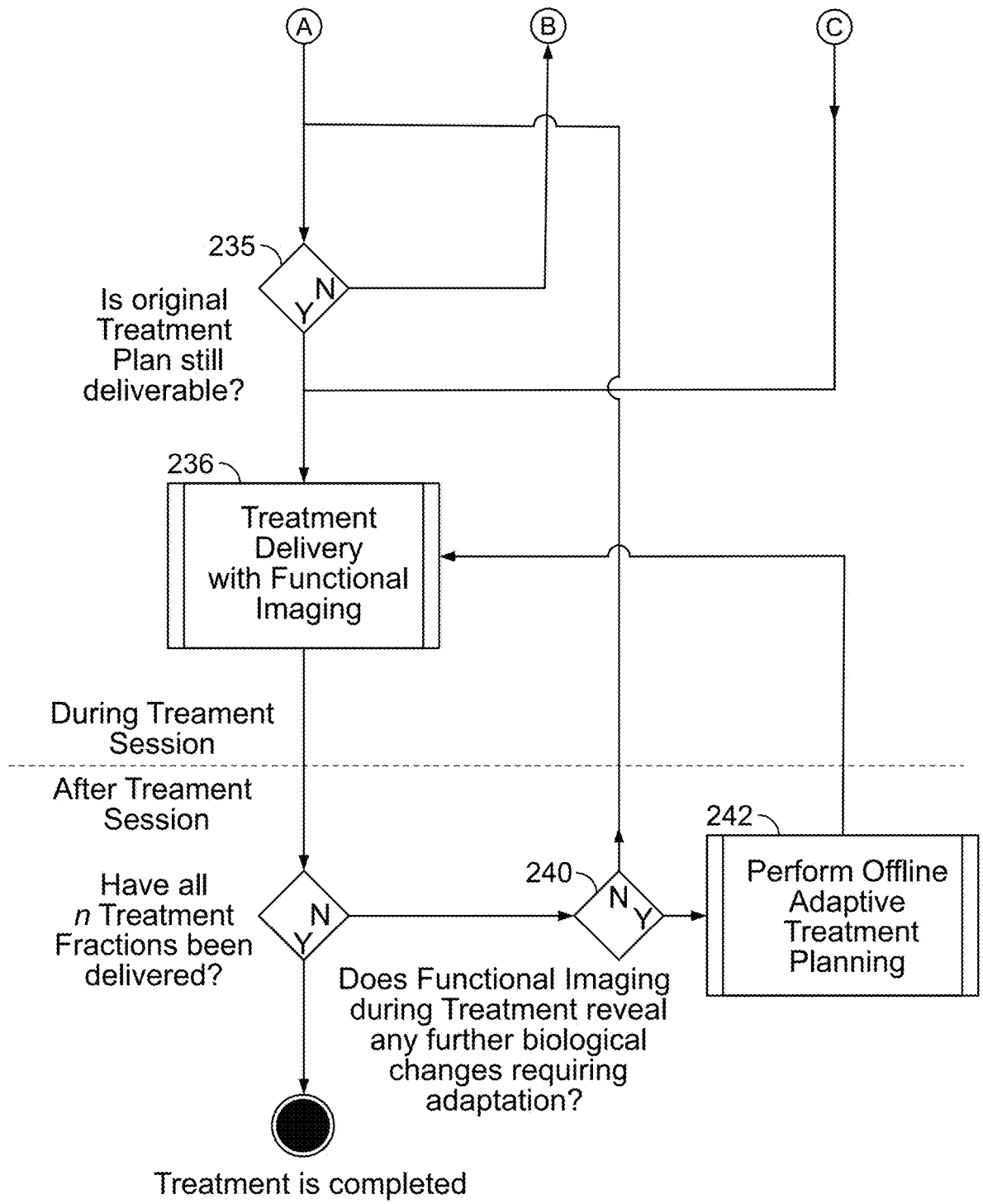

FIG. 2B depicts one variation of a method for online adaptive radiotherapy based on biological activity and/or physiological data. Prior to a treatment session (blocks 231a-231c), a treatment plan may be generated for the patient based on images or image data acquired using any desired imaging modality (e.g., PET, SPECT, MRI, CT, X-ray, etc.), and/or with the consultation of a clinician. In some variations, there may be treatment plan simulations to calculate and/or estimate the expected dose distribution profile of a treatment plan, and further changes to the treatment plan depending on the outcome of the simulations. Online adaptive radiotherapy may comprise updating or calculating a treatment plan based on biological and/or physiological data acquired at the start of a treatment session (e.g., before the therapeutic radiation source is turned on). The newly adapted or calculated treatment plan may be used to deliver radiation to the patient during that treatment session. For example, an online adaptive radiotherapy method 230 may comprise acquiring 232 imaging data, such as functional imaging scans, at the time of treatment delivery. This may include, for example, acquiring imaging data using any imaging modality (e.g., PET, SPECT, MRI, CT, X-ray, etc.) at the start of a treatment session, before the first radiation beam is applied to the patient. The controller may then evaluate 234 whether the biological activity and/or physiological data extracted from the imaging data indicates that a change to the current treatment plan is needed. Evaluating biological activity and/or physiological data may comprise extracting various parameters of the patient and/or target region(s), including, but not limited to, target region delineation, target region isocenters, and/or OAR location. Dose delivery rate, treatment time, isodose gradients, dose heterogeneity, dose conformality, beam characteristics, and motion management strategies may be adapted based on biological activity and/or physiological data. This may include, for example, shortening treatment time by increasing the dose delivery rate and couch speed when the motion envelope of the patient's target region is reduced in size due to a specific biological function (e.g. using PET tracer kinetics to detect reduced regional pulmonary function which may have the side effect of reducing the motion envelope of a near-region target). Alternatively or additionally, it may include, for example, increasing the isodose gradient and dose heterogeneity of a given target region in order to provide a higher concentration of dose to a region in the target region that was not present on the previous treatment planning reference imagery (e.g. a hypoxic region that was not present on simulation imagery); this adaptation may also include but does not necessitate an increased total delivered dose to the target region. Alternatively or additionally, it may include, for example, altering the specific mechanism of motion management mechanism to be used during treatment as a result of a physiological indicator that the motion management mechanism may cause more harm than benefit (e.g. shifting or reducing the pressure applied by an abdominal compression unit because of the detection of a higher intra-abdominal pressure due to a previously undetected perfusion and additionally compensating the treatment plan's target region size to accommodate the now increased motion envelope). Optionally, the method may comprise determining 235 whether the radiotherapy system is able to deliver the prescribed radiation dose and/or whether the prescribed radiation dose has been delivered in accordance with the plan. Methods for evaluating treatment plans to determine whether the current treatment plan needs to be updated or adapted based on patient imaging data are described further below. If no changes are needed, the radiation treatment system may proceed to deliver treatment 236 in accordance with the current treatment plan and may optionally acquire imaging data (e.g., PET data) that is indicative of biological activity and/or physiological parameters.

If changes to the treatment plan are needed, the extracted biological activity and/or physiological data may be used to recalculate or adapt 238 the treatment plan. Optionally, functional image data and/or planning image data (from blocks 237a and 237b respectively) may be used to adapt the treatment plan. Modifications to a treatment plan may include absolute dose values for each target region, dose limits for each target region and/or cumulatively for the patient, biological effective dose values, equivalent dose values, and treatment fractionation. This may include, for example, adapting the dose limits for a target region by increasing the maximum dose allowed over a percentage of the volume in order to account for a hypoxic region forming between simulation and treatment. Additionally or alternatively, this may include, for example, increasing the allowed biological effective dose constraint for a region in order to accommodate for a change in treatment fractionation resulting from substantially different metabolic activity being detected in the target region, resulting in the current fraction being untreatable. Alternatively or additionally, depending on the type(s) of tracer(s) used, treatment plans may be adapted as described above and summarized in Table 2. In some variations, recalculating or adapting a treatment plan to incorporate biological activity and/or physiological data acquired at the time of treatment may comprise simulating one or more testing treatment plans with the acquired biological activity and/or physiological data, and selecting an updated treatment plan from the one or more testing treatment plans that meet clinical objectives and/or provides a desired dose distribution. In some variations, an updated or adapted treatment plan may adhere to specified or approved PQI ranges and/or biological activity and/or physiological data ranges. The adaptive radiotherapy treatment planning process may follow a similar methodology as normal treatment planning, generating a treatment plan and related treatment planning artifacts. In some variations, many of these artifacts are automatically generated or generated with the use of tools specifically designed to reduce the amount of time required to perform the operations. In some variations, the adaptations and adaptive treatment planning process is performed on the same software as the original treatment plan. The method 230 may then comprise delivering radiation 236 in accordance with the updated or adapted treatment plan. In some variations, the updated or adapted treatment plan may be reviewed, evaluated, and/or approved by a clinician at the time it is created and/or before radiation is delivered according to the updated plan. The updated or adapted treatment plan may optionally be stored in a treatment plan database (e.g., within the memory of a controller and/or a remove server memory). Future treatment sessions or fractions may reference stored treatment plans, as may be desirable. Alternatively or additionally, the updated or adapted treatment plan may be stored in a patient treatment record, for review and assessment by the patient and/or clinician. Future treatment sessions or fractions may reference treatment plans stored in a patient record, as may be desirable.

Optionally, at the conclusion of the treatment session, additional imaging data may be acquired. For example, one or more final functional imaging scans may be acquired at the conclusion of the treatment session (e.g., after the last radiation beam is applied). Optionally, after the treatment session (i.e., after the patient has exited the radiation treatment system), the controller may evaluate 240, based on biological activity and/or physiological data extracted from the final imaging scan(s), whether the treatment plan that was delivered in the treatment session should be updated for the next treatment session. If the biological activity and/or physiological data indicates that changes to the treatment plan are needed, the controller may then recalculate or adapt the treatment plan 242 for a future treatment session, using any one or more of the adaptations described above. Offline adaptive treatment planning may refer to calculating and/or simulating treatment plans in between treatment sessions using biological activity and/or physiological data acquired during a previous treatment session. Optionally, treatment plans generated during a treatment session and/or offline may be stored in a treatment plan database. Treatment plans in a database may be used in future treatment sessions, as may be desirable.

Real-Time Adaptive Radiotherapy

Figure 2C:
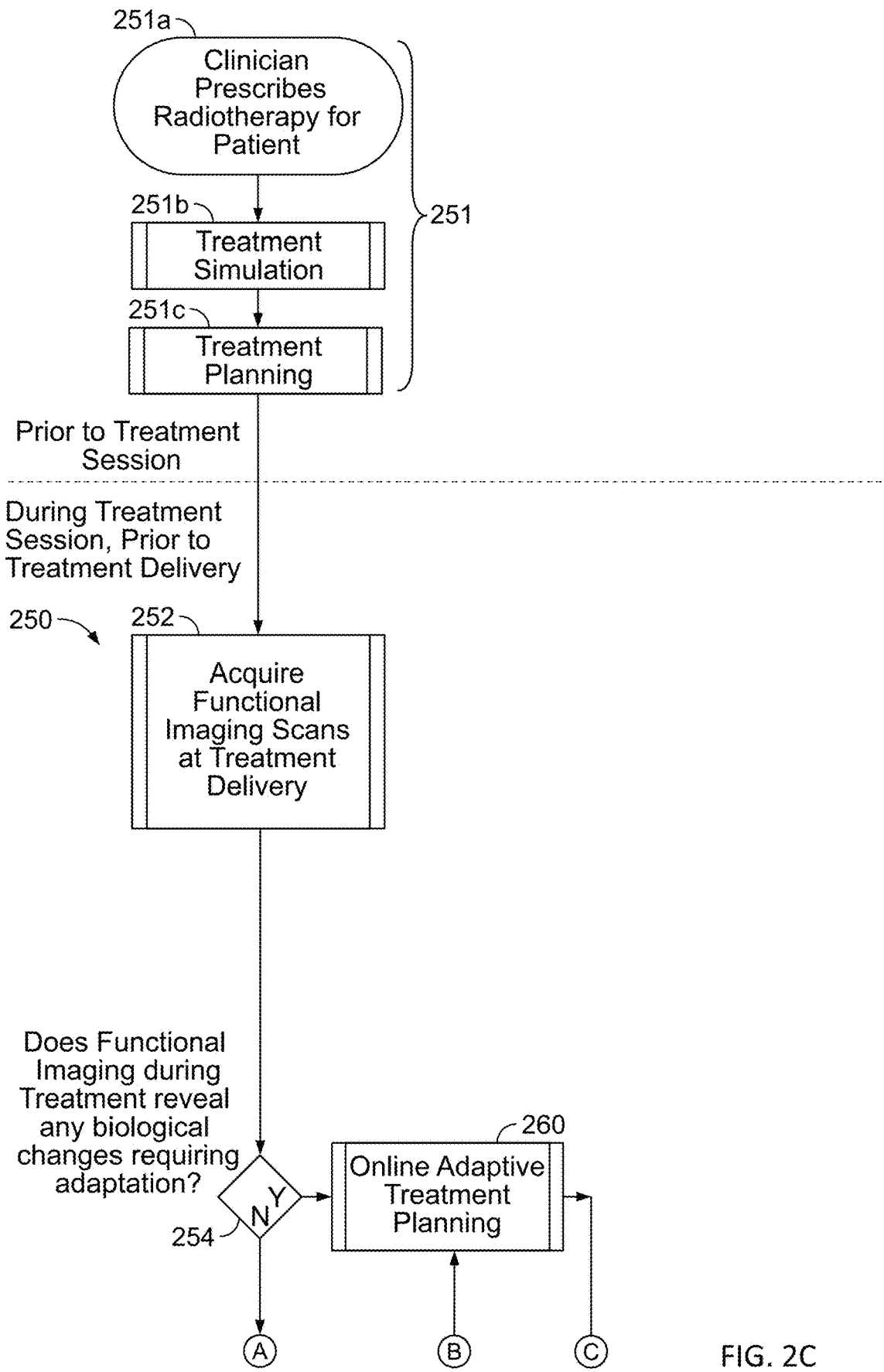
FIG. 2C depicts a flowchart representing one variation of a method for real-time adaptive radiotherapy.
Figure 2C:
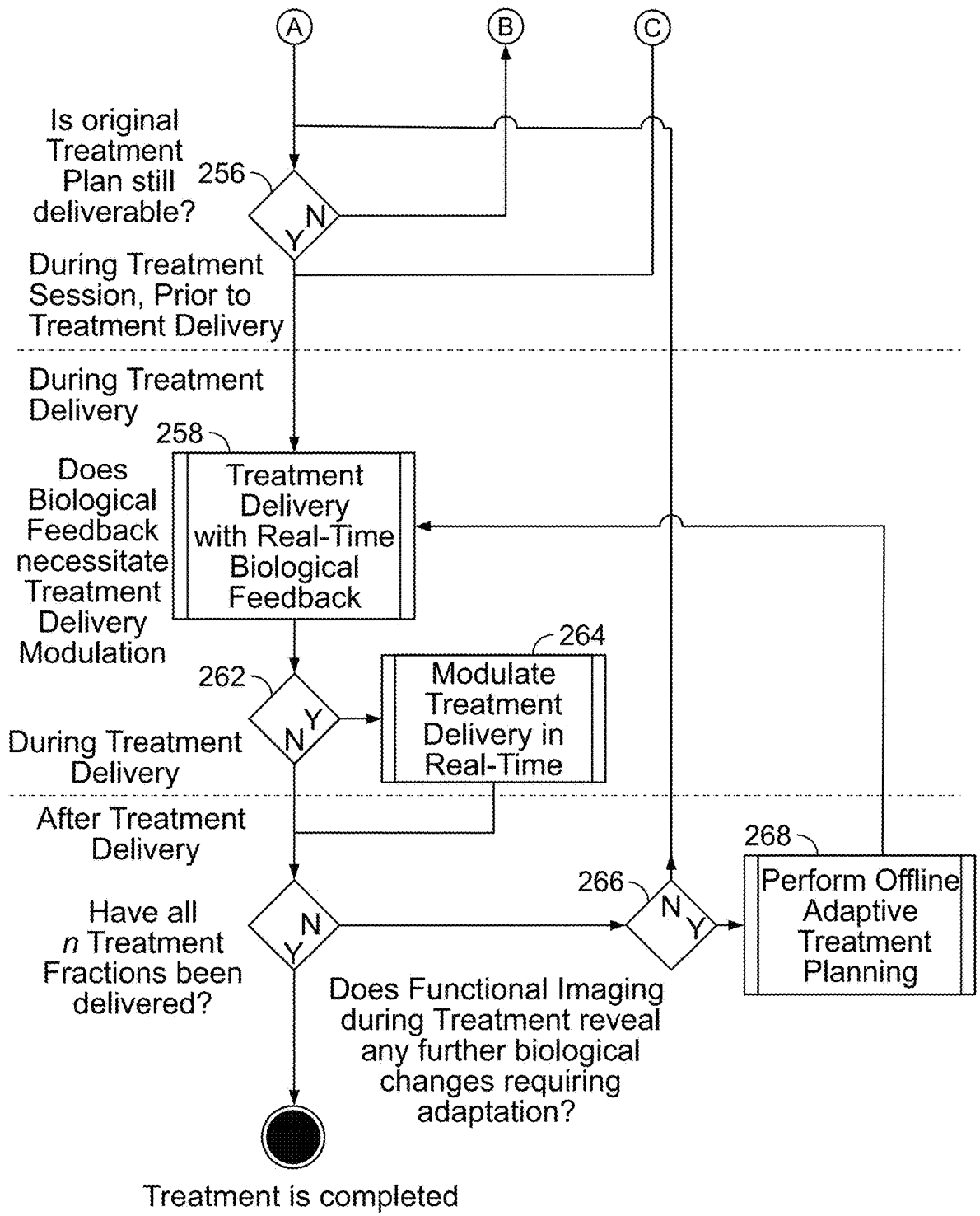

FIG. 2C depicts one variation of a method for real-time adaptive radiotherapy based on biological activity and/or physiological data. In real-time adaptive radiotherapy, the treatment plan is updated or adapted multiple times during the treatment session based on biological activity and/or physiological data acquired during the same treatment session. For example, if the acquired biological activity and/or physiological data extracted from image data acquired at the start of the treatment session indicate that a treatment plan generated at an earlier planning session is still applicable, the radiation treatment system may begin radiation dose delivery according to that treatment plan. As functional image data is acquired during the treatment session, the treatment plan may be updated or adapted according to any changes detected in biological activity and/or physiological data. Real-time adaptive radiotherapy may comprise updating or calculating the treatment plan based on biological and/or physiological data acquired throughout the treatment session (e.g., during the activation of the therapeutic radiation source). The newly adapted or calculated treatment plan may be delivered to the patient during that treatment session, and in some variations, in real-time. At the end of the treatment session, the final iteration of the treatment plan may not be the same as the treatment plan from the beginning of the treatment session, depending on how patient biological activity and/or physiology may change in the course of treatment.

Turning now to FIG. 2C, prior to a treatment session (blocks 251a-251c), a treatment plan may be generated for the patient based on images or image data acquired using any desired imaging modality (e.g., PET, SPECT, MRI, CT, X-ray, etc.), and/or with the consultation of a clinician. In some variations, there may be treatment plan simulations to calculate and/or estimate the expected dose distribution profile of a treatment plan, and further changes to the treatment plan depending on the outcome of the simulations. An online adaptive radiotherapy method 250 may comprise acquiring 252 imaging data, such as functional imaging scans, at the time of treatment delivery. This may include, for example, acquiring imaging data using any imaging modality (e.g., PET, SPECT, MRI, CT, X-ray, etc.) at the start of a treatment session, before the first radiation beam is applied to the patient. The controller may then evaluate 254 whether the biological activity and/or physiological data extracted from the imaging data indicates that a change to the current treatment plan is needed. Evaluating biological activity and/or physiological data may comprise extracting various parameters of the patient and/or target region(s), including, but not limited to, target region delineation, target region isocenters, and/or OAR location. Biological activity and/or physiological data may also provide information related to dose delivery rate, treatment time, isodose gradients, dose heterogeneity, dose conformality, beam characteristics, and the motion management strategies This may include, for example, shortening treatment time by increasing the dose delivery rate and couch speed when the motion envelope of the patient's target region is reduced in size due to a specific biological function (e.g. using PET tracer kinetics to detect reduced regional pulmonary function which may have the side effect of reducing the motion envelope of a near-region target). Alternatively or additionally, it may include, for example, increasing the isodose gradient and dose heterogeneity of a given target region in order to provide a higher concentration of dose to a region in the target region that was not present on the previous treatment planning reference imagery (e.g. a hypoxic region that was not present on simulation imagery); this adaptation may also include but does not necessitate an increased total delivered dose to the target region. Alternatively or additionally, it may include, for example, altering the specific mechanism of motion management mechanism to be used during treatment as a result of a physiological indicator that the motion management mechanism may cause more harm than benefit (e.g. shifting or reducing the pressure applied by an abdominal compression unit because of the detection of a higher intra-abdominal pressure due to a previously undetected perfusion and additionally compensating the treatment plan's target region size to accommodate the now increased motion envelope). Methods for evaluating treatment plans to determine whether the current treatment plan needs to be updated or adapted based on patient imaging data are described further below.

If no changes are needed, the radiation treatment system may proceed to deliver treatment 258 in accordance with the current treatment plan. If changes to the treatment plan are needed, the extracted biological activity and/or physiological data may be used to recalculate or adapt 260 the treatment plan. Modifications to a treatment plan may include absolute dose values for each target region, dose limits for each target region and/or cumulatively for the patient, biological effective dose values, equivalent dose values, and treatment fractionation, as described above with reference to FIG. 2B. Alternatively or additionally, depending on the type(s) of tracer(s) used, treatment plans may be adapted as described above and summarized in Table 2. In some variations, recalculating or adapting a treatment plan to incorporate biological activity and/or physiological data acquired at the time of treatment may comprise simulating one or more testing treatment plans with the acquired biological activity and/or physiological data, and selecting an updated treatment plan from the one or more testing treatment plans that meet clinical objectives and/or provides a desired dose distribution, as described above with reference to FIG. 2B. In some variations, an updated or adapted treatment plan may adhere to specified or approved PQI ranges and/or biological activity and/or physiological data ranges. The method 250 may then comprise delivering radiation 258 in accordance with the updated or adapted treatment plan. In some variations, the updated or adapted treatment plan may be reviewed, evaluated, and/or approved by a clinician at the time it is created and/or before radiation is delivered according to the updated plan.

During the treatment session, biological activity and/or physiological data may continue to be monitored (e.g., in real-time) by acquiring imaging data while applying radiation according to the current version or iteration of the treatment plan. For example, imaging data may be acquired at predetermined time intervals (e.g., about 10 Hz, 5 Hz, 2 Hz, 1 Hz, 0.5 Hz, etc.) and/or at all firing positions or certain subsets of firing positions. Method 250 may then comprise determining 262 whether to modulate or adapt treatment delivery. Methods for evaluating treatment plans to determine whether a current treatment plan is suitable for treatment in light of the updated biological activity and/or physiological data are described further below. Modulating or adapting 264 treatment delivery may comprise, for example, shifting or scaling a fluence map, and/or adjusting dose intensity for certain target regions, and/or increasing or decreasing the dose for certain target regions, etc. Additionally or alternatively, treatment delivery may be modulated by changing the duty cycle of the treatment, increasing or decreasing the number of available firing positions in order to accommodate changes that would prevent regions from or allow regions to receive a different amount of radiation than originally planned (e.g. detecting the severity of a cardiac perfusion getting worse mid-treatment, which may allow the system to reduce the number of firing positions exposing that region to radiation while increasing the overall treatment time to reach the same prescribed dose of radiation). Alternatively or additionally, depending on the type(s) of tracer(s) used, treatment plans may be adapted as described above and summarized in Table 2. The radiation treatment system may then proceed to deliver radiation to the patient in accordance with the modifications calculated above.

Optionally, at the conclusion of the treatment session, additional imaging data may be acquired. For example, a final functional imaging scan may be acquired at the conclusion of the treatment session (e.g., after the last radiation beam is applied). Optionally, after the treatment session (i.e., after the patient has exited the radiation treatment system), the controller may evaluate 266, based on biological activity and/or physiological data extracted from the final data acquisition, whether to update or adapt any of the treatment parameters or plans executed during the treatment session. If the biological activity and/or physiological data indicate that changes to any treatment parameters or plan are needed, the controller may then recalculate or adapt the treatment plan 268 for a future treatment session using one or more of the adaptations described above. Optionally, treatment parameters and/or treatment plans generated during a treatment session and/or offline may be stored in a treatment plan database. Treatment plans in a database may be used in future treatment sessions, as may be desirable.

Offline Adaptive Radiotherapy

Imaging data (such as functional imaging data) acquired during a treatment session may be used to calculate or generate a treatment plan for the patient at the next treatment session. Offline adaptive radiotherapy may comprise calculating or generating a treatment plan in between treatment sessions, when the patient is not located within the treatment system. As described previously, imaging data may be acquired at the start of a treatment session, before the first radiation beam is applied to the patient. The imaging data may be acquired using any imaging modality, such as PET, SPECT, MRI, CT, X-ray, etc. The controller may then evaluate whether a previously-calculated treatment plan is deliverable and/or meets clinical goals, based on biological activity and/or physiological data extracted from the acquired imaging data. If not, the treatment session is terminated and the imaging data, extracted biological activity and/or physiological data are stored in controller memory for updating or adapting the treatment plan for the next treatment session. If the previously-calculated treatment plan is deliverable and/or meets clinical goals, radiation therapy based on that treatment plan may proceed. Optionally, imaging data may be acquired during the treatment session and/or at the end of the treatment session. All imaging data, extracted biological activity and/or physiological data, and any other computed quantities may be stored in controller memory. After the termination of the treatment session, the controller may update or adapt the treatment plan (or generate a new treatment plan) based on the acquired imaging data, using one or more of the adaptations described above. As described previously, any treatment plans and/or treatment session parameters may be stored in a treatment plan database and/or patient record database.

Figure 2D:
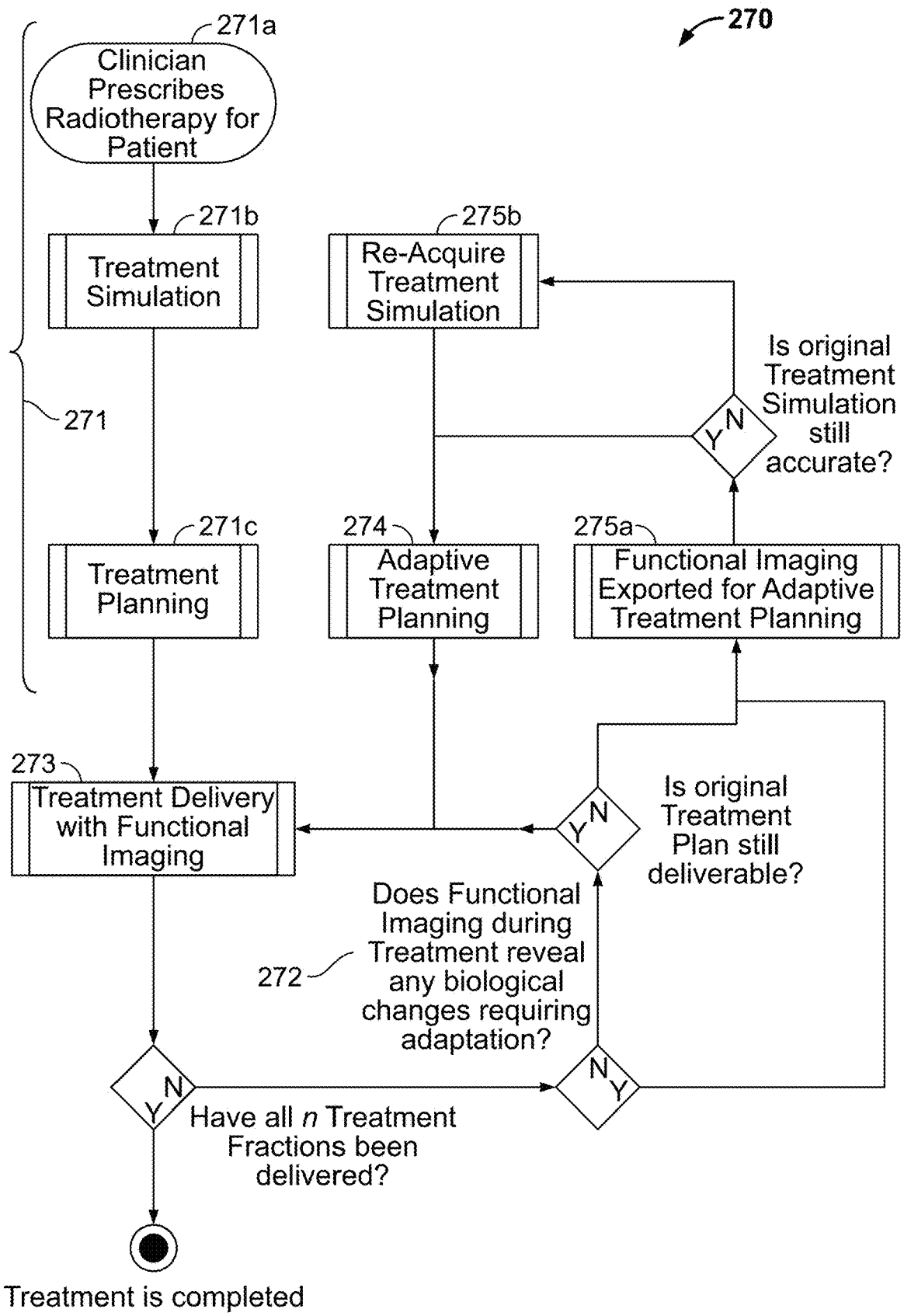
FIG. 2D depicts a flowchart representing one variation of a method for offline adaptive radiotherapy.

FIG. 2D depicts a method for offline adaptive radiotherapy. Prior to a treatment session (blocks 271a-271c), a treatment plan may be generated for the patient based on images or image data acquired using any desired imaging modality (e.g., PET, SPECT, MRI, CT. X-ray, etc.), and/or with the consultation of a clinician, as described previously. During a treatment session where radiation is delivered 273 based on a previously-generated treatment plan, the radiation treatment system acquires imaging data from which biological activity and/or physiological data may be extracted. This data may be stored in controller memory and after the conclusion of the treatment session, may be used to update or adapt the treatment plan (or to generate a new treatment plan). Offline adaptive radiotherapy method 270 may comprise determining 272 whether to update the treatment plan based on the biological activity and/or physiological data extracted from the imaging data acquired during the previous treatment session. Evaluating biological activity and/or physiological data may comprise extracting various parameters of the patient and/or target region(s), including, but not limited to, target region delineation, target region isocenters, and/or OAR location. Biological activity and/or physiological data may also provide information related to dose delivery rate, treatment time, isodose gradients, dose heterogeneity, dose conformality, beam characteristics, and the motion management strategies. This may include, for example, shortening treatment time by increasing the dose delivery rate and couch speed when the motion envelope of the patient's target region is reduced in size due to a specific biological function (e.g. using PET tracer kinetics to detect reduced regional pulmonary function which may have the side effect of reducing the motion envelope of a near-region target). Alternatively or additionally, it may include, for example, increasing the isodose gradient and dose heterogeneity of a given target region in order to provide a higher concentration of dose to a region in the target region that was not present on the previous treatment planning reference imagery (e.g. a hypoxic region that was not present on simulation imagery); this adaptation may also include but does not necessitate an increased total delivered dose to the target region. Alternatively or additionally, it may include, for example, altering the specific mechanism of motion management mechanism to be used during treatment as a result of a physiological indicator that the motion management mechanism may cause more harm than benefit (e.g. shifting or reducing the pressure applied by an abdominal compression unit because of the detection of a higher intra-abdominal pressure due to a previously undetected perfusion and additionally compensating the treatment plan's target region size to accommodate the now increased motion envelope). Alternatively or additionally, depending on the type(s) of tracer(s) used, treatment plans may be adapted as described above and summarized in Table 2. Methods for evaluating treatment plans to determine whether the current treatment plan needs to be updated or adapted based on patient imaging data are described further below.

If no changes are needed, the treatment plan may be used to deliver radiation for the next treatment session or fraction. If changes to the treatment plan are needed and/or the biological activity data and/or physiological data meet the criteria for updating the treatment plan, the extracted biological activity and/or physiological data may be used to recalculate or adapt 274 the treatment plan. Optionally, functional image data and/or planning image data (block 275a) may be used to adapt the treatment plan. Optionally, the treatment simulation may be re-acquired (block 275b) to adapt the treatment plane. Modifications to a treatment plan may include absolute dose values for each target region, dose limits for each target region and/or cumulatively for the patient, biological effective dose values, equivalent dose values, and treatment fractionation, as described above with reference to FIG. 2B. Alternatively or additionally, depending on the type(s) of tracer(s) used, treatment plans may be adapted as described above and summarized in Table 2. In some variations, recalculating or adapting a treatment plan to incorporate biological activity and/or physiological data acquired at the time of treatment may comprise simulating one or more testing treatment plans with the acquired biological activity and/or physiological data, and selecting an updated treatment plan from the one or more testing treatment plans that meet clinical objectives and/or provides a desired dose distribution, as described above with reference to FIG. 2B. In some variations, an updated or adapted treatment plan may adhere to specified or approved PQI ranges and/or biological activity and/or physiological data ranges. The updated treatment plan may be used for the following treatment session or fraction. Method 270 may be repeated, as desired, after each treatment session or a selected set of treatment sessions. In some variations, the treatment plan calculations may be performed by a radiation treatment system controller. Alternatively or additionally, the radiation treatment system may transmit collected imaging data and/or biological activity and/or physiological data to a remote controller, such as a treatment planning system controller, which may perform the treatment plan calculations and transmit a treatment plan (which may or may not be updated) back to the radiation treatment system.

Methods for Evaluating Treatment Plans

One or more methods may be used to evaluate a treatment plan to determine whether the treatment plan would provide a desired dose of radiation to a ROI or target region. The desired radiation dose may be, in some variations, a prescription that is written by a radiation oncologist and may specify dose-volume (DV) constraints for target regions (e.g., irradiation-target regions and/or irradiation-avoidance regions). These may include DV constraints for tumor regions and/or radiation-sensitive regions (e.g., organs at risk). An irradiation-target region comprising a tumor may include the gross tumor volume and margins surrounding the gross tumor volume to account for microscopic disease, tumor motion, and patient setup uncertainty. An example of a radiation dose prescription for a lung stereotactic treatment is depicted in FIG. 3A. As described in the table, a clinician may specify different types of ROIs in a patient, for example, one or more planning target volumes (PTVs; which may include a tumor mass and a margin around the tumor mass), spinal cord regions, whole lung, skin regions, ribs, heart, esophagus, liver, and particular vascular regions (e.g., regions occupied by vessels such as aorta, inferior vena cava, superior vena cava, pulmonary arteries or pulmonary vein), including at least a portion of the arteriovenous system. Some of these ROIs are irradiation-target regions (e.g., PTV) while others are irradiation-avoidance regions (e.g., spinal cord, lung, skin, vasculature). For each of ROI type, the clinician may specify a threshold for the proportion of the ROI to be irradiated, the maximum cumulative amount of radiation that can be applied over the entire ROI, and the maximum amount of radiation that can be applied to a portion of the ROI. For example, for an irradiation-target region such as a PTV region, the radiation dose prescription may specify that at least 95% of the PTV region be irradiated, with a maximum cumulative radiation level of about 50 Gy, and that no portion of the PTV may be exposed to radiation greater than 107% of the prescribed radiation level (e.g., 1.07×50 Gy=53.5 Gy). In some variations, a clinician may specify that a sub-region of the PTV is to be irradiated. That is, the clinician may specify that only the tumor mass region(s) of the PTV is to be irradiated, and/or a certain proportion of the PTV volume (e.g., about 10%, about 20% about 25%, about 35% about 40%, about 50%, about 60%, about 65%, about 70%, about 75%, about 80%, about 900%, about 95%, etc.) is to be irradiated. Examples of PTV sub-regions that a clinician may specify for irradiation may include tumor mass region(s), a sub-region of a tumor mass region, a subset of a plurality of tumor mass regions, one or more hypoxic regions, one or more PET-avid regions, and/or any combination of the above. Without wishing to be bound by theory, irradiation of a portion of a PTV (instead of the entire portion of the PTV) may cause a sufficient level of tumor cell death to trigger a patient immune response. Recruiting a patient's immune system in conjunction with targeted radiation delivery may help facilitate suppression of tumor growth while reducing overall patient radiation exposure (as compared to a treatment where the entire portion of the PTV is irradiated). As for an irradiation-avoidance region such as a spinal cord region (and/or lung, and/or skin, and/or vascular region), the radiation dose prescription may specify that no more than about 0.25 cc be irradiated, with a maximum cumulative radiation level of about 22.5 Gy, and that no portion of the spinal cord region may be exposed to radiation greater than about 30 Gy. Other radiation dose prescriptions may have different thresholds from the prescription in FIG. 3A, since different types of tumors may require different levels of irradiation for eradication, and different types of organs may have different sensitivities to radiation exposure. In some variations, the amount of radiation to be applied to a PTV may be determined, at least in part, on patient parameters measured before or during a treatment planning session. For example, tumors with areas of hypoxia may require greater levels of radiation for eradication as compared to tumors that do not have hypoxic areas. In the treatment planning session, if measured patient parameters (e.g., PET tracer SUV uptake) indicate that a PTV has one or more hypoxic areas, the radiation dose prescription may specify that a larger proportion of that PTV be irradiated with higher levels of radiation than if that PTV had no hypoxic regions.

A treatment planning system may generate a treatment plan that aims to deliver radiation dose levels to patient ROI or target regions as specified in the radiation dose prescription, and in accordance with the patient parameters measured before or during the treatment planning session. Changes to the patient parameters in the time between treatment planning and the treatment session may affect the efficacy of the treatment plan. Examples of patient parameter changes that may affect the efficacy of a treatment plan may include, but are not limited to, position(s) and/or distance(s) of target regions relative to irradiation-avoidance regions, shape and size of the target regions and/or irradiation-avoidance regions, as well as any of the biological activity and/or physiological parameters described previously, such as SUV of tracers and/or tracer activity (e.g., PET tracers, tumor-specific tracers, etc.).

A method for evaluating whether a treatment plan delivers the prescribed dose distribution may comprise acquiring imaging data on the day of the treatment, but before the start of treatment (e.g., before the first radiation beam is fired).

This imaging data may be referred to as pre-scan data, and a controller may extract biological activity and/or physiological and/or anatomical data from the pre-scan data. The extracted biological activity and/or physiological and/or anatomical data may be used to calculate at the start of a treatment session whether the current treatment plan would provide adequate dose to a target region. For example, a controller processor may simulate/calculate a dose distribution map or dose value histogram (DVH) based on the imaging data, the extracted biological activity and/or physiological and/or anatomical data, and the current treatment plan. Depending on whether the simulated dose distribution map or DVH meet certain criteria or thresholds, the controller and/or clinician may determine whether the treatment plan should be updated. For example, if the expected dose to be delivered to 95% of the volume of the simulation drops below the acceptable range of doses, either the volume definition or dose to be delivered may be altered to bring the constraint back to within tolerances. Alternatively or additionally, this method may also be used during a treatment session or after a treatment session to evaluate the efficacy of a treatment plan in light of real-time acquired imaging data. Some variations of the method may comprise calculating a range of acceptable clinical parameters during a treatment planning session (e.g., at the time the treatment plan is calculated), and the extracted biological activity and/or physiological and/or anatomical data from pre-scan imaging data and/or treatment session imaging data may be compared to the range of acceptable clinical parameters. The range of acceptable clinical parameters may be determined based on data acquired during a diagnostic imaging session, treatment planning session, and/or at the start of a treatment session (e.g., during a patient prescan), and/or may be a known or widely accepted range of normal activity. If the extracted data is within the range of acceptable clinical parameters, the controller and/or clinician may determine that it is appropriate to proceed with the current treatment plan, without requiring the controller processor to simulate or calculate a dose distribution map or DVH at the time of treatment. By reducing the time it takes to determine whether to proceed with the current treatment plan, the latency between the acquisition of imaging data and the application of therapeutic radiation may be reduced. Examples of clinical parameters for which an acceptable range may be calculated in advance of a treatment session may include position of target regions relative to the location(s) of OAR(s), the shape and volumes of the target region(s), SUV of the target regions, PET tracer activity at the target regions and/or OAR(s), and the like.

Alternatively or additionally to calculating a range of acceptable clinical parameters during a treatment planning session, a range of acceptable treatment plan quality parameters may be calculated. Treatment plan quality parameters may be any metric that assesses how well a particular treatment plan provides a desired radiation dose to target regions while sparing non-target regions (e.g., radiation-sensitive regions and/or normal tissue regions). Examples of plan quality scores or plan quality indices (PQI) are depicted in the table in FIG. 3B, and may include dose distribution indices or parameters that represent tumor dose coverage, DV relationships for the target regions or ROIs, conformity indices, homogeneity and dose gradient indices, etc. Target volume or TV may be the total volume of the ROI (e.g., the planning target volume PTV or gross tumor volume or GTV), and some PQI may specify the proportion of the TV and/or absolute volume of the TV (e.g., in cc) that is to be irradiated with a specified radiation level. The Dvv index of a treatment plan may represent the predicted/calculated level of irradiation of a portion vv of the TV (e.g., percent of total TV or absolute volume in cc) as result of radiation delivery according to that treatment plan. For example, a treatment plan with a Dvv index of D95%=45 Gy indicates that 95% of the TV will be irradiated with 45 Gy if radiation delivery proceeds according to the treatment plan. The Vdd index of a treatment plan may represent the portion of the TV (e.g., percent of total TV or absolute volume in cc) that is predicted/calculated to receive a dose dd (e.g., percent of total target dose or absolute dose in Gy) as a result of radiation delivery according to the treatment plan. For example, a treatment plan with a Vdd index of V20Gy=40% indicates that 40% of the TV will be irradiated with 20 Gy if radiation delivery proceeds according to the treatment plan. Another example of a PQI may include the conformity index CI, which represents the ratio of the volume of the PTV to the volume covered by the prescription isodose. CI may specify how tightly a particular target is covered by the prescription isodose. Numerically, the closer the ratio is to one, the more conformal the plan is. In the ideal case, the PTV volume closely approximates the prescription isodose volume, in which case the CI=1. A clinician may be willing to accept the plan if the CI is within a certain acceptable range, for example from 1 to 1.2. If the CI>1.2 the clinical may require replanning (i.e., re-calculating the treatment plan) using different constraints. Another example of a PQI is the Dose Gradient Index (DGI)=ratio of V50 to PTV, where V50 is the volume subtended by the 50% isodose. The ideal plan would have the gradient around targets very high, meaning that the V50 should be as close to PTV as possible. So the closer DGI is to 1 the higher the gradient, with the consequence of higher doses concentrated around targets, with the fast dose fall of away from the target. A clinician may set the range for DGI to be <2. This would mean that the V50 volume must not exceed twice the PTV in order to proceed with the treatment plan. Other examples of plan quality indices may include a mean dose metric (e.g., the average radiation dose delivered over a PTV), a homogeneity index (e.g., the magnitude of the dose variation across a PTV), global maximum location (e.g., location of the patient region receiving the highest radiation dose), and the like. Another example of PQI is a combined PQI, which may be constructed as a function of different individual PQIs or forms of PQIs listed in FIG. 3B. In this example, each PQI may be made unitless and may be represented by a formula that gives a value of 1 or less than 1. For example:

$$PQI_{combined} = \sqrt{\sum_i w_i \cdot p_i^2}$$

where $w_i$ are user defined weights for each $p_i$ (form of a PQI), and $p_i$ is the i-th form of a PQI, given by for example:

$$p_1 = CI - 1$$

where CI is given by:

$$CI = \frac{PTV}{TV}$$

or some other expression of a conformity index. Other forms of $p_i$ are, for example, a variation of a heterogeneity index HI:

$$p_2 = HI_2 = \frac{D1 - D99}{D_{norm}}$$

where $D_{norm}$ may be equal to the target prescription dose or any other user selected dose level, e.g. D50. D1 and D99 in the above equation may also be replaced with D2 and D98, respectively, or other user selected dose levels.

Another $p_i$ may use dose gradient index DGI:

$$p_3 = DGI - 1$$

where DGI may use the following definitions:

$$DGI_1 = \frac{V50}{V100}$$

or $$DGI_2 = \frac{V50}{PTV}$$

Note that (CI−1) is used as $p_1$, as CI may be greater or less than 1, but in an ideal scenario CI=1, so $(CI-1)^2$ measures the deviation from the ideal case. There may be other PQI and different mathematical forms of PQI combinations used to define a combined PQI, for example instead of a square root of sum of weighted squares, a simple weighted sum of forms of PQIs may be used to represent the combined PQI The goal of the combined PQI is to judge the overall quality of a treatment plan.

In some variations, a desired dose distribution may be imposed as a constraint on the treatment planning system and may be represented by a constraint on a PQI. For example, a prescription for 98% of a PTV to receive a dose of at least 50 Gy may be referred to as a PQI constraint: PTV D98=50 Gy. A constraint on the maximum amount of radiation that may be delivered to a lung region may be represented as D(1000 cc)<13.5 Gy. These constraints may facilitate generation of a treatment plan that aims to meet the desired dose distribution and/or clinical goals.

The efficacy of a treatment plan may vary depending on the characteristics of the patient and/or target regions, which may change between the treatment planning session and the treatment session, and/or even during a treatment session. That is, a treatment plan that may provide an acceptable radiation dose or distribution based on one set of patient or target region characteristics at a particular point in time may not provide an acceptable radiation dose or distribution if there are changes to any of those characteristics at a different point in time. Some variations may include calculating, at the time of treatment plan generation, the range of biological activity and/or physiological parameters within which a treatment plan would provide an acceptable dose or distribution (i.e., within which a treatment plan would meet PQI index thresholds). Alternatively or additionally, methods may include calculating PQI values based on real-time imaging data acquired at the time of treatment. Imaging data, and/or biological activity and/or physiological data extracted from the imaging data, and/or calculated PQIs, and/or ranges of acceptable clinical parameters and/or any recommendations on whether to proceed with a treatment plan may be presented to the clinician on a display. The clinician may then consider these parameters and data, and decide whether to initiate or continue a treatment session with the current treatment plan or to adapt or update the treatment plan to account for changes in the patient and/or target regions. In some variations, the radiation treatment system may proceed to apply radiation in accordance with a treatment plan if biological activity and/or physiological data, and/or treatment plan quality indices calculated based on real-time acquired data are within a prescribed or pre-determined range. The methods for evaluating treatment plans described herein may be used before, during and/or after a treatment session to determine whether to continue radiation treatment according to a current treatment plan or to update/adapt the treatment plan to account for changes in the patient and/or target region that may render the current treatment plan undeliverable and/or ineffective.

Evaluating Treatment Plans Using Plan Quality Indices (PQIs)

Figures 4A, 4B:
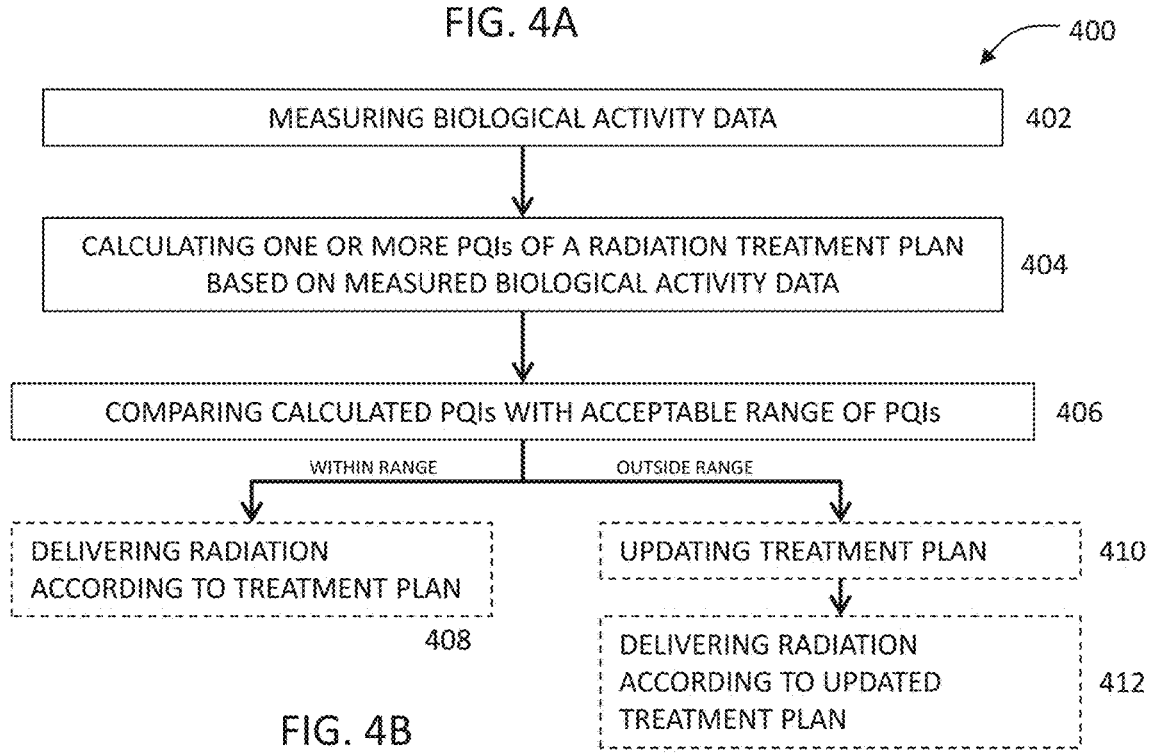
FIG. 4A depicts a table of example PQI values, prescribed PQI values, and a range of acceptable PQI values.
FIG. 4B depicts a flowchart representing one variation of a method for evaluating a treatment plan using PQI values calculated based on real-time acquired imaging data.

One variation for evaluating a treatment plan based on real-time acquired imaging data and/or biological activity and/or physiological data extracted from the imaging data is depicted in FIGS. 4A-4B. This method may comprise calculating a PQI of the current treatment plan based on clinical parameters (such as biological activity and/or physiological and/or anatomical data) acquired at the time of treatment. The PQI calculated based on real-time clinical parameters may be compared with a predetermined range of acceptable PQI values and if the calculated PQI is within the range, the treatment system may recommend to the clinician and/or technician that radiation treatment may proceed according to the current treatment plan. The range of acceptable PQI values may be determined based on data acquired during a diagnostic imaging session, treatment planning session, and/ or at the start of a treatment session (e.g., during a patient prescan), and/or may be a known or widely accepted range of PQI values. If the calculated PQI is not within the predetermined range of acceptable PQI values, the treatment system may recommend or alert to the clinician and/or technician update the treatment plan. FIG. 4A is table that provides examples of PQIs: the prescribed PQI value according to the physician's prescription and satisfied by the dose calculation during the treatment planning session ("Prescribed PQI" column) and the PQI MAPO values that would be acceptable for treatment at the time of treatment ("PQI MAPO" column). The ranges in FIG. 4A may vary for each patient, and/or target region, and/or treatment session, etc. For example, the original prescription may specify that at least 99% of the PTV (planning treatment volume) is irradiated or "covered" with the isodose surface corresponding to 90% of the prescription dose (V90%=99%) (first row and second column of FIG. 4A table). However, at the time of treatment, based on real-time acquired imaging data, calculations based on the patient clinical parameters may determine that the 90% isodose surface would enclose or cover only 96% of the target region (V90%=96%). Since this V90% value (96%) is within the MAPO range specific in the rightmost column (i.e., greater than 95%), the treatment system may recommend that treatment proceed in accordance with the treatment plan. As another example, the table of FIG. 4A may specify that the physician's prescription calls for less than 10% of the lung volume to be irradiated with a radiation dose of 20 Gy or more (i.e., Lung V20Gy<10%). However, at the time of treatment, measured changes in patient clinical parameters may indicate that the if the treatment plan were delivered without any adaptation, then as much as 23% of the lung volume would receive a radiation dose of 20 Gy or more (V20Gy=23%). This increase in lung volume irradiation to 23% may be the result of, for example, a changed tumor location within the lung. However, because this V20Gy value of 23% is not within the MAPO range (i.e., exceeds the MAPO value of 15%) the clinician may be alerted that the V20 PQI would be violated should the plan be delivered without any adaptation or change. Additional PQI and/or treatment plan quality parameters may be included in a table similar to the table depicted in FIG. 4A and provided to a radiation treatment system controller. In some variations, a table similar to the table of FIG. 4A may be generated for each target region and/or OAR. Optionally, a clinician and/or technician may be presented with the data in a table like this, or any other graphical representation. Clinicians may prefer evaluating a treatment plan using PQI values because PQI values may intuitively reflect changes in tumor coverage, conformity, dose-volume limits, and may be expressed or represented in a similar format as a radiation therapy prescription.

FIG. 4B depicts a flowchart diagram of one method for evaluating a treatment plan using on PQIs calculated based on real-time acquired imaging data and a current treatment plan. Method 400 may be performed by a controller of the radiation treatment system at the time of treatment (e.g., on the day of treatment, before the firing of the first radiation beam and/or during the application of radiation beams) and/or after the treatment session (i.e., to determine whether to use the same treatment plan for the next treatment session). Method 400 may comprise measuring 402 biological activity and/or physiological and/or anatomical data (and/or any other patient or target region data) at the beginning and/or during a treatment session. As described herein, measuring biological activity and/or physiological and/or anatomical data may comprise acquiring imaging data, such as PET data, SPECT data, X-ray or CT, data, MRI data, etc. In some variations, measuring biological activity data may comprise acquiring a CT or PET-CT image. Biological activity, and/or physiological and/or anatomical data may be extracted or calculated based on the acquired imaging data. Method 400 may then comprise calculating 404 one or more PQIs based on the measured data and comparing 406 the calculated one or more PQIs with their corresponding acceptable ranges of values. In some variations, updated PQI values may be calculated by performing a dose calculation for any altered geometry of target regions or changes in other non-geometric clinical parameters (e.g., biological activity and/or physiological data) that may be used in calculating delivered dose distributions. Example of non-geometric clinical parameters may include, but are not limited to, PET SUV of the target regions and/or PET activity changes in those target regions. The acceptable ranges for each of the PQIs may be predetermined by a clinician, for example, during a treatment planning session and may be transferred to the treatment system. The clinician and/or technician may determine whether to proceed with a treatment plan based on the comparison from step 406.

Optionally, if the calculated PQIs are within the acceptable ranges, method 400 may comprise delivering 408 radiation according to the treatment plan. If the calculated PQIs are not within the acceptable ranges, method 400 may optionally comprise updating 410 the treatment plan and delivering 412 radiation according to the updated treatment plan. Alternatively, method 400 may comprise terminating the treatment session, and updating the treatment plan for a future session. In situations where some of the one or more PQIs are within their corresponding desired ranges and one or more PQIs are not within their corresponding desired ranges, the decision of whether or not to proceed with a treatment plan may be subject to a clinician's discretion. Alternatively or additionally, method 400 may comprise a rubric that prioritizes and/or ranks the different PQIs. For example, a recommendation on whether to proceed with a treatment plan may be based on a weighted sum of the PQIs, where deviations from a highly-weighted (e.g., relatively more important) PQI may offset compliance within lower-weighted (e.g., relatively less important) PQI. In some variations, as long as highly-weighted PQIs are within the desired or prescribed range, even if some lower-weighted PQIs are out-of-range, the controller may recommend that radiation delivery should proceed according the treatment plan.

Evaluating Treatment Plans Using Clinical Parameters

Figures 5A, 5B:
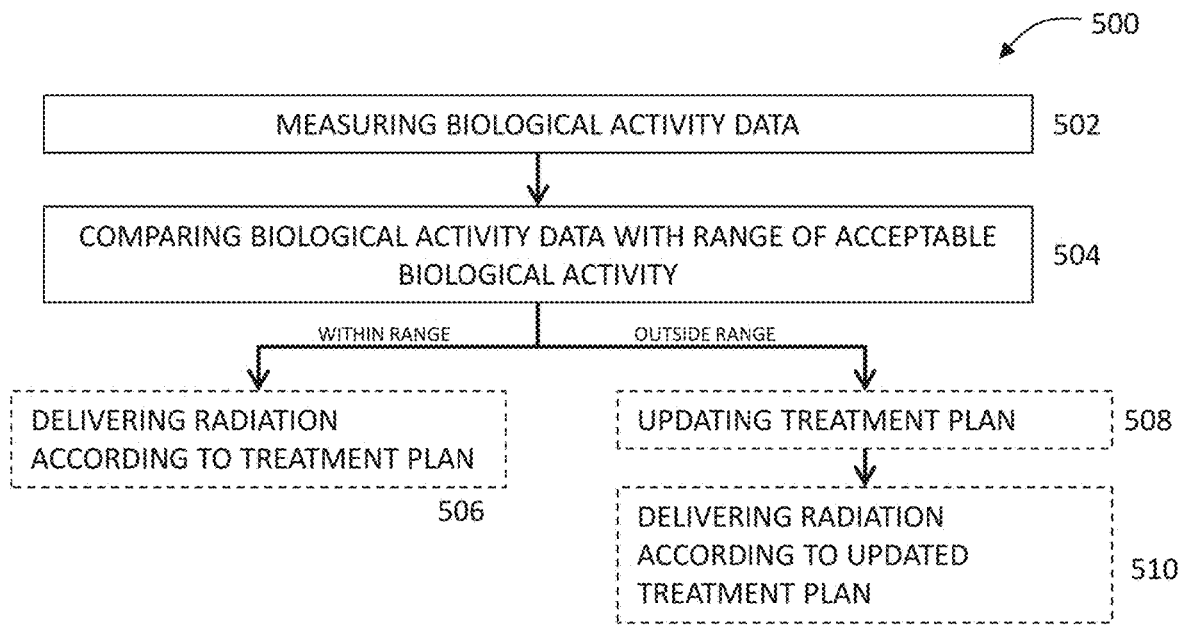
FIG. 5A depicts a table of example clinical parameters and PQI values calculated during a treatment planning session and at the time of treatment.
FIG. 5B depicts a flowchart representing one variation of a method for evaluating a treatment plan using clinical parameters derived from real-time acquired imaging data.

FIGS. 5A-5B depict another variation of a method for evaluating a treatment plan based on real-time acquired imaging data and/or biological activity and/or physiological data extracted from the imaging data. This method may comprise calculating a range of acceptable clinical parameters (e.g., a range of acceptable biological activity, physiological, and/or anatomical data) before a treatment session (e.g., during a treatment planning session). At the time of treatment, biological activity and/or physiological data extracted from real-time acquired imaging data may be compared with the range of acceptable clinical parameters. The range of acceptable clinical parameters may be calculated or derived by setting a range of desired PQI values (e.g., a minimum PQI value) and iteratively calculating the corresponding range of acceptable clinical parameters (e.g., incrementing and/or decrementing the one or more clinical values and re-calculating the treatment plan quality indices until the calculated PQI is out-of-range). Alternatively or additionally, clinicians may specify a range of acceptable clinical parameters within which the patient is eligible to receive radiation treatment. In some variations, the range of acceptable clinical parameters may be determined based on data acquired during a diagnostic imaging session, treatment planning session, and/or at the start of a treatment session (e.g., during a patient prescan), and/or may be a known or widely accepted range of normal activity.

FIG. 5A is a table that provides examples of clinical parameters and their acceptable/desired value range(s) ("Clinical Parameter Change" column), acceptable PQI for that range of acceptable clinical parameters ("PQI" column), PQI during a treatment planning session ("PQI on day of simulation" column), and PQI at a treatment session ("PQI on day of first treatment" column). The table maps changes in clinical parameters to changes in PQI values. A clinician and/or treatment system controller may determine whether the changes in PQI values are acceptable for proceeding with delivering radiation according to the current treatment plan. For example, it may be calculated that if the distance between the center of the PTV and spinal cord at the time of treatment is 3 mm less than the distance as measured during the treatment planning session, the PQI may increase from 29 Gy to 31 Gy (that is, the spinal cord will be exposed to more radiation than expected). A clinician may determine, at the time of treatment, whether this is acceptable for proceeding with treatment. Alternatively, a clinician may determine prior to the treatment session a range of acceptable PQI values so that as long as the PQI values on the day treatment are within the range of acceptable PQI values, the patient may proceed with treatment.

FIG. 5B depicts a flowchart diagram of one method for evaluating a treatment plan using on clinical parameters extracted from or calculated based on real-time acquired imaging data and a proposed/current treatment plan. Method 500 may comprise measuring 502 biological activity and/or physiological and/or anatomical data (and/or any other patient or target region data) at the beginning and/or during a treatment session. As described herein, measuring biological activity and/or physiological and/or anatomical data may comprise acquiring imaging data, such as PET data, SPECT data, X-ray or CT, data, MRI data, etc. In some variations, measuring biological activity data may comprise acquiring a CT or PET-CT image. Biological activity, and/or physiological and/or anatomical data may be extracted or calculated based on the acquired imaging data. Examples of such data may include, but are not limited to, the size, shape and location of target regions, as well as any non-geometric clinical parameters such as PET SUV of the target regions and/or PET activity changes in those target regions. Method 500 may then comprise comparing 504 the biological activity and/or physiological and/or anatomical data (which may, as a group, be referred to as clinical parameters) with a range of acceptable values. The acceptable ranges for each of the clinical parameters may be predetermined by a clinician, for example, during a treatment planning session and may be transferred to the treatment system. The clinician and/or technician may determine whether to proceed with a treatment plan based on the comparison from step 504. Optionally, if the biological activity and/or physiological and/or anatomical data are within the acceptable ranges, method 500 may comprise delivering 506 radiation according to the treatment plan. If the biological activity and/or physiological and/or anatomical data are not within the acceptable ranges, method 500 may optionally comprise updating 508 the treatment plan and delivering 510 radiation according to the updated treatment plan. Alternatively, method 500 may comprise terminating the treatment session, and updating the treatment plan for a future session. In situations where some of the biological activity and/or physiological and/or anatomical data are within their corresponding desired ranges and others are not within their desired ranges, the decision of whether or not to proceed with a treatment plan may be subject to a clinician's discretion. Alternatively or additionally, method 500 may comprise a rubric that prioritizes and/or ranks the different biological activity and/or physiological and/or anatomical data. For example, a recommendation on whether to proceed with a treatment plan may be based on a weighted sum of the biological activity and/or physiological and/or anatomical data, where deviations from a highly-weighted (e.g., relatively more important) biological activity and/or physiological and/or anatomical data may offset compliance within lower-weighted (e.g., relatively less important) biological activity and/or physiological and/ or anatomical data. In some variations, as long as highly-weighted biological activity and/or physiological and/or anatomical data are within the desired or prescribed range, even if some lower-weighted biological activity and/or physiological and/or anatomical data are out-of-range, the controller may recommend that radiation delivery should proceed according the treatment plan. Evaluating treatment plans based on clinical parameters may streamline the latency between the acquisition of real-time imaging data and radiation delivery by not calculating PQI values of the treatment plan, recontouring the target regions, and/or calculating dose distributions during a treatment session. This may help to reduce the treatment session time for the patient.

Figure 5C:
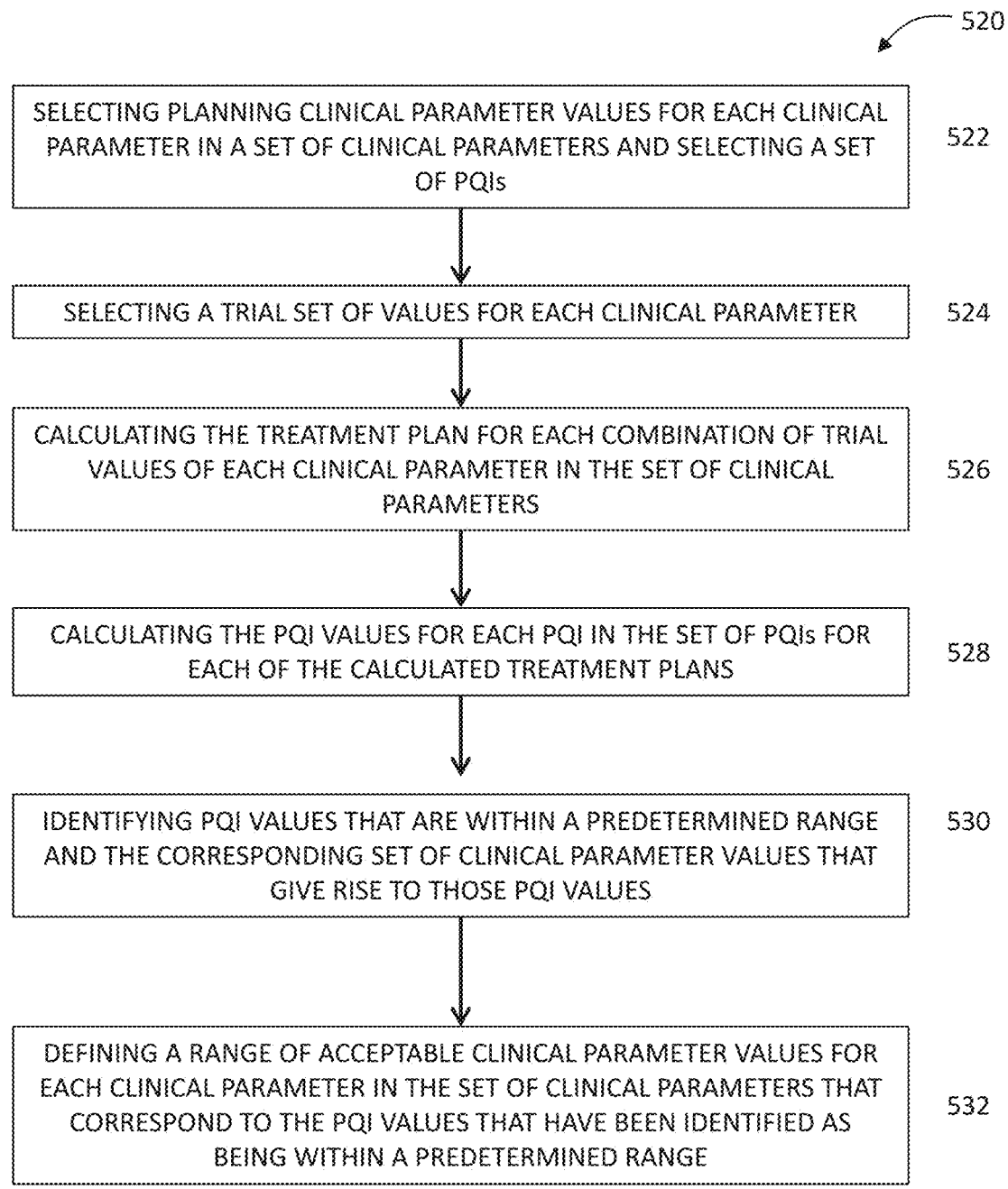
FIG. 5C depicts a flowchart representing one variation of a method for calculating a range of acceptable clinical parameters.
Figure 5D:
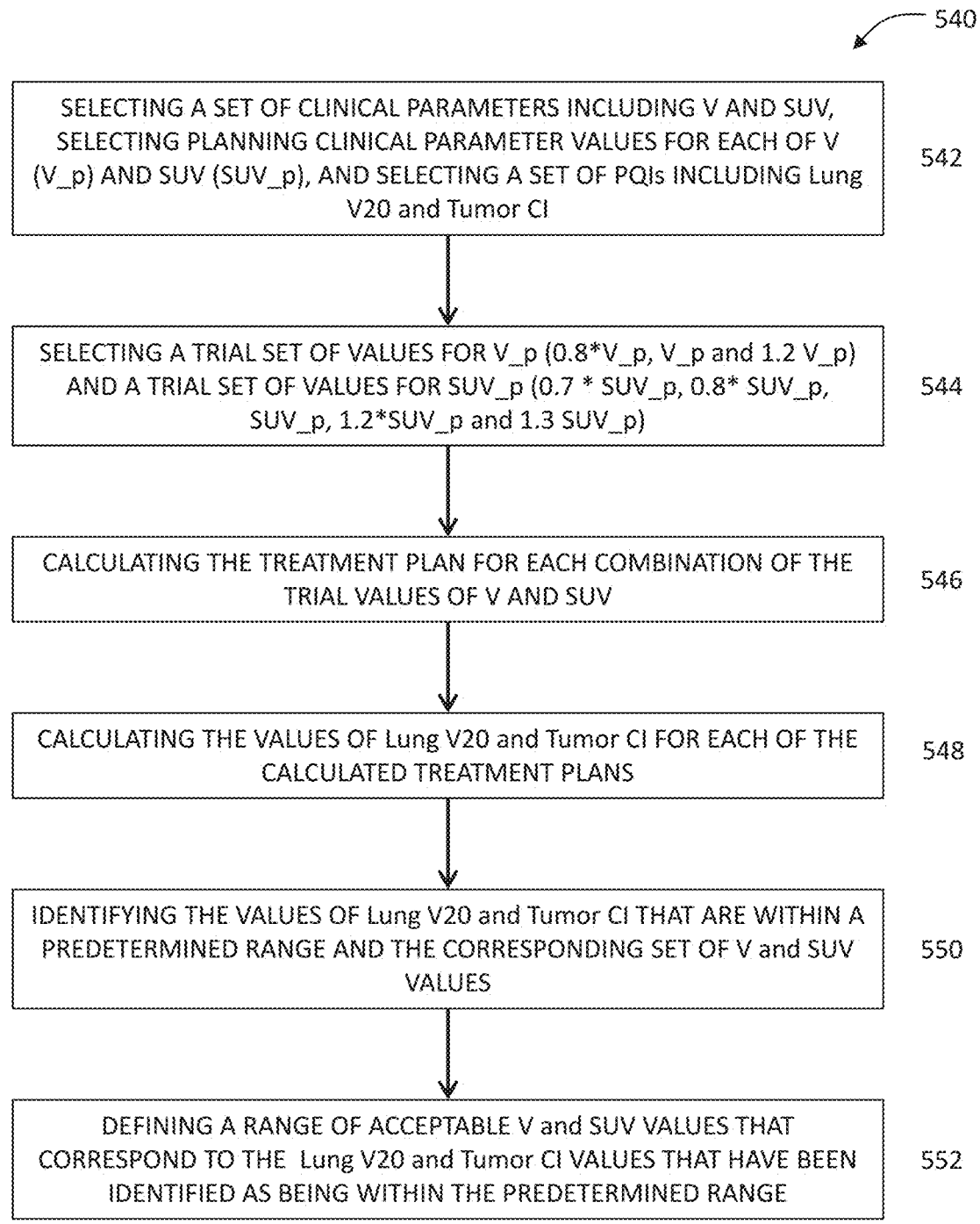
FIG. 5D depicts a flowchart representing one variation of a method for calculating a range of acceptable clinical parameters.

One variation of a method for calculating a set or range of acceptable biological activity levels based on a set of acceptable PQI values is depicted in FIG. 5C. FIG. 5D depicts an example of the method of FIG. 5C applied to a set of clinical parameters that include tumor size (V) and tumor SUV (SUV), and a set of PQIs that include Lung V20 and PTV CI. A clinician may determine that a treatment plan is appropriate for delivery if a set of clinical parameters measured at the time of treatment are within a range that such that a set of corresponding PQI values would also be within a corresponding acceptable range. The clinician may determine, for example, that possible range of acceptable clinical parameter values may be about ±20% from the planning tumor size (V_p) and about ±30% of the planning tumor SUV (SUV_p). The clinician may input clinical parameter values within these ranges into the treatment planning system to determine the range of acceptable PQI values for lung V20 and PTV CI that would correspond with the range of acceptable clinical parameter values. FIG. 5C depicts one method 520 for determining the range of acceptable clinical parameter values. The method 520 may comprise selecting 522 planning clinical parameter values for each clinical parameter in a set of clinical parameters, selecting 524 a trial set of values for each clinical parameter, calculating 526 the treatment plan for each combination of trial values of each clinical parameter in the set of clinical parameters, calculating 528 the PQI values for each PQI in the set of PQIs for each of the calculated treatment plans, identifying 530 PQI values that are within a predetermined range and the corresponding set of clinical parameter values that give rise to those PQI values, and defining 532 a range of acceptable clinical parameter values for each clinical parameter in the set of clinical parameters that correspond to the PQI values that have been identified as being within a predetermined range. Defining a range of acceptable clinical parameter values for a particular PQI may comprise identifying the lowest clinical parameter value that gives rise to a PQI value that is within the predetermined range and identifying the highest clinical parameter value that gives rise to a PQI value that is within the predetermined range. The calculated ranges for each clinical parameter in the set of clinical parameters (e.g., ranges of V_p and SUV values that are within (e.g., satisfy) the range of PQI values) may be the set of acceptable clinical parameter values at the time of treatment to be used for making a treat or no-treat decision at the time of treatment. That is, at the time of treatment, if the measured clinical parameter is within that range (i.e., greater than or equal to the lowest clinical parameter value and less than or equal to the highest clinical parameter value). Because the range of acceptable clinical parameters is computed prior to the treatment session, this may help to reduce the latency between acquiring imaging data and deciding whether to proceed with a treatment plan. In some variations, a controller of the treatment system may decide whether to proceed with a treatment plan by comparing extracted patient data (e.g., biological activity data, and/or physiological data, and/or anatomical data) with the range of acceptable clinical parameters. In some variations, a clinician is notified when one or more extracted patient data is out-of-range from the acceptable clinical parameters, so that a final decision can be made on whether to proceed with treatment and/or whether the treatment plan is to be updated or adapted.

FIG. 5D depicts a method 540 for identifying a range of acceptable values for tumor volume V and tumor SUV such that a set of PQIs including Lung V20 and Tumor CI have values that are within an acceptable range. The method 540 may comprise selecting 542 a set of clinical parameters and a set of PQIs for evaluation. The value of V based on the treatment plan is V_p and the value of SUV based on the treatment plan is SUV_p. The method 540 may comprise selecting 544 trial values for V and SUV for the V_p parameter from a range of possible parameter values. For example, trial values for V may include 0.8*V_p, V_p and 1.2 V_p, which correspond to about a ±20% increase and decrease in the tumor volume from the volume at the time of planning. Trial values for SUV may include 0.7*SUV_p, 0.8*SUV_p, SUV_p, 1.2*SUV_p and 1.3 SUV_p. A plan may be calculated 546 for each combination of trial V values and trial SUV values (giving rise to a set of calculated plans), and calculating 548 the values of Lung V20 and Tumor CI for each of the calculated plans. The method may further comprise determining which combinations of V_p and SUV values result in PTV CI and Lung V20 values within an acceptable range. For example, the method may comprise 550 identifying the values of Lung V20 and Tumor CI that are within a predetermined range, and which combinations of V_p and SUV values result in PTV CI and Lung V20 values that fall outside of the acceptable range. Next, the method may comprise defining 552 a range of acceptable V values and SUV values that correspond with Lung V20 and Tumor CI values that have been identified as being within the predetermined range (e.g., ranges of V and SUV that satisfy the range of PQI values). Defining the range of acceptable values of V and SUV may comprise identifying the lowest and highest V and SUV values that give rise to Lung V20 and Tumor CI values that are still within a predetermined/acceptable range.

Figure 6A:
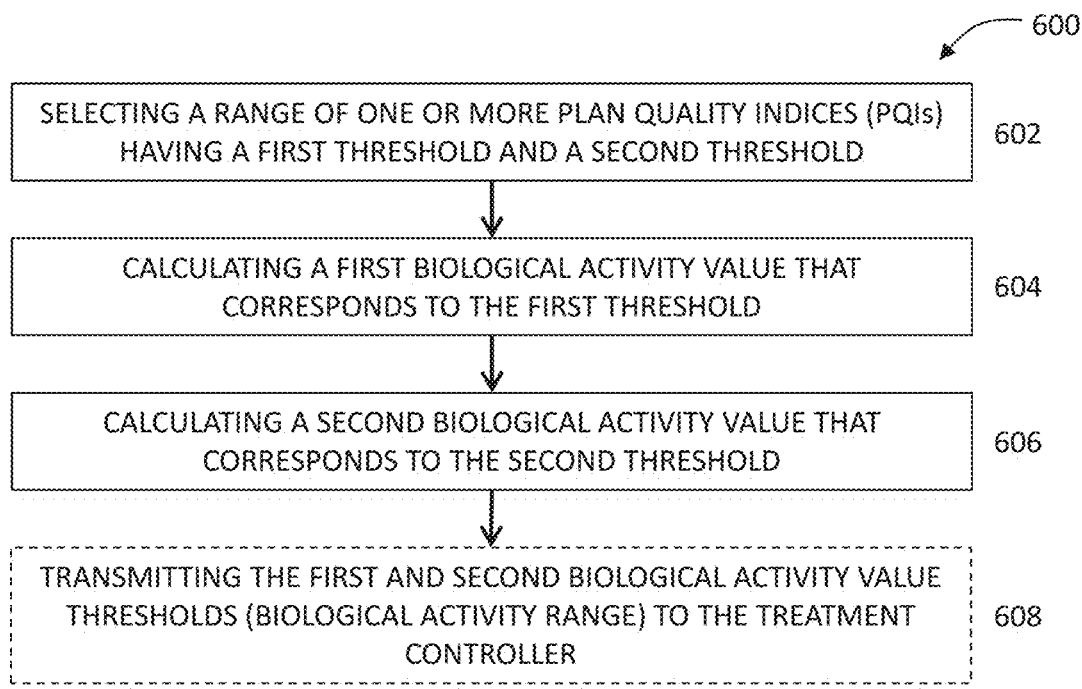
FIG. 6A depicts a flowchart representing one variation of a method for calculating a range of acceptable biological activity values based on a selected range of PQI values.
Figure 6B:
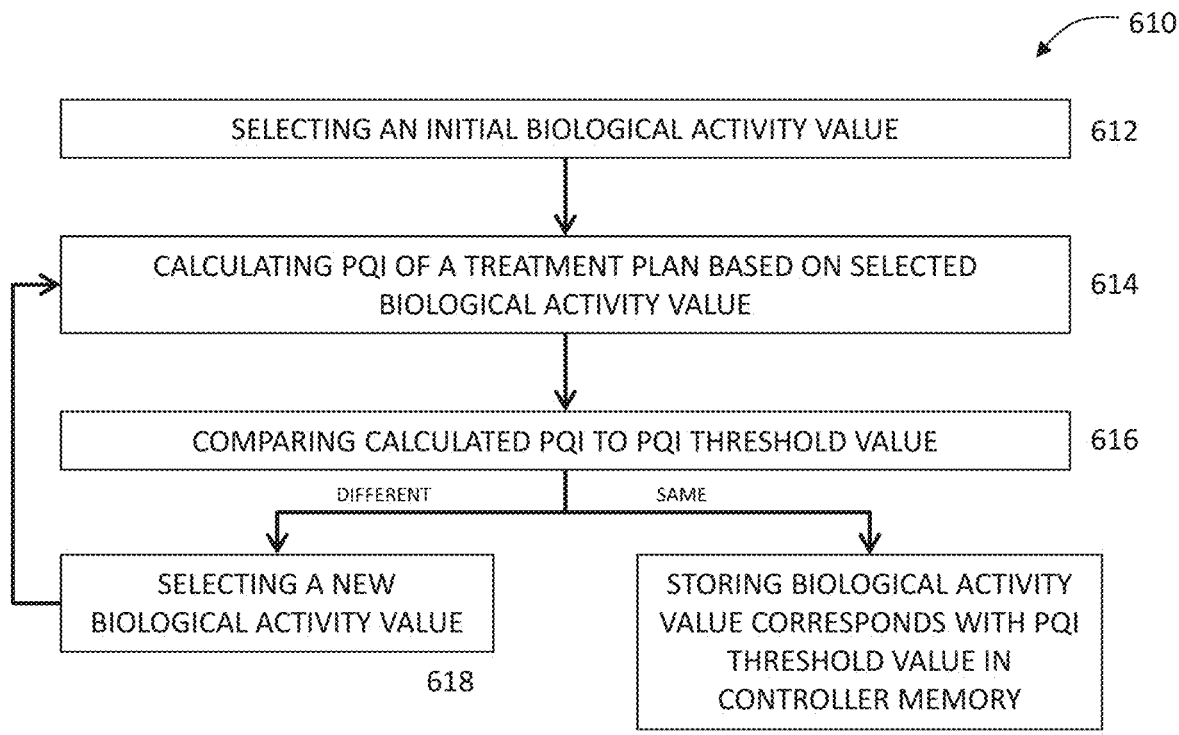
FIG. 6B depicts a flowchart representing another variation of a method for calculating a range of acceptable biological activity values based on selected PQI threshold values.

FIGS. 6A and 6B depict methods for calculating a range of acceptable PQIs for use in the methods described above. FIG. 6A depicts one method 600 for generating a range of biological activity levels or values that map to a range of desired PQI values. At the time of treatment, acquired biological activity and/or physiological and/or anatomical data may be compared to this generated range of biological activity levels or values, as described above. Alternatively or additionally, a range of acceptable biological activity or values may be determined based on data acquired during a diagnostic imaging session, treatment planning session, and/or at the start of a treatment session (e.g., during a patient prescan), and/or may be a known or widely accepted range of normal activity. Method 600 may comprise selecting 602 a range of one or more PQIs having a first threshold PQI value and a second threshold PQI value, calculating 604 a first biological activity value that corresponds to the first threshold PQI value, and calculating 606 a second biological activity value that corresponds to the second threshold PQI value. Optionally, method 600 may comprise transmitting 608 the first and second biological activity value thresholds (biological activity range) to the treatment system controller. Method 600 may also be used to generate a physiological data range and/or anatomical data range that map to a range of desired PQI values.

FIG. 6B depicts one variation of a method 610 for iteratively calculating a biological activity value that corresponds with a desired PQI value. Method 610 may comprise selecting 612 an initial biological activity value, calculating 614 a PQI of a treatment plan based on the selected biological activity value, and comparing 616 the calculated PQI to a desired PQI value (such as a desired PQI threshold value). If the calculated PQI does not match the desired PQI value, method 600 comprises selecting 618 a new biological activity value and repeating steps 614 and 616. Selecting a new biological activity value may comprise incrementing or decrementing the current biological activity value, depending on whether the calculate PQI was greater than or less than the desired PQI value. If the calculated PQI matches the desired PQI value (or is within a specified or acceptable tolerance or range of the desired PQI value), the controller may then store 620 the biological activity value in controller memory (e.g., controller of treatment planning system and/or controller of the treatment system). Method 610 may also be used to generate a physiological data value and/or anatomical data value that maps to a desired PQI value.

Evaluating Treatment Plans Using Bounded DVH

Figure 7A:
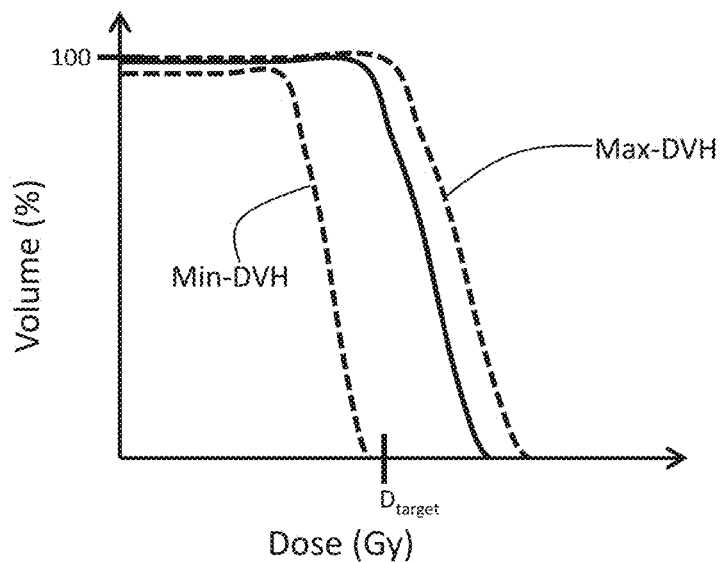
FIG. 7A depicts an example of a dose volume histogram (DVH) and a bounded DVH.

Alternatively or additionally to evaluating a treatment plan based on PQI values calculated based on real-time acquired biological activity and/or physiological and/or anatomical data, treatment plans may also be evaluated based on a dose-volume histogram or DVH. A DVH is a plot depicting the dose levels delivered to regions or proportions of a target volume. An example of a DVH plot is shown in FIG. 7A (solid line). In an ideal system, dose $D_{target}$ is delivered to 100% of the target volume, without any "hot spots" (i.e., regions of the target volume that receive a dose greater than $D_{target}$) and/or regions of the target volume that receive a dose less than $D_{target}$. However, in many cases, the dose $D_{target}$ is not delivered to 100% of the target volume (e.g., actual delivered dose may be greater than or less than $D_{target}$), but a range of delivered dose may be clinically acceptable. A DVH plot may be calculated during a treatment planning session based on patient parameters at that time point and a treatment plan. DVH plots may optionally be included as part of generating a treatment plan, such that treatment plans that do not have a desired DVH profile for one or more of the irradiation target regions may be updated or refined. A range of desired DVH profiles may be represented by a bounded DVH, represented by the dotted lines in FIG. 7A. A bounded DVH may be defined by minimum and maximum dose distributions. A treatment plan that results in a dose distribution between the minimum and maximum dose distributions may be considered acceptable for delivery. During a treatment planning session, bounded DVH curves may be generated for each ROI (e.g., volume of interest) or target region, based on biological activity and/or physiological and/or anatomical data acquired before or during the planning session. At the time of treatment, imaging data acquired in real-time may be used to calculate an updated DVH curve for one or more of the target regions. That is, changes in biological activity, and/or physiological and/or anatomical data may also alter the DVH curve for one or more target regions. The updated DVH curve may be compared to the bounded DVH curves. If it is within range, the treatment system controller and/or clinician may determine that radiation delivery may proceed according to the treatment plan. If it is not within range, the treatment system controller and/or clinician may decide to update the treatment plan before proceeding.

At the time of treatment, DVH curves may be calculated for all of the target regions based on real-time acquired imaging data. In some variations, real-time acquired imaging data may comprise PET imaging data (e.g., a PET prescan). A nominal DVH curve for the PTV, and/or biological guidance region of interest (BgROI) or radiation-firing zone (RFZ), and/or OAR may be calculated based on the PET imaging data. Other radiation delivery metrics, such as PTV or target coverage, mean activity in the BgROI/RFZ, mean SUV of the PTV, along with one or more normalization factors, may be calculated based on the PET imaging data. The DVH curves for some target regions may be within the range defined by the bounded DVH for those regions while the DVH curves for other target regions may not be within the bounded DVH range. The decision of whether or not to proceed with a treatment plan may be subject to a clinician's discretion. Alternatively or additionally, a rubric that prioritizes and/or ranks the different target regions may be generated during the treatment planning session and used to determine whether to proceed with a treatment plan. For example, a recommendation on whether to proceed with a treatment plan may be based on a weighted sum of the target regions, where an out-of-bound DVH curve for a highly-weighted (e.g., relatively more important) target region may offset a within-bound DVH curve for a lower-weighted (e.g., relatively less important) target region. In some variations, as long as the DVH curves for highly-weighted target regions are within the desired or prescribed bounds or ranges, even if the DVH curves for some lower-weighted target regions are out-of-bound, the controller may recommend that radiation delivery should proceed according the treatment plan.

Figure 7B:
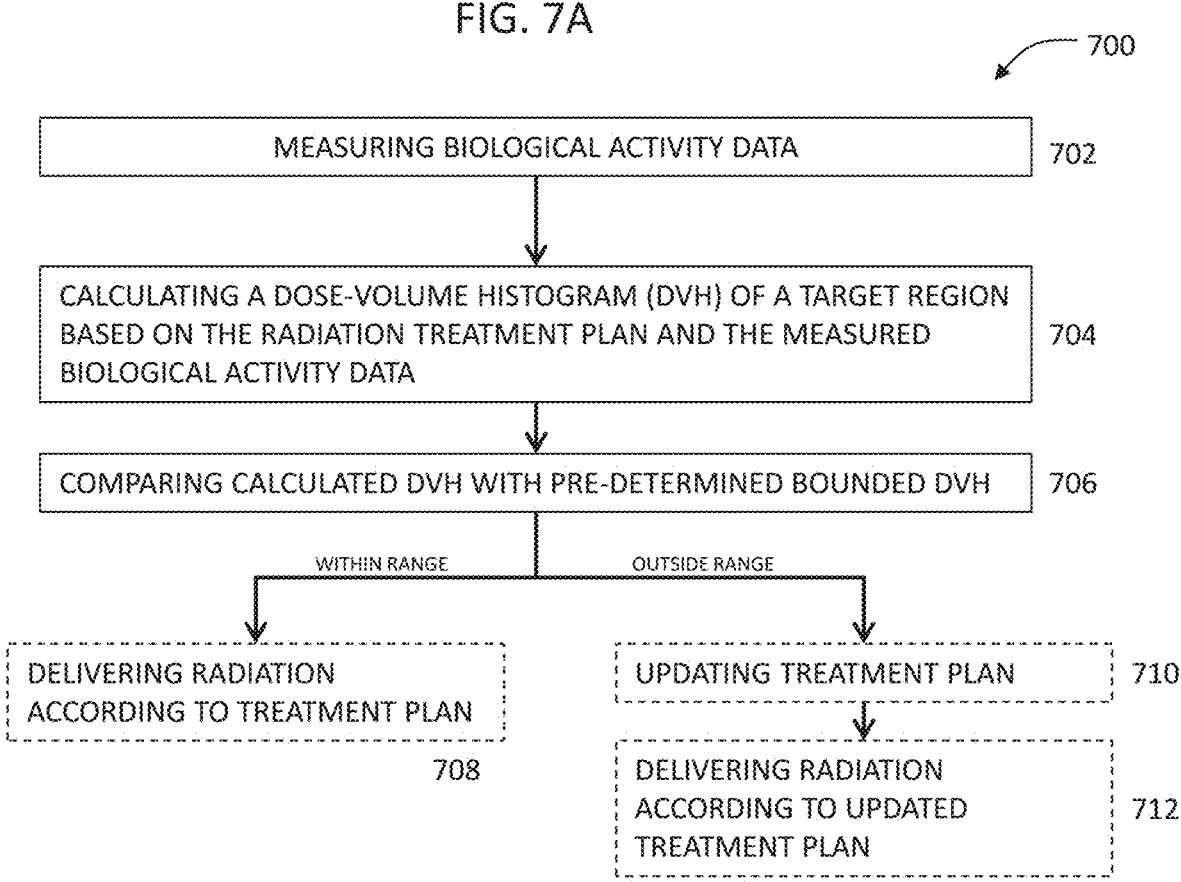
FIG. 7B depicts a flowchart representing another variation of a method for evaluating a treatment plan using a DVH derived from real-time acquired imaging data.

FIG. 7B depicts one variation of a method for evaluating a treatment plan using bounded DVH. While this method is depicted as evaluating the DVH for a single target region, it should be understood that this method may be used to evaluate the DVH for a plurality of target regions. The method may be performed at the start of a treatment session (e.g., before the first radiation beam is fired) and/or during a treatment session, as may be desired and described above. Method 700 may comprise measuring 702 biological activity data at the time of treatment. Measuring biological activity data may include measuring physiological and/or anatomical data, and/or may include acquiring imaging data from which biological activity and/or physiological and/or anatomical data may be calculated. Such data acquisition may take place at the start of a treatment session (e.g., before the first radiation beam is fired, during a pre-scan) and/or during the treatment session. (e.g., after the first radiation beam is fired). Method 700 may then comprise calculating 704 a DVH curve of a target region based on the radiotherapy treatment plan and the measured biological activity data and comparing 706 the calculated DVH curve with a pre-determined bounded DVH for that region. If the calculated DVH curve is within the bounded DVH, method 700 may optionally comprise delivery 708 radiation according to the treatment plan. If the calculated DVH curve is outside the bounded DVH, method 700 may optionally comprise updating 710 the treatment plan and optionally delivering 712 radiation according to the updated treatment plan. Alternatively, method 700 may comprise terminating the treatment session, and updating the treatment plan for a future session. Method 700 may optionally comprise comparing the deviations of DVH curves of all of the target regions and weighting the deviations according to a rubric or ranking of target regions. Computing a weighted sum of the all of DVH curve deviations may assist a clinician in determine whether to proceed with radiation delivery in light of certain DVH curves for certain target regions that are out-of-bounds from the bounded DVH.

Methods for Calculating Bounded DVH Curves

During treatment planning, bounded DVH curves may be calculated for each region-of-interest in the patient, i.e., each irradiation-target region and/or each irradiation-avoidance region. For example, bounded DVH curves may be calculated for a tumor region (i.e., gross tumor volume), and/or a PTV (i.e., gross tumor volume with a margin), and/or radiation-firing zone or RFZ (i.e., region that includes a potentially-moving PTV, and most or all of the likely positions of the PTV within the RFZ), and/or one or more OARs. In one variation, treatment planning may comprise calculating a radiation-firing matrix P based on, for example, one or more PET images X and/or a patient CT image (which may be referred to as planning images), where RFZ (e.g., target regions and/or PTVs) and/or OARs may be identified or outlined in the PET images X and/or the patient CT image (and/or other supplemental patient images in the same frame of reference). Optionally, additional data regarding the RFZ(s) and/or OARs such as their size, shape, location, and degree of radiation-sensitivity, maximum tolerable radiation exposure, and/or a prescribed radiation dose to be delivered to irradiation-target regions, and/or other dose constraints such as maximum and minimum dose delivered for each patient target region may also be used in the calculations of a radiation-firing matrix P. The planning patient CT image may also be used for dose calculations, for example, predicting the distribution of the delivered dose if radiation were applied to the patient according to the radiation-firing matrix P. A family of bounded DVH curves may be calculated for each OAR, RFZ, and/or PTV based on the radiation-firing matrix P by performing a rigid shift of the PET image X of the PTV within the RFZ, and calculating a corresponding dose to the OAR, RFZ, and/or PTV for that particular shifted PTV position. For example, for a patient with a PTV within a RFZ, and one OAR, a family of DVH curves for the PTV may be calculated for each shifted position of the PTV within the RFZ. Optionally, a second family of DVH curves for the RFZ and a third family of DVH curves for the OAR may be calculated for each shifts position of the PTV within the RFZ. A min-DVH curve may be derived from a family of DVH curves by extracting the left-most points of that family of DVH curves (i.e., for each dose value, selecting the point with the lowest volume fraction, or for each volume fraction, select the point with the lowest dose). A max-DVH curve may be derived from a family of DVH curves by extracting the right-most points of that family of DVH curves (i.e., for each dose value, selecting the point with the highest volume fraction, or for each volume fraction, select the point with the highest dose). Bounded DVH curves for a particular region of interest (e.g., PTV, RFZ, OAR) comprising min-DVH curve, max-DVH curve, and nominal DVH curve (e.g., dose calculated based on the planning images) may be transmitted from the treatment planning system to the radiation therapy system, and used to evaluate the treatment plan based on updated imaging data, and/or biological and/or physiological data.

Figure 8A:
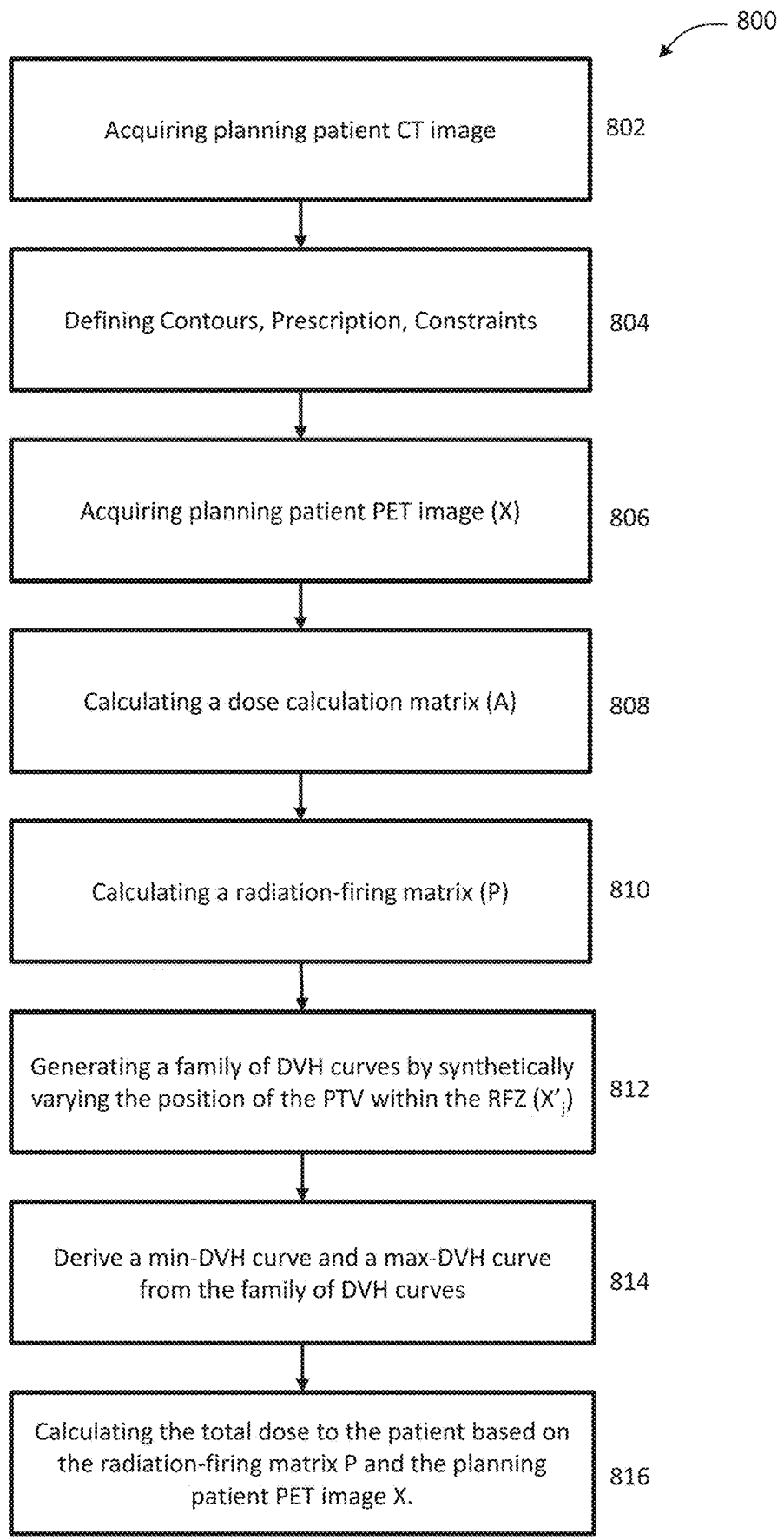
FIG. 8A depicts a flow chart representing one method of calculating bounded DVH curves that may be used to evaluate treatment plans based on biological and/or physiological data acquired at the time of treatment.

FIG. 8A is a flowchart depiction of one variation of a method for calculating bounded DVH curves during treatment planning. Method 800 may comprise acquiring 802 a patient CT image, defining 804 dose constraints, prescription, PTV and/or RFZ and OAR contours and other data, acquiring 806 patient PET image (X), calculating 808 a dose calculation matrix (A), and calculating 810 a radiation-firing matrix (P) that designates the conversion from imaging data to a fluence map that may include beamlet pattern and/or beamlet intensities to be applied to the patient during a treatment session. In some variations, acquiring a patient PET image 806 may occur before defining 804 dose constraints, prescription and/or contouring. Dose constraints, prescription(s) and/or contours may comprise specifying the minimum and/or maximum dose to certain patient regions (e.g., max dose to an OAR or an irradiation-avoidance region, minimum dose to a PTV or an irradiation-target region, fluence smoothness across different patient regions), specifying the total dose to be delivered to an irradiation-target region (e.g., 10 Gy per PTV), and/or contouring OARs and/or PTVs. Additional dose constraints are described below. Method 800 may comprise generating bounded DVH curves for each PTV and/or RFZ and/or OAR by generating 812 a family of DVH curves by simulating various positions and/or motions of the PTV within the RFZ by synthetically varying the image data $(X'_j)$ so that the PTV is located at various (j) positions in the RFZ (i.e., each DVH curve represents dose delivered where the PTV at a particular position within the RFZ). Bounded DVH curves comprise a min-DVH curve, nominal DVH curve, and a max-DVH curve for a particular PTV and/or RFZ and/or OAR. The min-DVH curve may be derived 814 by extracting the left-most points of that family of DVH curves (i.e., for each dose value, selecting the point with the lowest volume fraction), and the max-DVH curve may be derive 814 by extracting the right-most points of that family of DVH curves (i.e., for each dose value, selecting the point with the highest volume fraction). Optionally, method 800 may comprise calculating 816 the total dose to the patient if radiation were delivered based on the radiation-firing matrix P and the planning patient PET image X.

A dose calculation matrix A as calculated 808 in method 800 may map beamlet coefficients (e.g., fluence values) to dose values at a set of pre-selected regions in the patient (i.e., sampling points or voxels). Sampling points may include patient regions for which radiation delivery and dose may be monitored and/or patient regions of clinical interest. For example, sampling points may be selected within one or more (e.g., all) of the PTVs, OARs, and RFZs in a patient. The dose calculation matrix A may be an n×m matrix, where n corresponds to the number of sampling points in a patient, and m corresponds to the number of candidate beamlets available for delivering a unit of radiation. That is, the m entries along a particular column of the dose calculation matrix A may represent a dose contribution from a unity-weighted beamlet to each of the m sampling points or voxels. In some variations, the unit of radiation delivered by a candidate beamlet may be the radiation level delivered through a single MLC leaf opening at a particular firing position (e.g., gantry angle with respect to the radiation therapy system isocenter), at a particular patient platform position with respect to the therapeutic beam plane (e.g., beam station). The dose calculation matrix A may be calculated column-by-column, for example, by ray-tracing each beamlet's aperture (or trajectory) along the path through a RFZ or patient volume, and calculating the contribution of a unity-weighted beamlet to each of the n sampling points or voxels. A beamlet aperture may be a MLC aperture defined by a single MLC leaf opening (i.e., of a binary MLC or a 2-D MLC). Examples of dose calculation algorithms may include Monte-Carlo simulation, collapsed-cone convolution superposition, pencil-beam convolution, and others.

A radiation-firing matrix P may be a matrix that designates the conversion from imaging data to a fluence map that may include beamlet pattern and/or beamlet intensities to be applied to the patient during a treatment session. A radiation-firing matrix P may represent the relationship between a fluence map F for radiation delivery to a patient region and an image X of that patient region. That is, a radiation-firing matrix P may be any matrix such that y=P·X. A radiation-firing matrix P may be calculated by iteratively solving for a fluence map that minimizes one or more cost functions, for example, a cost function C(y) of a resulting dose distribution and fluence formed based on the radiation dose constraints and objectives described above. C may comprise a sum of penalty functions C=ΣC$_i$(y). Examples of penalty functions may include, but are not limited to, minimum dose to target region, average or maximum dose on OARs, and/or fluence smoothness, total radiation output, total tissue dose, treatment time, etc. Further examples of penalty functions may include penalty functions that encourage fluence smoothness ($C_i$=|L(y)|$_1$, i.e. a 1-norm of a Laplacian of a fluence map y), penalties for total fluence magnitude (i.e. "total MU"; ($C_k$=ΣY$_k$), penalties on dose values D=A·y, w at sampling points in various volumes or regions of interest (e.g., $C_i$=|Ay|$_1$ may be a penalty function that encourages an overall minimum dose to patient), and/or penalties on dose values D=A·y that correspond to prescription goals and constraints (such as any of the constraints described above) such as penalties for exceeding the maximum dose of an organ-at-risk $C_i$=|V$_k$(Ay)−d$_{max}$|$_1^+$, where V$_k$ gives the set of sampling points corresponding to an OAR k, and d$_{max}$ is the maximum dose for that organ, and |·|$_1^+$, is the one-sided norm operator.

In some variations, generating a radiation-firing matrix P may comprise setting up an optimization problem for minimizing the cost function C(v), and iterating through different sets of P such that the cost function C(y) is minimized while the following conditions are met:

$$y=P\cdot X \text{ and}$$

$$D=A\cdot y=A\cdot P\cdot X;$$

where D may be the predicted dose distribution, A may be the dose calculation matrix calculated in step 808, y may be the predicted total delivered radiation fluence, and X may be the planning patient PET image and/or planning patient CT image linearized into a 1D vector. Calculating 816 the total dose distribution to the patient may comprise multiplying the dose calculation matrix A with the radiation-firing matrix P and the planning patient CT image and/or the planning patient PET image X.

Figure 8B:
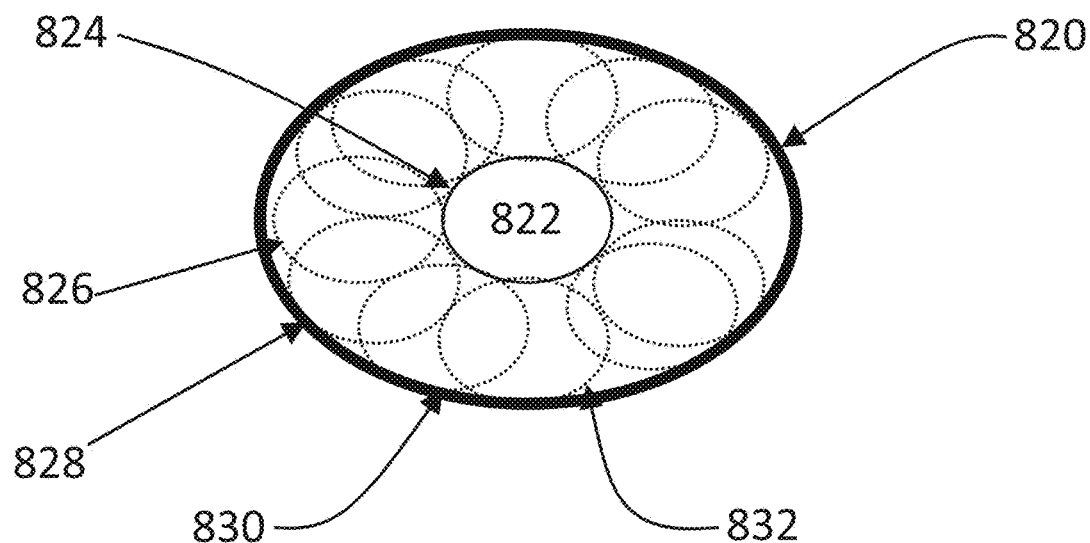
FIG. 8B depicts a schematic representation of shifting an image of a patient target volume (PTV) within a radiation-firing zone (RFZ) for calculating a family of DVH curves as part of the method of FIG. 8A.
Figure 8C:
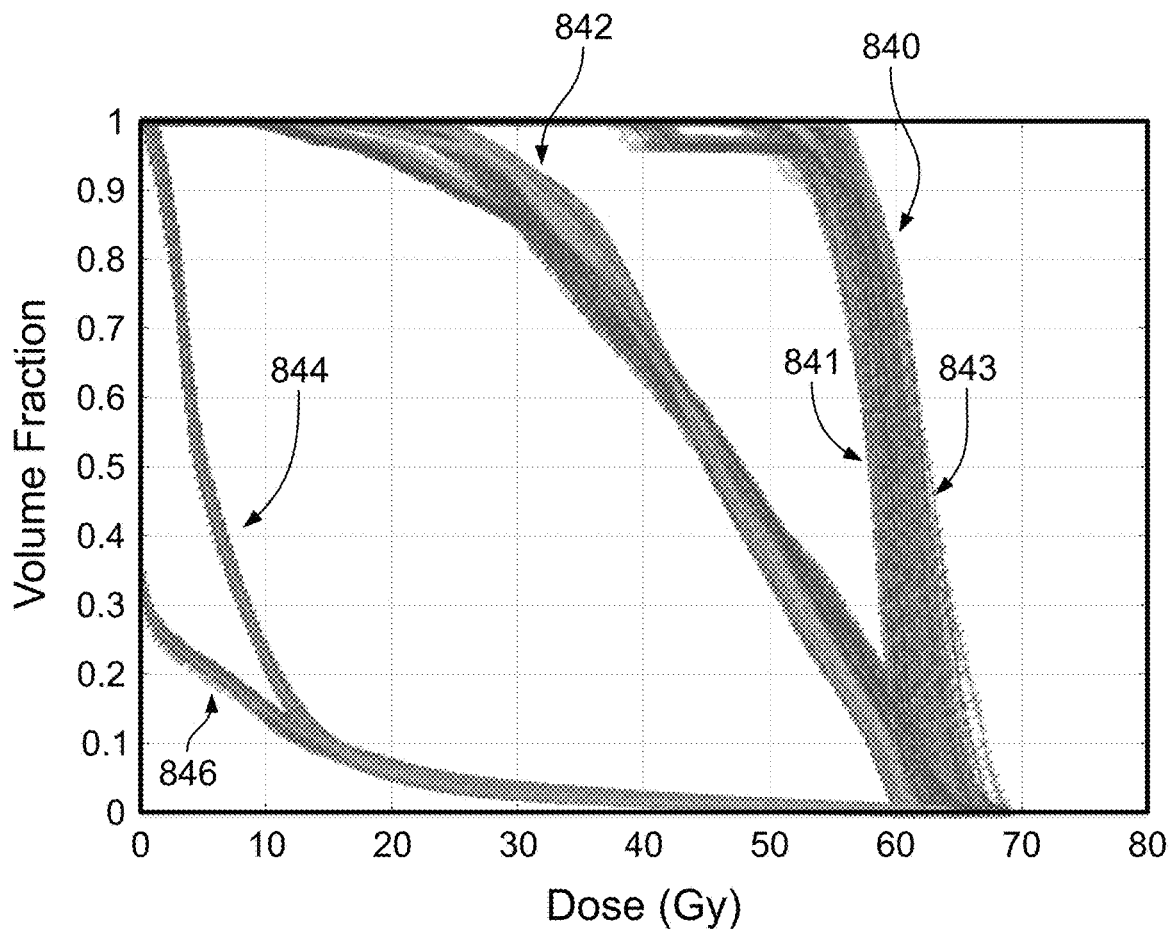
FIG. 8C depicts one example of a plurality of DVH curves calculated for the various shifted images of a PTV within the RFZ, including DVH curves for a PTV, RFZ, and two OARs.
Figure 8D:
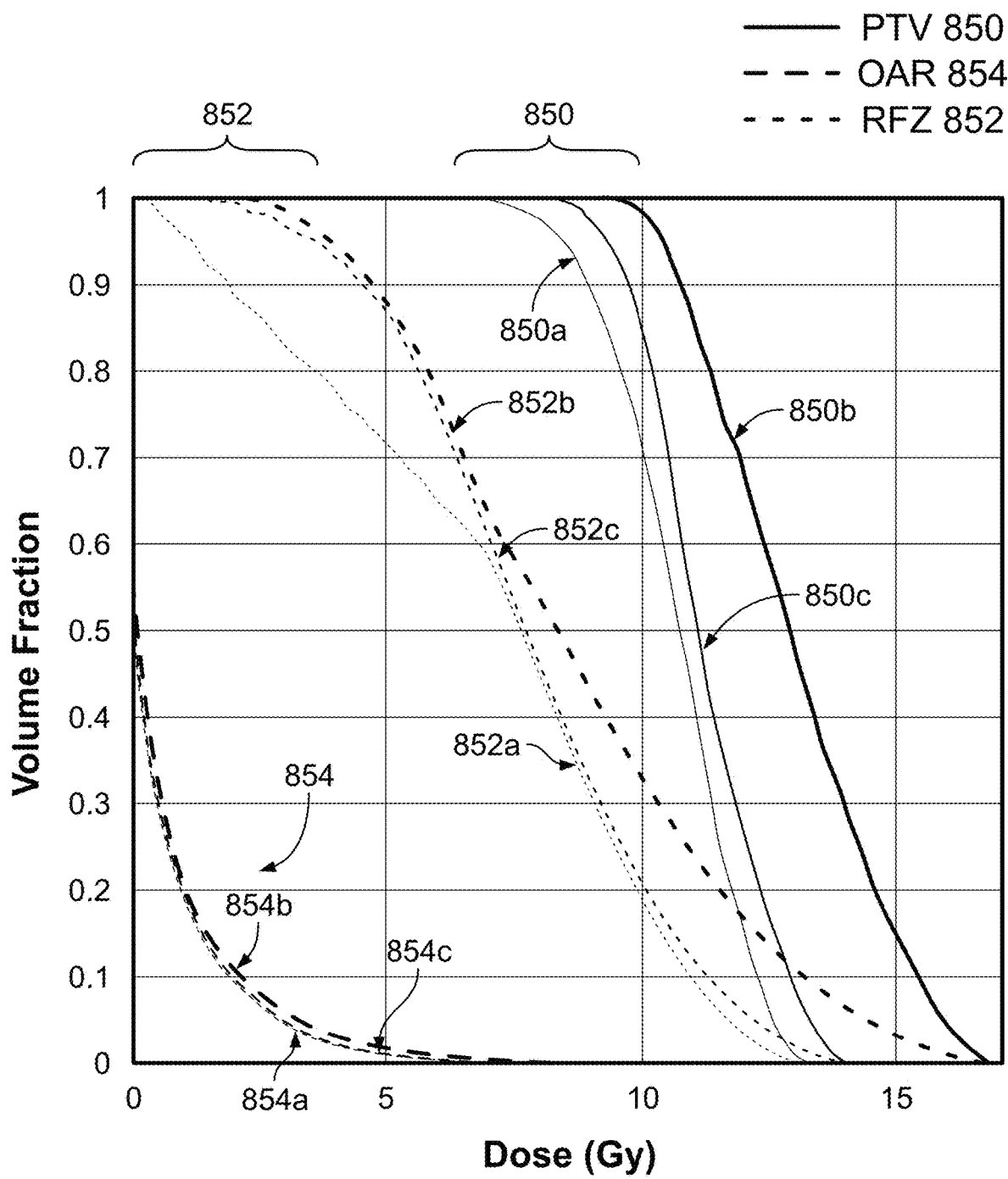
FIG. 8D depicts one example of bounded DVH curves for a PTV, a RFZ, and one OAR.

Bounded DVH curves comprise a min-DVH curve, a nominal DVH curve, and a max-DVH curve, where the min-DVH and max-DVH curves represent the likely range of dose distribution or treatment outcomes due to various factors and/or uncertainties at the time of treatment. Examples of factors and/or uncertainties that may affect the dose delivered on the day of treatment may include setup error, SUV variability, patient motion and/or shifts, and/or tumor (e.g., PTV) motion and/or shifts, and/or OAR motion and/or shifts. The nominal DVH curve may represent the dose distribution that adheres to the prescription of a clinician. The min-DVH curve may represent the lower bounds of a dose distribution, and the max-DVH curve may represent the upper bounds of a dose distribution, where the range defined by the min-DVH curve and the max-DVH curve represent variations in delivered dose due to various uncertainties at the time of treatment. The dose distribution or range bound by the min-DVH and max-DVH curves may be reviewed and/or evaluated by a clinician to determine whether a dose delivered within those bounds would be clinically relevant or therapeutic and/or desirable and/or safe for the patient. To derive the min-DVH and max-DVH curves for a particular PTV within a RFZ (or any region-of-interest, e.g., an OAR, RFZ, etc.), a treatment planning system may generate a plurality of images X'$_j$ that represent j positions of the PTV within the RFZ. The j positions may simulate the possible locations of the PTV within the RFZ on the day of treatment, due to, for example, patient movement and/or tumor movement. FIG. 8B is a schematic 2-D depiction of a RFZ 820 and a PTV 822 at a location 824 within the RFZ, where the location 824 is the location of the PTV 822 according to the planning patient CT image and/or the planning patient PET image X. To generate a family of DVH curves for PTV 822 that represent j positions of PTV 822 within RFZ 820, j images X'$_{1, 2, 3, \ldots, j}$ may generated by performing rigid 3-D shifts of the PTV 822 (and all anatomical structures of interest in the image X, e.g., PET-avid structures) to the j positions. That is, a first image X'$_1$ may have PTV 822 at location 826 within RFZ 820, a second image X'$_2$ may have PTV 822 at location 828 at location 826 within RFZ 820, a third image $X'_3$ may have PTV 822 at location 830 at location 826 within RFZ 820, a fourth image $X'_4$ may have PTV 822 at location 832 at location 826 within RFZ 820, and so forth. A family of j DVH curves may be calculated from the images $X'_{1, 2, 3, \ldots, j}$ by calculating $D_{1, 2, 3, \ldots, j} = A \cdot P \cdot X'_{1, 2, 3, \ldots, j}$, and plotting the volume fraction at each dose level. Optionally, in addition to calculating the DVH curves as the location of the PTV varies within the RFZ, in some variations, the intensity of the PTV in $X'_j$ may vary, which may simulate the effect of different uptake values (e.g., SUV) of a PET tracer on the day of treatment. For example, the intensity of the voxels in the PET image $X'_j$ may vary by ±25% from the nominal value (i.e., intensity from the planning PET image X). For example, for each location of the PTV within the RFZ, three DVH curves may be calculated: a first DVH curve for the nominal SUV level, a second DVH curve for a SUV level −25% from nominal, and a third DVH curve for a SUV level +25% from nominal. In some variations, a weight factor may be assigned to each image $X'_{1, 2, 3, \ldots, j}$ based on the probability/likelihood the PTV will be in a particular location and/or the anticipated dwell time of the PTV at that location. FIG. 8C depicts examples of families of DVH curves for a PTV, a RFZ, and two OARs that have been generated as described above. Each family of DVH curves may have from 3 DVH curves to 50 DVH curves or more (e.g., 10, 15, 25, 30, 45, 50, 70, 100 or more DVH curves). The family of DVH curves 840 may be for a PTV, the family of DVH curves 842 may be for a RFZ (within which the PTV is located), the family of DVH curves 844 may be for a first OAR, and the family of DVH curves 846 may be for a second OAR. FIG. 8D depicts bounded DVH curves for a PTV, RFZ, and an OAR (850, 852, 854, respectively), each having a min-DVH curve (850a, 852a, 854a, respectively), a max-DVH curve (850b, 852b, 854b, respectively), and a nominal DVH curve (850c, 852c, 854c, respectively). To derive a min-DVH curve for a PTV from the family of DVH curve 840, the left-most points 841 of that family of DVH curves (i.e., for each dose value, selecting the point with the lowest volume fraction, or for each volume fraction, select the point with the lowest dose) may be extracted and fitted with a curve. A max-DVH curve may be derived from a family of DVH curves by extracting the right-most points 843 of that family of DVH curves (i.e., for each dose value, selecting the point with the highest volume fraction, or for each volume fraction, select the point with the highest dose) and fitting those points with a curve. Alternatively or additionally, ordered statistics may be calculated from the DVH curves and used to evaluate treatment plans on the day of treatment. Examples of ordered statistics may include, but are not limited to, the maximum and minimum values of a DVH curve, the 5% value and the 95% value of a DVH curve, the 2% value and the 98% value of a DVH curve, absolute minimum and maximum dose values, as well as upper and lower thresholds for a homogeneity index, upper and lower thresholds for a conformality index, etc.

On the day of treatment, a DVH curve may be calculated based on imaging data (and/or biological and/or physiological data extracted from the imaging data and/or other sources). The DVH curve may be calculated at the start of the treatment session (e.g., before the therapeutic radiation source is activated), for example, by multiplying the radiation-firing matrix P with the acquire imaging data (e.g., a PET prescan image X): $D = P \cdot X$. If the calculated DVH curve is within the range defined by the min-DVH curve and max-DVH curve, treatment may proceed according to the treatment plan. Optionally, one or more DVH curves may be calculated throughout the treatment session based on real-time acquired imaging data and/or biological and/or physiological data, and the real-time generated DVH curves may be compared with the bounded DVH curves to determine whether radiation delivery should continue according to the treatment plan. Calculating a DVH curve based on imaging data (which may be an incomplete or noisy, low-signal-to-noise-ratio image x) may comprise calculating a dose D by multiplying the radiation firing matrix P with the imaging data: $D = P \cdot x$. As described previously, some systems may comprise a GUI presented on a display or monitor that overlays currently-calculated DVH curve with the bounded DVH curves, and/or providing one or more visual and/or audio notifications of whether a currently-calculated DVH curve is within the range defined by the bounded DVH curves. Re-evaluating radiation delivery and treatment at the start of a treatment session and/or during the session may help provide feedback to the clinician as to whether the treatment can be further tailored to a patient's changing conditions.

While the methods of evaluating treatment plans described above (e.g., as depicted in FIGS. 4-7) may be employed separately in any of the adaptive radiotherapy methods described herein (as depicted in FIGS. 2A-2D), it should be understood that one or more of these methods may be used in parallel with each other (e.g., simultaneously). For example, a radiation treatment system and/or a clinician may review updated PQI values and updated clinical parameters (e.g., biological activity and/or physiological and/or anatomical data) simultaneously when determining whether a treatment plan is appropriate for the patient at the current treatment session (e.g., combining the methods depicted and described with reference to FIGS. 4-5). Alternatively, evaluating a treatment plan may comprise reviewing updated clinical parameters and DVH curves simultaneously (e.g., combining the methods depicted and described with reference to FIGS. 5-6). Alternatively, evaluating a treatment plan may comprise reviewing updated PQI values and DVH curves simultaneously (e.g., combining the methods depicted and described with reference to FIGS. 4 and 6). In some variations, real-time acquired clinical parameter data, PQI values, and/or DVH curves may be reviewed and considered when determining whether a treatment plan is appropriate for a patient at a treatment session. This may allow the suitability of a treatment plan for the patient at that particular time point to be evaluated using multiple criteria. For example, if the clinical parameters of the patient at the time of treatment fall outside of the pre-calculated range of acceptable clinical parameters, the treatment system may calculate updated PQI values, and evaluate whether those updated PQI values are within the pre-calculated range of acceptable PQI values. That is, even though certain clinical parameters of a patient may not be within prescribed ranges, it is possible that the changes in these parameters may have certain synergies such that the treatment plan calculated based on the original set of clinical parameters would still provide the prescribed dose distribution. Calculating an updated PQI and/or updated DVH curve may reveal such synergies and a clinician and/or radiation therapy system may decide to proceed with treatment if one or more of updated clinical parameters, updated DVH, and/or updated PQI values are within acceptable ranges.

In some variations, a treatment plan may be generated based on one or more of PQI values, clinical parameters, and/or DVH curves. For example, a treatment planning system may generate a treatment plan based on an acceptable range of PQI values, calculate a range of clinical parameters within which the treatment plan would still be within the acceptable range of PQI values, and then evaluate whether the calculated range of clinical parameters is appropriate for the patient (which may be determined by the controller using patient-specific data and/or a clinician). If the calculated range of clinical parameters is not appropriate for the patient, the treatment planning system may iterate on a range of clinical parameters selected by the controller and/or clinician that is appropriate for the patient, generate a new treatment plan, and calculate PQI values for the new treatment plan.

EXAMPLE USE CASES

Example Use Case #1: Offline Adaptation for Regions of Tumor Hypoxia

A patient presents without hypoxic regions during the diagnosis and treatment planning session(s) or simulations, but prior to the radiation treatment session, a clinician may suspect that there may be one or more regions of tumor hypoxia. During setup imaging scans (e.g., pre-scan) at the start of a treatment session or fraction and/or imaging data acquisition during the treatment session, a region of the tumor is determined to be hypoxic based on acquired functional imaging data (for example, [$^{18}$F]HX4 PET data, [$^{18}$F]FAZA PET data, [$^{18}$F]FMISO PET data, and the like). The patient's original radiotherapy plan may be delivered for the current fraction or session, providing the originally planned dose to the patient.

The patient's care team (e.g., clinicians) may update the treatment plan based on the hypoxic imaging data for the next radiotherapy fraction. For example, the care team may transfer the hypoxic imaging data from the treatment system into the treatment planning system. The treatment plan may be updated to modify dose to the hypoxic region(s). For example, the updated treatment plan may provide a new simultaneous integrated boost intensity modulated radiotherapy (SIB-IMRT) fraction which increases the dose delivered to the radioresistant region of tumor hypoxia. Dose to the hypoxic region is boosted by a factor proportional to the maximum dose for the region in the original treatment plan based. The updated treatment plan may be used for radiation delivery in the next fraction.

After each subsequent fraction of the treatment, the patient's tumor hypoxia may be re-evaluated and the boost delivered to the patient's tumor hypoxia (both absolute dose values and target boost region) may be adapted using the hypoxia data acquired from this subsequent fraction and previous fractions to further adapt the patient's course of treatment.

Example Use Case #2: Online & Offline Adaptation for Regions of Tumor Hypoxia

A patient presents with hypoxic regions during diagnosis and treatment planning session(s) and/or simulation. During setup imaging scans (e.g., pre-scan) at the start of a radiation treatment session (or fraction) and/or imaging data acquisition during the treatment session, a region of the tumor is determined to be hypoxic based on acquired functional imaging data (for example, [$^{18}$F]HX4 PET data, [$^{13}$F]FAZA PET data, [$^{18}$F]FMISO PET data, and the like).

The current treatment plan may be updated to modifying dose to the hypoxic region(s) during the current treatment session or fraction. For example, the updated treatment plan may provide a more precise simultaneous integrated boost intensity modulated radiotherapy (SIB-IMRT) fraction than what was originally planned, increasing the dose delivered to the radioresistant region of tumor hypoxia. Dose to the hypoxic region is boosted by a factor proportional to the maximum dose for the region in the original treatment plan based. In some variations, the treatment system may comprise an online treatment planning system, which may be configured to receive and/or store the hypoxic imaging data and to calculate updates or modifications to the current treatment plan. The modified treatment plan may then be delivered to the patient during this current fraction, providing a more precise and effective treatment that may provide more clinical benefit to the patient.

After each fraction of the treatment, the patient's tumor hypoxia is re-evaluated and the boost delivered to the patient's tumor hypoxia (both absolute dose values and target boost region) is adapted again using the hypoxia data acquired from previous fractions, in order to help expedite the online treatment planning process for the next fraction.

Example Use Case #3: Real-Time Adaptation for Regions of Tumor Hypoxia

A patient presents with hypoxic regions during diagnosis and treatment planning session(s) and/or simulation. The patient may arrive for radiation treatment with a treatment plan created using functional imaging defining an expected region of tumor hypoxia.

During the treatment session, the exact region of the tumor hypoxia may be determined based on functional imaging data acquired in real-time (for example, [$^{18}$F]HX4 PET data, [$^{18}$F]FAZA PET data, [$^{18}_F$]FMISO PET data, and the like). In real-time, the dose to the exact hypoxic regions detected may be modified, which may help deliver more dose to the radioresistant regions of tumor hypoxia without requiring a replanning step. In some variations, the dose modification and/or any other modulations to the current treatment plan may be calculated by treatment delivery software modules of the treatment system. During the treatment session, the biological activity and/or physiological data feedback and/or the any dose modulations and/or any modulations to the treatment plan, may be displayed as active treatment parameters for patient monitoring. This may help provide additional feedback to the patient's care time (e.g., clinicians) during the treatment session.

At the conclusion of the current treatment session or fraction, the patient's tumor hypoxia may be re-evaluated. For example, the expected boost delivered to the patient's tumor hypoxia (both absolute dose values and target boost region) may be further adapted using the hypoxia data acquired from previous fractions, in order to help improve the ability of the treatment delivery software modules to modulate the dose in the next fraction.

Example Use Case #4: Online Adaptation for Cardiac Perfusion

A patient presents with cardiac perfusion defects (e.g., from a previous course of radiotherapy) and is now undergoing a second course for a recurrence of a thoracic cancer. In order to provide an improved dose-sparing effect for the patient's cardiac perfusion, the patient's care team decides to adapt the treatment plan at the time of treatment (e.g., perform an online adaptation) based on physiological characteristics acquired just prior to radiation delivery. For example, at the start of a treatment session, cardiac perfusion PET imaging data may be acquired (for example, [$^{15}$O] H$_2$O,

[$^{13}$N] Ammonia, and more have been shown to be effective for the extraction of physiological characteristics via functional imaging).

The patient may arrive for treatment with an initial (or current) treatment plan created using previously acquired imaging data (e.g., functional imaging data) that may define an expected region of the patient's cardiac perfusion defects. Imaging data may be acquired during the fraction's initial setup pre-scans, and a precise region of cardiac perfusion defect may be determined based on the imaging data. If a cardiac perfusion defect is detected and noted to be substantively different than the simulation based on the blood flow characteristics extracted from the imaging data, the patient's care team may revise the current treatment plan to modify dose delivery such that cardiac perfusion defect regions are exposed to lower levels of radiation and that the delineation of targets near the cardiac perfusion defect regions is refined. For example, updating or adapting the treatment plan may comprise modifying absolute dose values and the target region delineations to the defect regions and the areas around the defect regions. Generally, the updates would be reducing the number of available firing positions and increasing the dose delivered at certain firing positions to increase avoidance of the defect regions. These revisions to the treatment plan may help to provide a better dose gradient, isodose lines, and dose-volume histogram with respect to the cardiac perfusion defect regions. In some variations, cardiac perfusion imaging data may be transferred into an online treatment planning system of the treatment system for updating the treatment plan.

The modified treatment plan may then be delivered to the patient during this current fraction, which may help provide a more effective treatment with less negative side effects that will provide more overall clinical benefit to the patient. After each treatment fraction, the patient's cardiac perfusion defects may be re-evaluated and the specific dose delivered to the patient (both absolute dose values and target/avoidance regions) may be adapted again using the physiological cardiac perfusion data acquired during previous fractions. This may help to expedite the online treatment planning process for the next fraction.

Example Use Case #5: Online & Offline Adaptation for Immuno-Response

A patient presents with a HER2 positive primary tumor and aggressive HER2 positive metastases during diagnosis and treatment planning session(s) and/or simulation. It is suspected that there may be additional metastases and/or changes in HER2 expression by the time radiation treatment begins. Imaging data may be acquired during the fraction's initial setup pre-scans and/or during the treatment session, and a precise region and amount of HER2 expression may be determined based on this imaging data. For example, PET imaging data may be acquired using the 5F7 Anti-HER2 Nanobody radiolabeled with $^{18}$F via residualizing label, referred to as $^{18}$F-RL-I-5F7, and via protein labelling, referred to as $^{18}$F-SFB, as these labels have been shown to provide effective biological imaging of HER2 gene expression. The radiolabeled proteins would then be detected on the PET scan, concentrating in regions where HER2 receptors are active, allowing the differential in concentration and relative intensities to be quantized to precisely identify regions of HER2 gene expression.

The patient's care team may update the current treatment plan by, for example, modifying dose to the HER2 positive regions, providing a higher dose to regions of HER2 expression, even adding a new target region based on newly discovered metastatic tumor with HER2 expression. In some variations, HER2 expression imaging data may be transferred into an online treatment planning system of the treatment system for updating the treatment plan.

The modified treatment plan may then delivered to the patient during this current fraction, which may help provide a more precise and effective treatment with increased clinical benefit to the patient. After each treatment fraction, the patient's HER2 expression data may be re-evaluated and the dose delivered to the patient's HER2 positive tumors may be further adapted using the HER2 expression data acquired from previous fractions. For cases looking for radiopriming of HER2 active regions for system therapy, the plan may be modified to increase the amount of radiation to a HER2 expressing region in order to amplify the effect of systemic therapies at work in those regions. Alternatively, for cases where additional radiation may interfere with the systemic treatments from immunotherapies interacting with HER2 gene expression, the plan may be modified to decrease the amount of radiation to a HER2 expressing region and instead focus on non-expressing nodes to take advantage of the abscopal effect. This may help to expedite the online treatment planning process for the next fraction.

Any of the radiation treatment methods and/or systems described herein may be used alone or in conjunction with other tumor therapies. For example, adaptive radiotherapy may be used in conjunction with surgery and/or chemotherapy and/or immunotherapy, and/or gene therapy. Furthermore, the treatment methods and/or systems herein may use any type of tracer that may help to identify regions of interest or targets (e.g., irradiation-target regions and/or irradiation-avoidance regions). For example, one or more of the following PET tracers may be used: 18F-FDG, 18F-NaF, 18FHX4, 18FFAZA, 18FFMISO, radiolabeled 5F7 anti-HER2 nanobody labeled with 18F, 11C-Palmitate and 14-(R,S)-18F-fluoro-6-thiaheptadecanoic acid, 15O-Water, 13N-Ammonia, 82Rb-Rubidium, flurorothymidine, 68Ga-Gallium, and 68Ge-Germanium. PET tracers may comprise agents that bind to specific proteins, cell markers, metabolic products, and the like. Alternatively or additionally, any of the systems and methods described herein may use one or more fiducial markers, radiopaque markers, or any other identifiers that allow the ROIs or target regions to be tracked and identified during a treatment session.

System Controller

The radiotherapy treatment planning systems and radiation treatment systems described herein may each comprise a controller having a processor and one or more memories. In some variations, the planning system and the treatment system may share a controller, as may be desirable. A controller may comprise one or more processors and one or more machine-readable memories in communication with the one or more processors. The controller may be connected to a radiation therapy system and/or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, imaging data acquired during a previous treatment session and/or current treatment session (e.g., real-time imaging data), biological activity, physiological and/or anatomical data extracted from imaging data, updated or adapted treatment plans, updated or adapted dose delivery instructions, radiation therapy system instructions (e.g., that may direct the operation of the gantry, therapeutic radiation source, multi-leaf collimator, and/or any other components of a radiation therapy system and/or diagnostic or treatment planning system), and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the treatment planning system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices.

Some variations of a treatment planning system for generating fluence maps may comprise a display device that may allow an operator to view graphical and/or textual representations of fluence maps, and/or dose distributions, and/or regions of interest, and/or volumes of interest, and/or patient anatomical images, and/or patient data (e.g., physiological and/or biological), and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system and/or radiation treatment system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

The invention claimed is:

1. A method for adapting a radiotherapy treatment during a radiation treatment session, comprising:
    measuring, during the radiation treatment session, biological activity data of at least one patient region based on positron emission data acquired during the radiation treatment session using one or more positron emission tomography (PET) detectors;
    calculating a dose volume histogram (DVH) in real-time for the at least one patient region based on the measured biological activity data of the at least one patient region;
    comparing the calculated, real-time DVH with a pre-determined bounded DVH defined by a radiotherapy treatment plan prescribed for the patient, the pre-determined bounded DVH comprising a minimum DVH curve and a maximum DVH curve;
    displaying the comparison of the calculated, real-time DVH and the pre-determined bounded DVH to a user; and
    updating the radiotherapy treatment in real-time during the radiation treatment session when the displayed comparison indicates the calculated, real-time DVH does not satisfy the pre-determined bounded DVH.

2. The method of claim 1, wherein the pre-determined bounded DVH is generated based on an initial biological activity range, and wherein the initial biological activity range is measured during the radiation treatment session prior to measuring the biological activity data.

3. The method of claim 1, wherein the pre-determined bounded DVH is generated based on an initial biological activity range, and wherein the initial biological activity range is measured during a previous radiation treatment session.

4. The method of claim 1, wherein updating the radiotherapy treatment comprises changing a dosimetric objective of the at least one patient region.

5. The method of claim 1, wherein updating the radiotherapy treatment comprises changing the geometry of the at least one patient region, one or more dose-shaping structures, or both the at least one patient region and one or more dose-shaping structures.

6. The method of claim 1, wherein the radiotherapy treatment plan comprises an initial number of treatment sessions and wherein updating radiotherapy treatment comprises updating the radiotherapy treatment plan by changing the number of treatment sessions from the initial number of treatment sessions.

7. The method of claim 1, wherein the radiotherapy treatment plan comprises an initial treatment session duration and wherein updating the radiotherapy treatment comprises changing the treatment session duration from the initial treatment session duration.

8. The method of claim 1, wherein updating the radiotherapy treatment comprises updating the radiotherapy treatment plan by changing a fractionation pattern over multiple treatment sessions.

9. The method of claim 1, wherein measuring biological activity data comprises measuring a standard uptake value (SUV) of a PET tracer of the at least one patient region.

10. The method of claim 9, wherein the PET tracer is selected from the group consisting of: 18F-fluorodeoxyglucose (18F-FDG), 18F-sodium fluoride (18F-NaF), 18F-flortanidazole (18F-HX4), 18F-fluoroazomycin arabinoside (18F-FAZA), 18F-fluoromisonidazole (18F-FMISO), radiolabeled 5F7 anti-human growth factor receptor type 2 (anti-HER2) nanobody labeled with 18F, 11C-Palmitate, 14-(R,S)-18F-fluoro-6-thia-heptadecanoic acid, 15O-Water,13N-Ammonia, 82Rb-Rubidium, fluorothymidine, 68Ga-Gallium, 68Ge-Germanium, F18-Fluciclovine, Ga68-DOTATATE, Cll-Choline, Ga68-prostate specific membrane antigen (Ga68-PSMA), F18-piflufolastat prostate specific membrane antigen (F18-PyL(PSMA)), programmed death-ligand 1 (PD-L1), 13N-nitrogen, 11C-methionine, 18F-fluoroerythronitroimidazole, 3'-Aza-2'-[18F]fluorofolic acid, N-succinimidyl 3-((4-(4-(18)F-fluorobutyl)-1H-1,2,3-triazol-1-yl)methyl)-5-(guanidinomethyl)benzoate, and 1-(2'-deoxy-T-[18F]fluoroarabinofuranosyl) cytosine (18F-FAC).

11. The method of claim 1, wherein the biological activity data comprises tissue metabolism data.

12. The method of claim 1, wherein the biological activity data comprises osteogenic activity.

13. The method of claim 1, wherein the biological activity data comprises oxygenation levels.

14. The method of claim 1, wherein the biological activity data comprises human growth factor receptor type 2 (HER2) genetic expression.

15. The method of claim 1, wherein the biological activity data comprises free fatty acid uptake.

16. The method of claim 1, wherein the biological activity data comprises physiological activity data.

17. The method of claim 16, wherein the physiological activity data comprises blood flow data.

18. The method of claim 16, wherein the physiological activity data comprises vascularity of the at least one patient region.

19. The method of claim 16, wherein the physiological activity data comprises morphological shifts in spiculation of a tumor region in the at least one patient region.

20. The method of claim 16, wherein the physiological activity data comprises lymphatic activity data.

21. The method of claim 1, wherein measuring biological activity data comprises quantitatively measuring PET tracer kinetics in the at least one patient region.

22. The method of claim 1, wherein the radiotherapy treatment plan comprises a target dose distribution and wherein updating radiotherapy treatment comprises changing the target dose distribution.

23. The method of claim 1, wherein updating the radiotherapy treatment comprises updating the radiotherapy treatment plan for a future radiation treatment session.

24. The method of claim 1, wherein measuring biological activity data of the at least one patient region further comprises acquiring a functional image of the at least one patient region using magnetic resonance imaging, laser scanning fluorescence imaging, ultrasound imaging, magnetic particle imaging, or single-photon emission computed tomography.

25. The method of claim 1, wherein measuring biological activity data of the at least one patient region comprises:
    providing a PET tracer to the patient; and
    measuring the positron emission data from the at least one patient region.

26. The method of claim 25, wherein the PET tracer comprises a hypoxia PET tracer selected from a group consisting of: 18F-flortanidazole (18F-HX4), 18F-fluoroazomycin arabinoside (18F-FAZA), and 18F-fluoromisonidazole (18F-FMISO), and wherein measuring positron emission data comprises measuring hypoxia PET tracer uptake values across the at least one patient target region, and wherein updating the radiotherapy treatment comprises increasing a radiation dose to one or more patient regions determined to have hypoxia PET tracer uptake values that exceed a threshold.

27. The method of claim 25, wherein the PET tracer comprises a human growth factor receptor type 2 (HER2) PET tracer selected from a group consisting of: 5F7 Anti-HER2 nanobody labeled with 18F (18F-RL-I-5F7) and 18F-N-succinimidyl-4-[18F]fluorobenzoate (18F-SFB), wherein measuring positron emission data comprises measuring HER2 PET tracer uptake values across the at least one patient target region, and wherein updating the radiotherapy treatment comprises increasing a radiation dose to one or more patient regions determined to have HER2 PET tracer uptake values that exceed an upper threshold.

28. The method of claim 27, further comprising:
measuring HER2 PET tracer uptake values of patient regions outside of the at least one patient region; and
identifying patient regions outside of the at least one patient region having HER2 PET tracer uptake values that exceed the upper threshold;
wherein updating the radiotherapy treatment comprises changing the dose distribution to include the identified patient regions for radiation dose delivery.

29. The method of claim 25, wherein the PET tracer comprises a human growth factor receptor type 2 (HER2) PET tracer selected from a group consisting of: 5F7 Anti-HER2 nanobody labeled with 18F (18F-RL-I-5F7) and 18F-N-succinimidyl-4-[18F]fluorobenzoate (18F-SFB), wherein measuring positron emission data comprises measuring HER2 PET tracer uptake values across the at least one patient region, and wherein updating the radiotherapy treatment comprises decreasing a radiation dose to one or more patient regions determined to have HER2 PET tracer uptake values that exceed an upper threshold.

30. The method of claim 1, further comprising updating radiotherapy treatment if the measured biological activity data is not within an initial biological activity range.

31. The method of claim 30, wherein the radiotherapy treatment is not updated if the measured biological activity data is within the initial biological activity range.

32. The method of claim 30, further comprising displaying a notification if the measured biological activity data is not within the initial biological activity range.

33. The method of claim 30, wherein the initial biological activity range is a clinician-approved biological activity range.

34. The method of claim 30, wherein the initial biological activity range is calculated based on a clinician-approved bounded dose volume histogram (DVH) for the radiotherapy treatment plan.

35. The method of claim 1, wherein updating radiotherapy treatment comprises updating the radiotherapy treatment if the calculated, real-time DVH is not within the pre-determined bounded DVH.

36. The method of claim 35, wherein the pre-determined bounded DVH is calculated based on one or more of the following: dose delivered to the at least one patient region in one or more previous treatment session, clinician-approved dose delivery uncertainty, maximum dose level and minimum dose level.

37. The method of claim 1, wherein measuring biological activity data comprises acquiring PET imaging data during a treatment session, wherein the method further comprises comparing the acquired PET imaging data with previously-acquired PET imaging data, and wherein updating the radiotherapy treatment comprises adapting the radiotherapy treatment based on the acquired PET imaging data.

38. The method of claim 37, wherein the acquired PET imaging data comprises a tracer flow rate during the treatment session, and wherein comparing the acquired PET imaging data with previously-acquired PET imaging data comprises comparing the tracer flow rate during the treatment session with a tracer flow rate during a previous session.

39. The method of claim 37, wherein updating the radiotherapy treatment comprises calculating an adapted radiotherapy treatment plan using the acquired PET imaging data as a new treatment planning image.

40. The method of claim 37, wherein updating the radiotherapy treatment comprises adjusting contours of the at least one patient region according to the acquired PET imaging data.

41. The method of claim 1, wherein the minimum DVH curve and the maximum DVH curve are determined from a group of DVHs calculated for the at least one patient region.

42. The method of claim 41, wherein each member of the group of DVHs is a DVH calculated based on a different estimated position of the at least one patient region.

43. The method of claim 41, wherein the minimum DVH curve is determined by
selecting, for each dose value, a point from the group of DVHs with the lowest volume fraction, or, for each volume fraction, a point from the group of DVHs with the lowest dose; and
fitting the selected points with a curve.

44. The method of claim 41, wherein the maximum DVH curve is determined by
selecting, for each dose value, a point from the group of DVHs with the highest volume fraction, or, for each volume fraction, a point from the group of DVHs with the highest dose; and
fitting the selected points with a curve.

45. The method of claim 1, further comprising:
generating an alert to the user when the calculated, real-time DVH is outside a range defined by the pre-determined bounded DVH.

46. The method of claim 1, wherein the updating the radiotherapy treatment in real-time based on the displayed comparison improves efficiency and accuracy in the radiotherapy treatment workflow.

47. A method for radiotherapy treatment comprising:
measuring biological activity data of at least one patient region based on positron emission data acquired during a radiation treatment session using one or more positron emission tomography (PET) detectors;
calculating a dose volume histogram (DVH) for the at least one patient region based on a radiotherapy treatment plan and the measured biological activity data;
comparing the calculated DVH with a pre-determined bounded DVH, the pre-determined bounded DVH comprising a minimum DVH curve and a maximum DVH curve;
displaying the comparison of the calculated DVH and the pre-determined bounded DVH to a user; and updating the radiotherapy treatment based on the displayed comparison between the calculated DVH and the pre-determined bounded DVH; and applying the updated radiotherapy treatment to the at least one patient region during the treatment session.

48. The method of claim 47, wherein the pre-determined bounded DVH is generated based on a pre-determined biological activity range, and wherein the pre-determined biological activity range is a clinician-approved biological activity range.

49. The method of claim 47, wherein measuring biological activity data of the at least one patient region comprises measuring hypoxic PET tracer uptake values across the at least one patient region, and wherein applying the updated radiotherapy treatment comprises applying radiation such that a radiation dose to patient regions with higher hypoxic PET tracer uptake values is greater than a radiation dose to patient regions with lower hypoxic PET tracer uptake values.

50. The method of claim 47, wherein measuring biological activity data comprises acquiring PET imaging data during a treatment session, wherein the method further comprises comparing the acquired PET imaging data with previously-acquired PET imaging data, and wherein updating the radiotherapy treatment comprises updating the radiotherapy treatment if a difference between the acquired PET imaging data and the previously-acquired PET imaging data exceeds a pre-determined threshold.

51. The method of claim 50, wherein updating the radiotherapy treatment comprises calculating an updated treatment plan using the acquired PET imaging data as a new treatment planning image.

52. The method of claim 47, wherein calculating the DVH for the at least one patient region based on the measured biological activity data acquired during the radiation treatment session comprises multiplying a radiation-firing matrix with PET imaging data acquired via the one or more PET detectors during the radiation treatment session, wherein the radiation-firing matrix is calculated by iteratively solving for a fluence map that minimizes at least one cost function.

53. The method of claim 47, further comprising generating an alert to the user when the calculated DVH is outside a range defined by the pre-determined bounded DVH.

* * * * *